United States Patent
Malona et al.

(10) Patent No.: US 11,098,057 B2
(45) Date of Patent: Aug. 24, 2021

(54) 9,10,11,12-TETRAHYDRO-8H-[1,4]DIAZEPINO[5',6':4,5]THIENO[3,2-F]QUINOLIN-8-ONE COMPOUNDS AND USES THEREOF

(71) Applicant: Celgene CAR LLC, Pembroke (BM)

(72) Inventors: John Malona, Brookline, MA (US); Alexander L. Ruchelman, Cream Ridge, NJ (US)

(73) Assignee: Celgene CAR LLC, Pembroke (BM)

( * ) Notice: Subject to any disclaimer, the term of this patent is extended or adjusted under 35 U.S.C. 154(b) by 0 days.

(21) Appl. No.: 16/494,722

(22) PCT Filed: Mar. 15, 2018

(86) PCT No.: PCT/US2018/022548
§ 371 (c)(1),
(2) Date: Sep. 16, 2019

(87) PCT Pub. No.: WO2018/170204
PCT Pub. Date: Sep. 20, 2018

(65) Prior Publication Data
US 2020/0102327 A1  Apr. 2, 2020

Related U.S. Application Data

(60) Provisional application No. 62/472,027, filed on Mar. 16, 2017.

(51) Int. Cl.
*C07D 495/14* (2006.01)
*C07D 513/14* (2006.01)
*A61K 31/4353* (2006.01)
*A61K 31/551* (2006.01)

(52) U.S. Cl.
CPC .................. *C07D 495/14* (2013.01)

(58) Field of Classification Search
CPC ................ C07D 495/14; C07D 513/14; A61K 31/4353; A61K 31/551
See application file for complete search history.

(56) References Cited

U.S. PATENT DOCUMENTS

| | | |
|---|---|---|
| 7,838,674 B2 | 11/2010 | Schlapbach et al. |
| 9,458,175 B2 | 10/2016 | Alexander et al. |
| 9,790,235 B2 | 10/2017 | Alexander et al. |
| 10,138,256 B2 | 11/2018 | Alexander et al. |
| 10,253,040 B1 | 4/2019 | Alexander et al. |
| 10,577,380 B2 | 3/2020 | Alexander et al. |
| 10,882,867 B2 | 1/2021 | Han et al. |
| 10,894,796 B2 | 1/2021 | Feigelson et al. |
| 2012/0022030 A1 | 1/2012 | Schlapbach et al. |
| 2013/0137708 A1 | 5/2013 | Garske et al. |
| 2014/0018343 A1 | 1/2014 | Romero et al. |
| 2019/0375762 A1 | 12/2019 | Alexander et al. |
| 2020/0102325 A1 | 4/2020 | Guo et al. |
| 2020/0102326 A1 | 4/2020 | Feigelson et al. |
| 2020/0148701 A1 | 5/2020 | Han et al. |
| 2021/0053984 A1 | 2/2021 | Alexander et al. |

FOREIGN PATENT DOCUMENTS

| | | |
|---|---|---|
| WO | WO-1995/26325 A2 | 10/1995 |
| WO | WO-2004/058762 A1 | 7/2004 |
| WO | WO-2005/105814 A1 | 11/2005 |
| WO | WO-2009/010488 A1 | 1/2009 |
| WO | WO-2014/149164 A1 | 9/2014 |
| WO | WO-2016/044463 A2 | 3/2016 |
| WO | WO-2018/170199 A1 | 9/2018 |
| WO | WO-2018/170200 A1 | 9/2018 |
| WO | WO-2018/170201 A1 | 9/2018 |
| WO | WO-2018/170203 A1 | 9/2018 |
| WO | WO-2018/170204 A1 | 9/2018 |

OTHER PUBLICATIONS

Anderson, D.R. et al., Benzothiophene inhibitors of MK2. Part 2: Improvements in kinase selectivity and cell potency, Bioorganic & Medicinal Chemistry Letters, 19: 4882-4884 (2009).
International Search Report for PCT/US2015/050495, 2 pages (dated Dec. 11, 2015).
International Search Report for PCT/US2018/022548, 4 pages (dated Jun. 26, 2018).
Natesan, S. et al., Binding Affinity Prediction for Ligans and Receptors Forming Tautomers and Ionization Species: Inhibition of Mitogen-Activated Protein Kinase-Activated Protein Kinase 2 (MK2), Journal of Medicinal Chemistry, 55(5): 2035-2047 (2012).
Center for Drug Evaluation and Research, Development of New Stereoisomeric Drugs, Published May 1, 1992.
Dumont, P., Perspective in the use of deuterated molecules as therapeutic agents, Revue IRE Tijdschrift, 6:2-10 (1982).
Foster, A. B., Deuterium Isotope Effects in the Metabolism of Drugs and Xenobiotics: Implications for Drug Design, Advances in Drug Research, 14:1-40 (1985).
O'Driscoll, C., Heavyweight drugs, Chem. & Industry, 24-26 (2009).
Tung, R. et al., The Development of Deuterium-Containing Drugs, Innovations in Pharmaceutical Technology, 32:24-26 (2010).
Anderson, D.R. et al., Benzothiophene inhibitors of MK2. Part 1: Structure-activity relationships assessments of selectivity and cellular potency, Bioorganic & Medicinal Chemistry Letters, 19: 4878-4881 (2009).
Fiore, M. et al., Targeting Mitogen-Activated Protein Kinase-Activated Protein Kinase 2 (MAPKAPK2, MK2): Medicinal Chemistry Efforts To Lead Small Molecule Inhibtors to Clinical Trials, Jrnl. Med. Chern., 59:3609-3634 (2016).

*Primary Examiner* — Bruck Kifle
(74) *Attorney, Agent, or Firm* — Choate, Hall & Stewart LLP; Kristen C. Buteau; Nicholas J. Pace

(57) ABSTRACT

The present invention provides compounds, compositions thereof, and methods of using the same.

15 Claims, No Drawings
Specification includes a Sequence Listing.

9,10,11,12-TETRAHYDRO-8H-[1,4] DIAZEPINO[5',6':4,5]THIENO[3,2-F] QUINOLIN-8-ONE COMPOUNDS AND USES THEREOF

CROSS-REFERENCE TO RELATED APPLICATIONS

The present application claims priority to U.S. Provisional Patent Application No. 62/472,027, filed on Mar. 16, 2017, the entirety of which is hereby incorporated by reference.

TECHNICAL FIELD OF THE INVENTION

The present invention relates to compounds useful as inhibitors of MK2 kinases. The invention also provides pharmaceutically acceptable compositions comprising compounds of the present invention and methods of using said compositions in the treatment of various disorders.

SEQUENCE LISTING

In accordance with 37 C.F.R. 1.52(e)(5), the present specification makes reference to a Sequence Listing submitted electronically in the form of a text file (entitled "2007878-0817_SL.txt" created on Nov. 8, 2019, 4,151 bytes in size). The entire contents of the Sequence Listing are herein incorporated by reference, with the intention that, upon publication (including issuance), this incorporated sequence listing will be inserted in the published document immediately before the claims.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

Mitogen-activated protein kinase-activated protein kinase 2 (MAPKAP K2 or MK2) mediates multiple p38 MAPK-dependent cellular responses. MK2 is an important intracellular regulator of the production of cytokines, such as tumor necrosis factor alpha (TNF-α), interleukin 6 (IL-6) and interferon gamma (IFNγ), that are involved in many acute and chronic inflammatory diseases, e.g. rheumatoid arthritis and inflammatory bowel disease. MK2 resides in the nucleus of non-stimulated cells and upon stimulation, it translocates to the cytoplasm and phosphorylates and activates tuberin and HSP27. MK2 is also implicated in heart failure, brain ischemic injury, the regulation of stress resistance and the production of TNF-α (see Deak et al., EMBO. 17:4426-4441 (1998); Shi et al., Biol. Chem. 383:1519-1536 (2002); Staklatvala., Curr. Opin. Pharmacol. 4:372-377 (2004), and Shiroto et al., J. Mol. Cardiol. 38:93-97 (2005)).

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of MK2. Such compounds have general formula I:

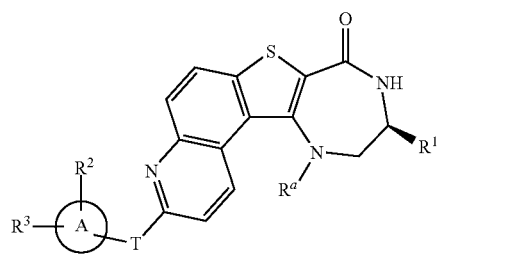

or a pharmaceutically acceptable salt thereof, wherein each of Ring A, T, $R^a$, $R^1$, $R^2$, and $R^3$, with respect to the formula I above, is as defined and described in embodiments herein.

Compounds of the present invention, and pharmaceutically acceptable compositions thereof, are useful for treating a variety of diseases, disorders or conditions, associated with abnormal cellular responses triggered by protein kinase-mediated events. Such diseases, disorders, or conditions include those described herein.

Compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF CERTAIN EMBODIMENTS

1. General Description of Compounds of the Invention

In certain embodiments, the present invention provides irreversible inhibitors of MK2. In some embodiments, such compounds include those of the formulae described herein, or a pharmaceutically acceptable salt thereof, wherein each variable is as defined and described herein.

In some embodiments, the present invention provides a compound of formula I:

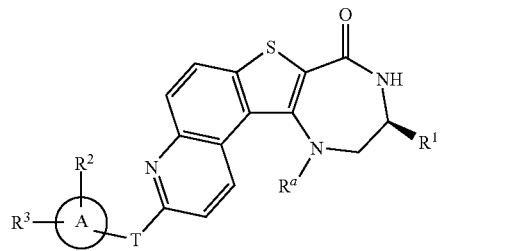

or a pharmaceutically acceptable salt thereof, wherein:
Ring A is phenyl, a 5-6 membered monocyclic heteroaryl ring having 1-3 nitrogens, or an 8-14 membered bicyclic heteroaryl ring having 1-4 heteroatoms independently selected from nitrogen, oxygen, and sulfur;
T is a bivalent moiety selected from —N(R)—, —O—, —S—, —S(O)—, —SO$_2$—, —C(S)—, —Si(R$^4$)$_2$—, —P(R$^5$)—, —P(O)$_2$—, or a bivalent saturated straight or branched 1-3 membered hydrocarbon chain, wherein the hydrocarbon chain is optionally substituted with oxo or —OR;
each R is independently hydrogen or an optionally substituted C$_{1-6}$ aliphatic, or:
  two R groups on the same nitrogen are taken together with the nitrogen to form a 3-7 membered saturated or partially unsaturated heterocyclic ring having 1-3 heteroatoms selected from nitrogen, oxygen, or sulfur;
R$^a$ is hydrogen or an optionally substituted C$_{1-6}$ aliphatic;
R$^1$ is —R or —(CH$_2$)$_p$R$^x$;
p is 0, 1, 2, or 3;
R$^x$ is —CN, —NO$_2$, halogen, —OR, —SR, —N(R)$_2$, —C(O)N(R)$_2$, —C(O)OR, —C(O)R, —N(R)C(O)R, —SO$_2$N(R)$_2$, or —N(R)SO$_2$;
R$^2$ is halogen, —CN, —SR$^y$, —S(O)R$^y$, —SO$_2$R$^y$, —OSO$_2$R, —OC(O)R$^y$, or —OP(O)$_2$OR$^y$;
each R$^y$ is independently selected from optionally substituted C$_{1-6}$ aliphatic or optionally substituted phenyl;
R$^3$ is hydrogen, optionally substituted C$_{1-6}$ aliphatic, —CN, —NO$_2$, halogen, —OR, —N(R)$_2$, —C(O)N(R)$_2$, —C(O)OR, -Cy, —C(O)N(R)-Cy, —C(O)—Cy, —O-Cy, —O—(CH$_2$)$_n$-Cy, —(CH$_2$)$_n$—O-Cy, —(CH$_2$)$_m$N(R)$_2$, —(CH$_2$)$_m$ OR, —N(R)—Cy, —N(R)—(CH$_2$)$_n$-Cy, —(CH$_2$)$_n$—N(R)-Cy, or —(CH$_2$)$_m$-Cy;
each R$^4$ is independently hydrogen, —OR, C$_{1-6}$ aliphatic, phenyl, or a 5-6 membered heteroaryl ring having 1-3 heteroatoms independently selected from nitrogen, oxygen, and sulfur;
each R$^5$ is independently —OR, C$_{1-6}$ aliphatic, phenyl, or a 5-6 membered heteroaryl ring having 1-3 heteroatoms independently selected from nitrogen, oxygen, and sulfur;
each of m and n is independently 0-4; and
each Cy is independently an optionally substituted ring selected from a 3-9 membered saturated or partially unsaturated monocyclic carbocyclic ring, a 3-9 membered saturated or partially unsaturated monocyclic heterocyclic ring having 1-3 heteroatoms independently selected from nitrogen, oxygen, and sulfur, phenyl, a 5-6 membered heteroaryl ring having 1-3 heteroatoms independently selected from nitrogen, oxygen, and sulfur, a 7-12 membered saturated or partially unsaturated fused or bridged bicyclic carbocyclic ring, or a 6-12 membered saturated or partially unsaturated fused or bridged bicyclic heterocyclic ring having 1-3 heteroatoms independently selected from nitrogen, oxygen, and sulfur.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "carbocyclic", "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "carbocyclic" (or "cycloaliphatic" or "carbocycle" or "cycloalkyl") refers to a monocyclic C$_3$-C$_8$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

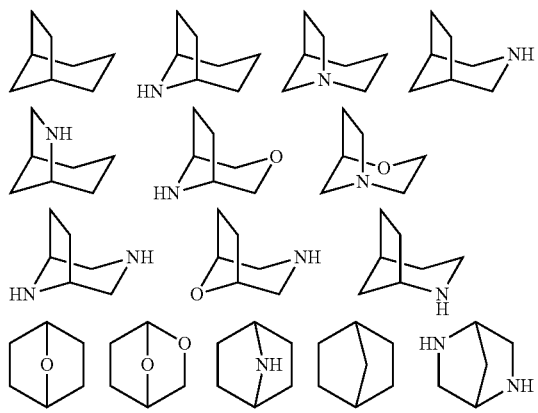

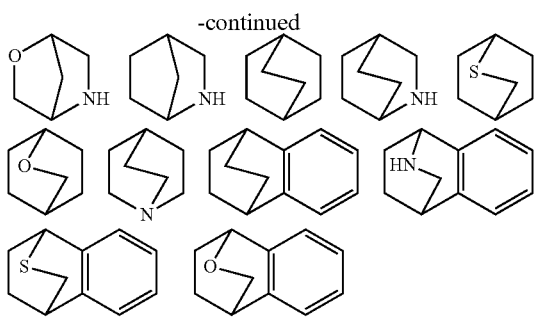

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_1$-6) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

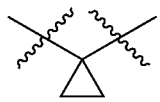

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system and exemplary groups include phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Exemplary heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Exemplary groups include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. "Substituted" applies to one or more hydrogens that are either explicit or implicit from the structure (e.g.,

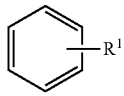

refers to at least

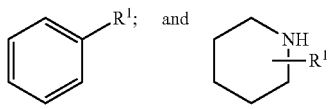

and refers to at least

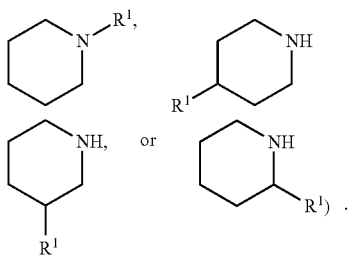

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —O$(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}$-Ph which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R)C(O)R°$; —$N(R°)C(S)R°$; —$(CH_2)_{0-4}N(R)C(O)NR°_2$; —$N(R°)C(S)NR°_2$; —$(CH_2)_{0-4}N(R)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —OC(O)$(CH_2)_{0-4}SR°$; —$(CH_2)_{0-4}SC(O)R°$; —$(CH_2)_{0-4}C(O)NR°_2$; —$C(S)NR°_2$; —$C(S)SR°$; —SC(S)SR°, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}S(O)_2R°$; —$S(O)_2NR°_2$; —$(CH_2)_{0-4}S(O)R$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —OP(O)$R°_2$; —OP(O)(OR°)$_2$; Si$R°_3$; —$(C_{1-4}$ straight or branched alkylene)O—N(R°)$_2$; or —$(C_{1-4}$ straight or branched alkylene)C(O)O—N(R°)$_2$, wherein each R° may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^●$, -(haloR$^●$), —$(CH_2)_{0-2}OH$, —$(CH_2)_{0-2}OR^●$, —$(CH_2)_{0-2}CH(OR^●)_2$; —O(haloR$^●$), —CN, —$N_3$, —$(CH_2)_{0-2}C(O)R^●$, —$(CH_2)_{0-2}C(O)OH$, —$(CH_2)_{0-2}C(O)OR^●$, —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —$SiR^●_3$, —$OSiR^●_3$, —C(O)$SR^●$, —$(C_{1-4}$ straight or branched alkylene)C(O)O$R^●$, or —$SSR^●$ wherein each $R^●$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O ("oxo"), =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —$R^●$, -(halo$R^●$), —OH, —O$R^●$, —O(halo$R^●$), —CN, —C(O)OH, —C(O)O$R^●$, —$NH_2$, —NH$R^●$, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N+(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, Ring A(R$^2$)(R$^3$), of a provided compound comprises one or more deuterium atoms.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof. Inhibition of activity of a protein kinase, for example, MK2 or a mutant thereof, in a biological sample is useful for a variety of purposes that are known to one of skill in the art. Examples of such purposes include, but are not limited to, blood transfusion, organ transplantation, biological specimen storage, and biological assays.

As used herein, a "disease or disorder associated with MK2" or, alternatively, "an MK2-mediated disease or disorder" means any disease or other deleterious condition in which MK2, or a mutant thereof, is known or suspected to play a role.

The term "subject", as used herein, means a mammal and includes human and animal subjects, such as domestic animals (e.g., horses, dogs, cats, etc.). The terms "subject" and "patient" are used interchangeably. In some embodiments, the "patient" or "subject" means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The amount of compounds of the present invention that may be combined with the carrier materials to produce a composition in a single dosage form will vary depending upon the host treated, the particular mode of administration, etc. Preferably, provided compositions are formulated so that a dosage of between 0.01 to about 100 mg/kg, or about 0.1 mg/kg to about 50 mg/kg, and preferably from about 1 mg/kg to about 25 mg/kg, of subject body weight/day of the inhibitor can be administered to a patient receiving these compositions to obtain the desired therapeutic effect. The amount of a compound of the present invention in the composition will also depend upon the particular compound in the composition.

The expression "unit dosage form" as used herein refers to a physically discrete unit of a provided compound and/or compositions thereof appropriate for the subject to be treated. It will be understood, however, that the total daily usage of the active agent (i.e., compounds and compositions of the present invention) will be decided by the attending physician within the scope of sound medical judgment. The specific effective dose level for any particular subject (i.e., patient) or organism will depend upon a variety of factors including the disorder being treated and the severity of the disorder; activity of specific active agent employed; specific composition employed; age, body weight, general health, sex and diet of the subject; time of administration, route of administration, and rate of excretion of the specific active agent employed; duration of the treatment; and like factors well known in the medical arts.

The term "parenteral" as used herein includes subcutaneous, intravenous, intramuscular, intra-articular, intra-synovial, intrasternal, intrathecal, intrahepatic, intralesional and intracranial injection or infusion techniques.

As used herein, a "therapeutically effective amount" means an amount of a substance (e.g., a therapeutic agent, composition, and/or formulation) that elicits a desired biological response. In some embodiments, a therapeutically effective amount of a substance is an amount that is sufficient, when administered as part of a dosing regimen to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of a provided compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a "therapeutically effective amount" is at least a minimal amount of a provided compound, or composition containing a provided compound, which is sufficient for treating one or more symptoms of an MK2-mediated disease or disorder.

As used herein, the terms "treatment," "treat," and "treating" refer to partially or completely alleviating, inhibiting, delaying onset of, preventing, ameliorating and/or relieving a disorder or condition, or one or more symptoms of the disorder or condition, as described herein. In some embodiments, treatment may be administered after one or more symptoms have developed. In some embodiments, the term "treating" includes preventing or halting the progression of a disease or disorder. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence. Thus, in some embodiments, the term "treating" includes preventing relapse or recurrence of a disease or disorder.

As used herein, the term "inhibitor" is defined as a compound that binds to and/or inhibits the target protein kinase, MK2, with measurable affinity. In certain embodiments, an inhibitor has an $IC_{50}$ and/or binding constant of less than about 50 μM, less than about 1 μM, less than about 500 nM, less than about 100 nM, or less than about 10 nM.

The terms "measurable affinity" and "measurably inhibit," as used herein, means a measurable change in MK2 activity between a sample comprising a compound of the present invention, or composition thereof, and MK2, and an equivalent sample comprising MK2, in the absence of said compound, or composition thereof.

As used herein, the term "irreversible" or "irreversible inhibitor" refers to an inhibitor (i.e. a compound) that is able to be covalently bonded to a kinase in a substantially non-reversible manner. That is, whereas a reversible inhibitor is able to bind to (but is generally unable to form a covalent bond with) a kinase, and therefore can become dissociated from the kinase, an irreversible inhibitor will remain substantially bound to a kinase once covalent bond formation has occurred. Irreversible inhibitors usually display time dependency, whereby the degree of inhibition increases with the time with which the inhibitor is in contact with the enzyme. In certain embodiments, an irreversible inhibitor will remain substantially bound to a kinase once covalent bond formation has occurred and will remain bound for a time period that is longer than the life of the protein.

Methods for identifying if a compound is acting as an irreversible inhibitor are known to one of ordinary skill in the art. Such methods include, but are not limited to, enzyme kinetic analysis of the inhibition profile of the compound with a kinase, the use of mass spectrometry of the protein drug target modified in the presence of the inhibitor compound, discontinuous exposure, also known as "washout," experiments, and the use of labeling, such as radiolabelled inhibitor, to show covalent modification of the enzyme, as well as other methods known to one of skill in the art.

As used herein, the term "drug resistance" refers to changes in the wild-type nucleic acid sequence coding a target protein, and/or the amino acid sequence of the target protein, and/or the amino acid sequence of another protein, which changes decrease or abolish the inhibitory effect of the inhibitor on the target protein. Without wishing to be bound by any particular theory, it is believed that certain compounds of the present invention, i.e., compounds that are irreversible kinase inhibitors, may be effective inhibitors of drug resistant forms of protein kinases.

3. Description of Exemplary Embodiments

As described herein, the present invention provides irreversible inhibitors of MK2 kinase. Without wishing to be bound by any particular theory, it is believed that compounds of the invention comprise a moiety capable of covalently binding to a key cysteine residue in the binding domain of MK2 kinase. Such a moiety is referred to herein as a "reactive moiety." One of ordinary skill in the art will appreciate that MK2 kinase, and mutants thereof, have a cysteine residue in the binding domain. Without wishing to be bound by any particular theory, it is believed that proximity of a reactive moiety, present on a provided MK2 inhibitor, to the cysteine of interest facilitates covalent modification of that cysteine by the reactive moiety.

The cysteine residues of interest can also be described by an identifying portion of the amino acid sequence of MK2 kinase which includes the cysteine of interest. Thus, in certain embodiments, Cys140 of MK2 is characterized in that Cys140 is the cysteine embedded in the following amino acid sequence of MK2:

```
SEQ ID NO. 1:
MLSNSQGQSPPVPFPAPAPPPQPPTPALPHPPAQPPPPPPQQFPQFHVKS

GLQIKKNAIIDDYKVTSQVLGLGINGKVLQIFNKRTQEKFALKMLQDCPK

ARREVELHWRASQCPHIVRIVDVYENLYAGRKCLLIVMECLDGGELFSRI

QDRGDQAFTEREASEIMKSIGEAIQYLHSINIAHRDVKPENLLYTSKRPN

AILKLTDFGFAKETTSHNSLTTPCYTPYYVAPEVLGPEKYDKSCDMWSLG

VIIVIYILLCGYPPFYSNHGLAISPGMKTRIRMGQYEFPNPEWSEVSEEV

KMLIRNLLKTEPTQRMTITEFMNHPWIMQSTKVPQTPLHTSRVLKEDKER

WEDVKEEMTSALATMRVDYEQIKIKKIEDASNPLLLKRRKKARALEAAAL

AH.
```

For the purpose of clarity, Cys410 is provided in the abbreviated amino acid sequence below:

```
SEQ ID NO. 2:
NLYAGRKCLLIVMEC(140)LDGGELFSRIQDR.
```

In both SEQ ID NOS. 1 and 2, Cysteine 140 is highlighted in bold with underlining.

In some embodiments, compounds of the present invention include a reactive moiety characterized in that provided compounds covalently modify Cys140 of MK2.

In certain embodiments, compounds of the present invention include a reactive moiety characterized in that a compound covalently modifies a target of Cys140 of MK2, thereby irreversibly inhibiting the kinase.

Thus, in some embodiments, a reactive moiety present on a provided MK2 inhibitor compound is capable of covalently binding to a cysteine residue thereby irreversibly inhibiting the enzyme. In some embodiments, the cysteine residue is Cys140 of MK2. One of ordinary skill in the art will recognize that a variety of reactive moieties, as defined herein, are suitable for such covalent bonding. Such reactive moieties include, but are not limited to, those described herein and depicted infra.

According to one aspect, the present invention provides a compound of formula I,

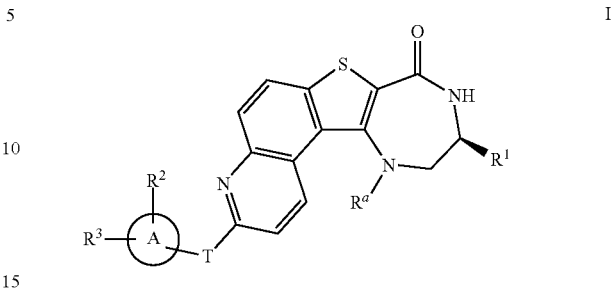

or a pharmaceutically acceptable salt thereof, wherein:

Ring A is phenyl, a 5-6 membered monocyclic heteroaryl ring having 1-3 nitrogens, or an 8-14 membered bicyclic heteroaryl ring having 1-4 heteroatoms independently selected from nitrogen, oxygen, and sulfur;

T is a bivalent moiety selected from —N(R)—, —O—, —S—, —S(O)—, —SO$_2$—, —C(S)—, —Si(R$^4$)$_2$—, —P(R$^5$)—, —P(O)$_2$—, or a bivalent saturated straight or branched 1-3 membered hydrocarbon chain, wherein the hydrocarbon chain is optionally substituted with oxo or —OR;

each R is independently hydrogen or an optionally substituted C$_{1-6}$ aliphatic, or:

two R groups on the same nitrogen are taken together with the nitrogen to form a 3-7 membered saturated or partially unsaturated heterocyclic ring having 1-3 heteroatoms selected from nitrogen, oxygen, or sulfur;

R$^a$ is hydrogen or an optionally substituted C$_{1-6}$ aliphatic;

R$^1$ is —R or —(CH$_2$)$_p$R$^x$;

p is 0, 1, 2, or 3;

R$^x$ is —CN, —NO$_2$, halogen, —OR, —SR, —N(R)$_2$, —C(O)N(R)$_2$, —C(O)OR, —C(O)R, —N(R)C(O)R, —SO$_2$N(R)$_2$, or —N(R)SO$_2$;

R$^2$ is halogen, —CN, —SR$^y$, —S(O)R$^y$, —SO$_2$R$^y$, —OSO$_2$R, —OC(O)R$^y$, or —OP(O)$_2$OR$^y$;

each R$^y$ is independently selected from optionally substituted C$_{1-6}$ aliphatic or optionally substituted phenyl;

R$^3$ is hydrogen, optionally substituted C$_{1-6}$ aliphatic, —CN, —NO$_2$, halogen, —OR, —N(R)$_2$, —C(O)N(R)$_2$, —C(O)OR, -Cy, —C(O)N(R)-Cy, —C(O)—Cy, —O-Cy, —O—(CH$_2$)$_n$-Cy, —(CH$_2$)$_n$—O-Cy, —(CH$_2$)$_m$N(R)$_2$, —(CH$_2$)$_m$OR, —N(R)—Cy, —N(R)—(CH$_2$)$_n$-Cy, —(CH$_2$)$_n$—N(R)-Cy, or —(CH$_2$)$_m$-Cy;

each R$^4$ is independently hydrogen, —OR, C$_{1-6}$ aliphatic, phenyl, or a 5-6 membered heteroaryl ring having 1-3 heteroatoms independently selected from nitrogen, oxygen, and sulfur;

each R$^5$ is independently —OR, C$_{1-6}$ aliphatic, phenyl, or a 5-6 membered heteroaryl ring having 1-3 heteroatoms independently selected from nitrogen, oxygen, and sulfur;

each of m and n is independently 0-4; and each Cy is independently an optionally substituted ring selected from a 3-9 membered saturated or partially unsaturated monocyclic carbocyclic ring, a 3-9 membered saturated or partially unsaturated monocyclic heterocyclic ring having 1-3 heteroatoms independently selected from nitrogen, oxygen, and sulfur, phenyl, a 5-6 membered heteroaryl ring having 1-3 heteroatoms independently selected from nitrogen, oxygen, and sulfur, a 7-12 membered saturated or partially unsaturated fused or bridged bicyclic carbocyclic ring, or a 6-12 membered saturated or partially unsaturated fused or bridged bicyclic heterocyclic ring having 1-3 heteroatoms independently selected from nitrogen, oxygen, and sulfur.

As defined generally above and discussed throughout, each $R°$ is independently hydrogen, $C_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur; wherein $R°$ may be substituted by halogen, —(CH$_2$)$_{0-2}$R$^†$, -(haloR$^†$), —(CH$_2$)$_{0-2}$OH, —(CH$_2$)$_{0-2}$OR$^●$, —(CH$_2$)$_{0-2}$CH(OR$^†$)$_2$; —O(haloR$^†$), —CN, —N$_3$, —(CH$_2$)$_{0-2}$C(O)R$^†$, —(CH$_2$)$_{0-2}$C(O)OH, —(CH$_2$)$_{0-2}$C(O)OR$^†$, —(CH$_2$)$_{0-2}$SR$^†$, —(CH$_2$)$_{0-2}$SH, —(CH$_2$)$_{0-2}$NH$_2$, —(CH$_2$)$_{0-2}$NHR$^†$, —(CH$_2$)$_{0-2}$NR$^†_2$, —NO$_2$, —SiR$^†_3$, —OSiR$^†_3$, —C(O)SR$^†$, —(C$_{1-4}$ straight or branched alkylene)C(O)OR$^†$, or —SSR$^†$; or two independent occurrences of $R^●$ may be optionally taken together with their intervening atom(s), form a 3-12-membered saturated, partially unsaturated, or aryl mono- or bicyclic ring having 0-4 heteroatoms independently selected from nitrogen, oxygen, or sulfur. In some such embodiments, each $R^●$ is unsubstituted or where preceded by "halo" is substituted only with one or more halogens, and is independently selected from $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As defined generally above, T is a bivalent moiety selected from —N(R)—, —O—, —S—, —S(O)—, —SO$_2$—, —C(S)—, —Si(R$^4$)$_2$—, —P(R$^5$)—, —P(O)$_2$—, or a bivalent saturated straight or branched 1-3 membered hydrocarbon chain, wherein the hydrocarbon chain is optionally substituted with oxo or —OR, wherein each R is independently hydrogen or an optionally substituted $C_{1-6}$ aliphatic. In some embodiments, T is —N(R)—, —O—, or —S—. In some embodiments, T is —NH—. In other embodiments, T is —O—. In other embodiments, T is —S—. In some embodiments, T is —N(R)— wherein R is optionally substituted $C_{1-6}$ aliphatic. In some embodiments, T is —N(CH$_3$)—. In some embodiments, T is —N(R)— wherein R is $C_{1-6}$ aliphatic optionally substituted with —(CH$_2$)$_{0-4}$N(R°)$_2$ or —(CH$_2$)$_{0-4}$OR°. In some such embodiments, R° is as defined above and described herein. In some embodiments, T is —N(R)— wherein R is $C_{1-6}$ aliphatic optionally substituted with —(CH$_2$)$_{0-4}$N(R°)$_2$ or —(CH$_2$)$_{0-4}$R°, wherein R° is hydrogen or $C_{1-6}$ aliphatic. In some embodiments, T is —N(CH$_2$CH$_2$N(R°)$_2$)— or —N(CH$_2$CH$_2$OR°)—, wherein R° is hydrogen or $C_{1-6}$ aliphatic. In certain embodiments, T is selected from the T moieties present on the compounds depicted in Table 1, below.

In some embodiments, T is a bivalent moiety selected from —N(R)—, —O—, —S—, —S(O)—, —SO$_2$—, —C(S)—, —Si(R$^4$)$_2$—, —P(R$^5$)—, —P(O)$_2$—, a bivalent 3-7 membered cycloalkylene, or a bivalent saturated straight or branched 1-3 membered hydrocarbon chain, wherein the hydrocarbon chain is optionally substituted with halogen, —R, deuterium, oxo, or —OR, wherein each R is independently hydrogen or an optionally substituted $C_{1-6}$ aliphatic. In some embodiments, T is a bivalent 3-7 membered cycloalkylene, or a bivalent saturated straight or branched 1-3 membered hydrocarbon chain, wherein the hydrocarbon chain is optionally substituted with halogen, —R, deuterium, oxo, or —OR, wherein each R is independently hydrogen or an optionally substituted $C_{1-6}$ aliphatic. In some embodiments, T is a bivalent 3-7 membered cycloalkylene. In some embodiments, T is cyclopropylene. In some embodiments, T is 1,1-cyclopropylene. In some embodiments, T is a bivalent saturated straight or branched 1-3 membered hydrocarbon chain, wherein the hydrocarbon chain is optionally substituted with halogen, —R, deuterium, oxo, or —OR, wherein each R is independently hydrogen or an optionally substituted $C_{1-6}$ aliphatic. In some embodiments, T is —CF$_2$—, —C(Me)$_2$-, or —CD$_2$-.

As defined generally above, $R^a$ is hydrogen or an optionally substituted $C_{1-6}$ aliphatic. In some embodiments, $R^a$ is hydrogen. In some embodiments, $R^a$ is an optionally substituted $C_{1-6}$ aliphatic. In some embodiments, $R^a$ is methyl.

As defined generally above, $R^1$ is —R or —(CH$_2$)$_p$R$^x$, wherein p is 0, 1, 2, or 3, and R$^x$ is —CN, —NO$_2$, halogen, —OR, —SR, —N(R)$_2$, —C(O)N(R)$_2$, —C(O)OR, —C(O)R, —N(R)C(O)R, —SO$_2$N(R)$_2$, or —N(R)SO$_2$. In certain embodiments, $R^1$ is —R, —CH$_2$OR, or —CH$_2$N(R)$_2$.

In some embodiments, $R^1$ is —R, wherein —R is optionally substituted $C_{1-6}$ aliphatic. In some embodiments, $R^1$ is methyl. In some embodiments, $R^1$ is —CH$_2$R$^x$, wherein R$^x$ is —OR or —N(R)$_2$. In certain embodiments, $R^1$ is —CH$_2$OCH$_3$. In some embodiments, $R^1$ is —CH$_2$NH$_2$. In some embodiments, $R^1$ is —CH$_2$NHCH$_3$. In some embodiments, $R^1$ is —CH$_2$N(CH$_3$)$_2$. In certain embodiments, $R^1$ is —CH$_2$OH. In certain embodiments, $R^1$ is selected from the $R^1$ moieties present on the compounds depicted in Table 1, below.

As defined generally above, Ring A is phenyl or a 5-6 membered heteroaryl ring having 1-3 nitrogens. In some embodiments, Ring A is phenyl or a 5-6 membered monocyclic heteroaryl ring having 1-3 nitrogens, or a 8-14 membered bicyclic heteroaryl ring having 1-4 heteroatoms independently selected from nitrogen, oxygen, and sulfur. In some embodiments, Ring A is phenyl. In some embodiments, Ring A is a 5-6 membered heteroaryl ring having 1-3 nitrogens. In some embodiments, Ring A is a 8-14 bicyclic heteroaryl ring having 1-4 heteroatoms independently selected from nitrogen, oxygen, and sulfur.

In certain embodiments, Ring A is phenyl and $R^3$ is an electron withdrawing group. One of ordinary skill in the art would recognize that certain moieties encompassed by the definition of $R^3$ are electron withdrawing groups. Thus, in some embodiments, Ring A is phenyl and $R^3$ is selected from —CN, —NO$_2$, halogen, —C(O)N(R)$_2$, —C(O)OR, -Cy, —C(O)N(R)-Cy, or —C(O)—Cy. In some embodiments, Ring A is phenyl and $R^3$ is selected from —CN, halogen, —C(O)N(R)$_2$, —C(O)OR, -Cy, —C(O)N(R)-Cy, or —C(O)—Cy. In certain embodiments, Ring A is phenyl and $R^3$ is hydrogen, optionally substituted $C_{1-6}$ aliphatic, —CN, —NO$_2$, halogen, —OR, —N(R)$_2$, —C(O)N(R)$_2$, —C(O)OR, -Cy, —C(O)N(R)-Cy, —C(O)—Cy, —O-Cy, —O—(CH$_2$)$_n$-Cy, —(CH$_2$)$_n$—O-Cy, —N(R)—Cy, —N(R)—(CH$_2$)$_n$-Cy, —(CH$_2$)$_n$—N(R)-Cy, or —(CH$_2$)$_m$-Cy. In certain embodiments, Ring A is phenyl and $R^3$ is hydrogen, optionally substituted $C_{1-6}$ aliphatic, —CN, halogen, —OR, —N(R)$_2$, —C(O)N(R)$_2$, —C(O)OR, -Cy, —C(O)N(R)-Cy, —C(O)—Cy, —O-Cy, —O—(CH$_2$)$_n$-Cy, —(CH$_2$)$_n$—O-Cy, —N(R)—Cy, —N(R)—(CH$_2$)$_n$-Cy, —(CH$_2$)$_n$—N(R)-Cy, or —(CH$_2$)$_m$-Cy. In certain embodiments, Ring A is phenyl and $R^3$ is selected from —CN, —NO$_2$, or halogen. In certain embodiments, Ring A is phenyl and $R^3$ is selected from —CN or halogen.

In some embodiments, Ring A is phenyl and $R^2$ is at a meta position of the phenyl ring and $R^3$ is at an ortho position of the phenyl ring. In some embodiments, Ring A is:

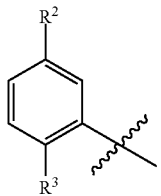

wherein $R^2$ is as defined above and herein and $R^3$ is an electron withdrawing group and wherein the wavy line indicates the point of attachment of Ring A to T.

In some embodiments, Ring A is:

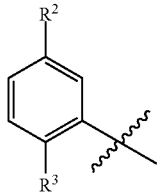

wherein $R^2$ is halogen and $R^3$ is —CN and wherein the wavy line indicates the point of attachment of Ring A to T.

In some embodiments, Ring A is

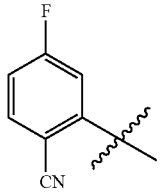 [SMILES: *c1cc(F)ccc1C#N]

wherein the wavy line indicates the point of attachment of Ring A to T.

In some embodiments, Ring A is a 5-6-membered heteroaryl ring having 1-3 nitrogens. In some embodiments, Ring A is a 5-membered heteroaryl ring having 1-3 nitrogens. In some embodiments, Ring A is a 6-membered heteroaryl ring having 1-3 nitrogens. In some embodiments, Ring A is pyridyl. In some embodiments, Ring A is pyrimidinyl. In some embodiments, Ring A is pyridazinyl. In some embodiments, Ring A is pyrazinyl. In some embodiments Ring A is triazinyl.

In some embodiments, Ring A is a 8-14 membered bicyclic heteroaryl ring having 1-4 heteroatoms independently selected from nitrogen, oxygen, and sulfur. In some embodiments, Ring A is a 9-10 membered bicyclic heteroaryl ring having 1-4 heteroatoms independently selected from nitrogen, oxygen, and sulfur. In some embodiments, Ring A is a 9-10 membered bicyclic heteroaryl ring having 2-3 heteroatoms independently selected from nitrogen, oxygen, and sulfur. In some embodiments, Ring A is selected from:

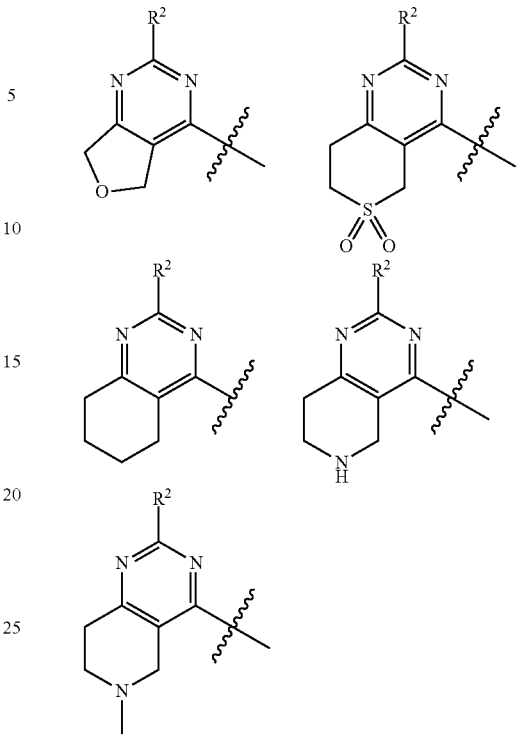

As defined generally above, $R^2$ is halogen, —CN, —$SR^y$, —$S(O)R^y$, —$SO_2R^y$, —$OSO_2R^y$, —$OC(O)R^y$, or —$OP(O)_2OR^y$, wherein each $R^y$ is independently selected from optionally substituted $C_{1-6}$ aliphatic or optionally substituted phenyl. One of ordinary skill in the art will recognize that moieties encompassed by the definition of $R^2$ are leaving groups. Leaving groups are well known in the art, e.g., see, "Advanced Organic Chemistry," Jerry March, 4$^{th}$ Ed., pp. 351-357, John Wiley and Sons, N.Y. (1992). In some embodiments, $R^2$ is halogen. In some embodiments, $R^2$ is fluoro. In certain embodiments, $R^2$ is chloro. In some embodiments, $R^2$ is —$SR^y$ or —$SO_2R^y$. In some embodiments, $R^2$ is —SR or —$SO_2R^y$ and $R^y$ is optionally substituted $C_{1-6}$ aliphatic. In some embodiments, $R^2$ is —$SCH_3$ or —$SO_2CH_3$. In some embodiments, $R^2$ is selected from the $R^2$ moieties present on the compounds depicted in Table 1, below.

As defined generally above, $R^3$ is hydrogen, optionally substituted $C_{1-6}$ aliphatic, —CN, —$NO_2$, halogen, —OR, —$N(R)_2$, —$C(O)N(R)_2$, —C(O)OR, -Cy, —C(O)N(R)-Cy, —C(O)—Cy, —O-Cy, —O—$(CH_2)_n$-Cy, —$(CH_2)_n$—O-Cy, —$(CH_2)_m N(R)_2$, —$(CH_2)_m$OR, —N(R)—Cy, —N(R)—$(CH_2)_n$-Cy, —$(CH_2)_n$—N(R)-Cy, or —$(CH_2)_m$-Cy wherein each m and n is independently 0, 1, 2, 3, or 4, and each Cy is independently an optionally substituted ring selected from a 3-9 membered saturated or partially unsaturated carbocyclic ring or a 3-9 membered saturated or partially unsaturated heterocyclic ring having 1-3 heteroatoms independently selected from nitrogen, oxygen, and sulfur, phenyl, a 5-6 membered heteroaryl ring having 1-3 heteroatoms independently selected from nitrogen, oxygen, and sulfur, a 7-12 membered saturated or partially unsaturated fused or bridged bicyclic carbocyclic ring, or a 7-12 membered saturated or partially unsaturated fused or bridged bicyclic heterocyclic ring having 1-3 heteroatoms independently selected from nitrogen, oxygen, and sulfur.

In some embodiments, Cy is an optionally substituted 3-9 membered saturated or partially unsaturated carbocyclic ring. In some embodiments, Cy is an optionally substituted 3-7 membered saturated or partially unsaturated carbocyclic ring. In some embodiments, Cy is an optionally substituted 3-7 membered saturated carbocyclic ring. In some embodiments, Cy is an optionally substituted cyclopropyl or cyclohexyl ring.

In some embodiments, Cy is an optionally substituted 3-9 membered saturated or partially unsaturated heterocyclic ring having 1-3 heteroatoms independently selected from nitrogen, oxygen, and sulfur. In some embodiments, Cy is an optionally substituted 3-7 membered saturated or partially unsaturated heterocyclic ring having 1-3 heteroatoms independently selected from nitrogen, oxygen, and sulfur. In some embodiments, Cy is an optionally substituted 5-6 membered saturated or partially unsaturated monocyclic heterocyclic ring having 1-3 heteroatoms independently selected from nitrogen, oxygen, and sulfur.

In some embodiments, Cy is an optionally substituted 4-6 membered saturated heterocyclic ring having 1-3 heteroatoms independently selected from nitrogen, oxygen, and sulfur. In some embodiments, Cy is an optionally substituted 4-membered saturated heterocyclic ring having 1 heteroatom selected from nitrogen, oxygen, and sulfur. In some embodiments, Cy is an optionally substituted 5-membered saturated heterocyclic ring having 1-2 heteroatoms independently selected from nitrogen, oxygen, and sulfur. In some embodiments, Cy is an optionally substituted 6-membered saturated heterocyclic ring having 1-3 heteroatoms independently selected from nitrogen, oxygen, and sulfur. In certain embodiments, Cy is an optionally substituted group selected from oxetanyl, tetrahydrofuranyl, pyrrolidinyl, tetrahydropyranyl, piperidinyl, piperazinyl, and morpholinyl.

In some embodiments, Cy is an optionally substituted 3-7 membered partially unsaturated heterocyclic ring having 1-3 heteroatoms independently selected from nitrogen, oxygen, and sulfur. In some such embodiments, Cy is 3,6-dihydro-2H-pyranyl or 1,2,3,6-tetrahydropyridinyl.

In some embodiments, Cy is optionally substituted phenyl.

In some embodiments, Cy is an optionally substituted 5-6 membered heteroaryl ring having 1-3 heteroatoms independently selected from nitrogen, oxygen, and sulfur. In some embodiments, Cy is optionally substituted pyridyl.

In some embodiments, Cy is an optionally substituted 7-12 membered saturated or partially unsaturated fused or bridged bicyclic carbocyclic ring.

In some embodiments, Cy is an optionally substituted 7-12 membered saturated or partially unsaturated fused or bridged bicyclic heterocyclic ring having 1-3 heteroatoms independently selected from nitrogen, oxygen, and sulfur. In some embodiments, Cy is an optionally substituted 8-membered saturated bridged bicyclic heterocyclic ring having 1-3 heteroatoms independently selected from nitrogen, oxygen, and sulfur. In some such embodiments, Cy is (1R,5S)-3-oxa-8-azabicyclo[3.2.1]octyl (i.e., a moiety having the structure

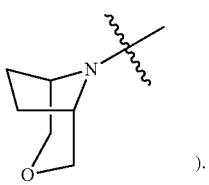 [SMILES: *N1C2CCC1COC2]
).

In some embodiments, a substitutable carbon atom of Cy is optionally substituted with halogen, —(CH$_2$)$_{0-4}$R°, —(CH$_2$)$_{0-4}$OR°, —(CH$_2$)$_{0-4}$N(R°)$_2$, wherein:
R° is hydrogen or C$_{1-6}$ aliphatic optionally substituted with halogen or —(CH$_2$)$_{0-2}$OR●, and
R● is C$_{1-4}$ aliphatic; or:
two independent occurrences of R°, taken together with their intervening atom(s), form a 3-6 membered ring saturated ring having 0-1 heteroatoms selected from nitrogen, oxygen or sulfur.

In some embodiments, a substitutable nitrogen atom of Cy is optionally substituted with —(CH$_2$)$_{0-4}$R†, wherein R† is hydrogen or C$_{1-6}$ aliphatic.

In some embodiments, Cy is

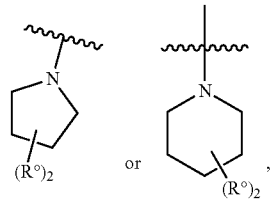

wherein each R° is C$_{1-6}$ aliphatic. In some embodiments, Cy is

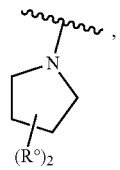

wherein each R° is C$_{1-6}$ aliphatic and the two occurrences of R°, taken together with their intervening atom(s), form a 3-4 membered ring saturated ring having 0-1 heteroatoms selected from nitrogen, oxygen or sulfur. In some such embodiments, Cy is 3-azabicyclo[3.1.0]hexyl (i.e., a moiety having the structure

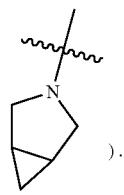
).

In some embodiments, Cy is

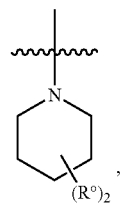

wherein each R° is C$_{1-6}$ aliphatic and the two occurrences of R°, taken together with their intervening atom(s), form a 3-4 membered ring saturated ring having 0-1 heteroatoms selected from nitrogen, oxygen or sulfur. In some such embodiments, Cy is 3-azabicyclo[3.1.1]heptyl (i.e., a moiety having the structure

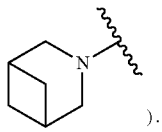
).

In certain embodiments, Cy is selected from:

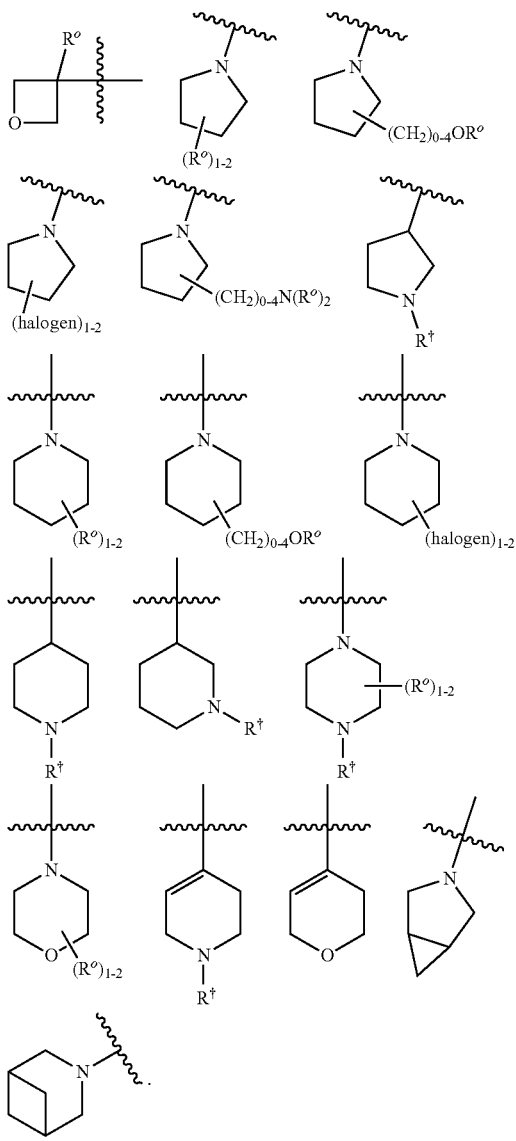

One of ordinary skill in the art would recognize that the definition of $R^3$ includes electron-withdrawing groups (e.g., —CN, —NO$_2$, halogen, etc.) and solubilizing groups (e.g., —N(R)$_2$, -Cy, —C(O)N(R)-Cy, —C(O)—Cy, —O-Cy, —O—(CH$_2$)$_n$-Cy, —(CH$_2$)$_n$—O-Cy, —(CH$_2$)$_m$N(R)$_2$, —(CH$_2$)$_m$OR, —N(R)—Cy, —N(R)—(CH$_2$)$_n$-Cy, —(CH$_2$)$_n$—N(R)-Cy, —(CH$_2$)$_m$-Cy, etc.). Thus, in some embodiments, $R^3$ is an electron-withdrawing group. In other embodiments, $R^3$ is a solubilizing group.

In some embodiments, $R^3$ is hydrogen. In some embodiments, $R^3$ is optionally substituted $C_{1-6}$ aliphatic, —CN, —NO$_2$, halogen, —OR, —N(R)$_2$, —C(O)N(R)$_2$, —C(O)OR, -Cy, —C(O)N(R)-Cy, —C(O)—Cy, —O-Cy, —O—(CH$_2$)$_n$-Cy, —(CH$_2$)$_n$—O-Cy, —(CH$_2$)$_m$N(R)$_2$, —(CH$_2$)$_m$OR, —N(R)—Cy, —N(R)—(CH$_2$)$_n$-Cy, —(CH$_2$)$_n$—N(R)-Cy, or —(CH$_2$)$_m$-Cy. In some embodiments, $R^3$ is optionally substituted $C_{1-6}$ aliphatic. In some embodiments, $R^3$ is —(CH$_2$)$_m$N(R)$_2$, —(CH$_2$)$_m$OR, —(CH$_2$)$_n$—O-Cy, —(CH$_2$)$_m$-Cy, —(CH$_2$)$_{0-4}$N(R°)$_2$, or —(CH$_2$)$_{0-4}$OR°. In some embodiments, $R^3$ is $C_{1-6}$ aliphatic optionally substituted with —(CH$_2$)$_{0-4}$N(R°)$_2$. In some such embodiments, R° is hydrogen or optionally substituted $C_{1-6}$ aliphatic. In some embodiments, $R^3$ is $C_{1-6}$ aliphatic optionally substituted with —(CH$_2$)$_{0-4}$SO$_2$R°, —(CH$_2$)$_{0-4}$OR° or —(CH$_2$)$_{0-4}$N(R°)$_2$, wherein R° is hydrogen or optionally substituted $C_{1-6}$ aliphatic. In some embodiments, $R^3$ is —(CH$_2$)$_{0-4}$OR°. In some embodiments, $R^3$ is —(CH$_2$)$_{0-4}$SO$_2$R°. In some embodiments, $R^3$ is —(CH$_2$)$_{0-4}$N(R°)$_2$. In some embodiments, $R^3$ is —(CH$_2$)$_{1-4}$N(R°)$_2$. In some embodiments, $R^3$ is —CH$_2$N(R°)$_2$. In some embodiments, $R^3$ is —CH$_2$N(R°)$_2$, —CH$_2$OR° or —CH$_2$SO$_2$R. In some such embodiments, R° is $C_{1-6}$ aliphatic optionally substituted with —CN, halogen or —(CH$_2$)$_{0-2}$OR$^\bullet$, wherein R$^\bullet$ is $C_{1-4}$ aliphatic. In some embodiments, $R^3$ is —CH$_2$OH, —CH$_2$OCH$_3$, —CH$_2$OCHF$_2$, —CH$_2$OCH$_2$CHF$_2$, —CH$_2$OCH$_2$CH$_3$, —CH$_2$OCD$_2$CD$_3$, —CH$_2$OCH$_2$CH$_2$F, —CH$_2$OCH$_2$CH$_2$CN, —CH$_2$OC(CH$_3$)$_3$, —CH$_2$SO$_2$CH$_3$, —CH$_2$NHC(CH$_3$)$_3$, —CH$_2$N(CH$_3$)C(CH$_3$)$_3$, —CH$_2$N(CH$_3$)CH(CH$_3$)$_2$, CH$_2$N(CH$_2$CH(CH$_3$)$_2$)$_2$, —CH$_2$N(CH$_3$)CH$_2$CH$_2$OCH$_3$, or —CH$_2$N(CH$_3$)CH$_2$CH$_2$OCH$_2$CH$_3$.

In some embodiments, $R^3$ is —(CH$_2$)$_m$N(R)$_2$ or —(CH$_2$)$_m$OR. In some embodiments, $R^3$ is —(CH$_2$)$_m$N(R)$_2$. In some such embodiments, $R^3$ is —CH$_2$N(R)$_2$. In some embodiments, $R^3$ is —CH$_2$NHC(CH$_3$)$_3$. In some embodiments, $R^3$ is —CH$_2$N(CH$_3$)C(CH$_3$)$_3$. In some embodiments, $R^3$ is —CH$_2$N(CH$_3$)CH(CH$_3$)$_2$. In some embodiments, $R^3$ is —CH$_2$N(CH$_2$CH(CH$_3$)$_2$)$_2$. In some embodiments, $R^3$ is —CH$_2$N(CH$_3$)CH$_2$CH$_2$OCH$_3$. In some embodiments, $R^3$ is —CH$_2$N(CH$_3$)CH$_2$CH$_2$OCH$_2$CH$_3$. In some such embodiments, $R^3$ is —CH$_2$OR. In some embodiments, $R^3$ is —CH$_2$OH. In some embodiments, $R^3$ is —CH$_2$OCH$_3$. In some embodiments, $R^3$ is —CH$_2$OCCH$_2$CH$_3$.

In some embodiments, $R^3$ is —(CH$_2$)$_m$-Cy, wherein Cy is defined as above and described herein.

In some embodiments, $R^3$ is —CH$_2$Cy, wherein Cy is an optionally substituted 5-6 membered saturated or partially unsaturated heterocyclic ring having 1-3 heteroatoms independently selected from nitrogen, oxygen, and sulfur.

In some embodiments, $R^3$ is —(CH$_2$)$_m$-Cy, wherein Cy is an optionally substituted 7-12 membered saturated or partially unsaturated fused or bridged bicyclic heterocyclic ring having 1-3 heteroatoms independently selected from nitrogen, oxygen, and sulfur.

In some embodiments, $R^3$ is -Cy. In some embodiments, $R^3$ is -Cy, wherein Cy is an optionally substituted 5-6 membered heteroaryl ring having 1-3 heteroatoms independently selected from nitrogen, oxygen, and sulfur. In some embodiments, $R^3$ is -Cy, wherein Cy is an optionally substituted 7-12 membered heteroaryl ring having 1-3 heteroatoms independently selected from nitrogen, oxygen, and sulfur. In some embodiments, $R^3$ is -Cy, wherein Cy is as defined above and described herein.

In some embodiments, $R^3$ is optionally substituted $C_{1-6}$ aliphatic selected from —CH$_2$OH, —CH$_2$OCH$_3$ and —CH$_3$.

In some embodiments, R³ is —OR, wherein R is optionally substituted C₁₋₆ aliphatic. In some embodiments, R³ is selected from —O(CH₂)₂OCH₃, —O(CH₂)₂N(CH₃)₂, and —OCH₃.

In some embodiments, R³ is —N(R)₂, wherein R is optionally substituted C₁₋₆ aliphatic. In some embodiments, R³ is —N(CH₃)₂.

In certain embodiments, R³ is halogen, —CN, NO₂, —C(O)N(R)₂, or —C(O)OR. In some embodiments, R³ is halogen, —CN, or NO₂. In some embodiments, R³ is fluoro, chloro or bromo. In certain embodiments, R³ is —C(O)N(R)₂ or —C(O)OR, wherein each R is as defined above and described herein. In certain embodiments, R³ is selected from —C(O)NH₂, —C(O)OCH₂CH₃, and —OC(O)CH₃. In certain embodiments, R³ is selected from —C(O)NH₂, —C(O)OCH₃, —C(O)OCH₂CH₃, and —OC(O)CH₃.

In certain embodiments, R³ is -Cy, —(CH₂)ₘ-Cy, —C(O)N(R)-Cy, —C(O)—Cy, —OR, —O-Cy, or —O—(CH₂)ₙ-Cy, wherein each of R, n, m, and -Cy is as defined above and described herein.

In some embodiments, R³ is -Cy, —(CH₂)ₘ-Cy, —C(O)N(R)-Cy, —C(O)—Cy, —O-Cy, or —O—(CH₂)ₙ-Cy, wherein each -Cy is independently an optionally substituted ring selected from a 3-7 membered saturated or partially unsaturated carbocyclic ring. In some embodiments, R³ is -Cy, —(CH₂)ₘ-Cy, —C(O)N(R)-Cy, —C(O)—Cy, —O-Cy, or —O—(CH₂)ₙ-Cy, wherein each -Cy is an optionally substituted cyclopropyl ring.

In some embodiments, R³ is -Cy, —(CH₂)ₘ-Cy, —C(O)N(R)-Cy, —C(O)—Cy, —O-Cy, or —O—(CH₂)ₙ-Cy, wherein each -Cy is independently an optionally substituted ring selected from a 4-7 membered saturated or partially unsaturated heterocyclic ring having 1-3 heteroatoms independently selected from nitrogen, oxygen, and sulfur. In some embodiments, R³ is-Cy, —(CH₂)ₘ-Cy, —C(O)N(R)-Cy, —C(O)—Cy, —O-Cy, or —O—(CH₂)ₙ-Cy, wherein each -Cy is independently an optionally substituted ring selected from oxetanyl, piperidinyl, pyrrolidinyl, tetrahydrofuranyl, piperazinyl, and morpholinyl. In some embodiments, R³ is -Cy, —(CH₂)ₘ-Cy, —C(O)N(R)-Cy, —C(O)—Cy, —O-Cy, or —O—(CH₂)ₙ-Cy, wherein each -Cy is independently an optionally substituted ring selected from oxetanyl, piperidinyl, pyrrolidinyl, tetrahydrofuranyl, tetrahydropyranyl, piperazinyl, and morpholinyl. In some embodiments, R³ is —(CH₂)ₘ-Cy or C₁₋₆ aliphatic substituted by —(CH₂)₀₋₄OR°. In some embodiments, R³ is —CH₂Cy or —CH₂OR. In some such embodiments, R° is as defined above and described herein. In some embodiments, R³ is —(CH₂)ₘ-Cy or —(CH₂)ₘOR. In some embodiments R³ is —CH₂Cy or —CH₂OR. In some embodiments R³ is —(CH₂)ₘ-Cy where Cy is optionally substituted piperidinyl.

As defined generally above, each of m and n is independently 0-4. In some embodiments, m is 1-2. In some embodiments, m is 1. In some embodiments, m is 2. In some embodiments, n is 1-2. In some embodiments, n is 1. In some embodiments, n is 2.

In some embodiments, R³ is selected from the R³ moieties present on the compounds depicted in Table 1, below.

In some embodiments, the present invention provides a compound of any one of formulas II, III, IV, V, or VI:

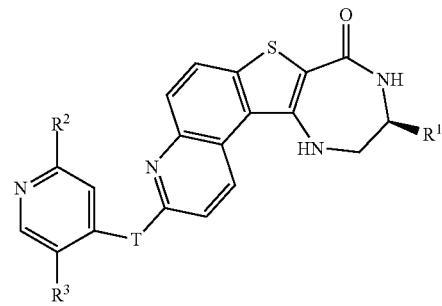

II

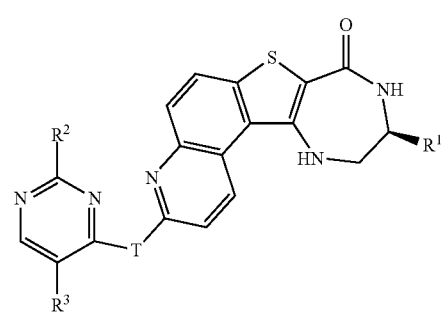

III

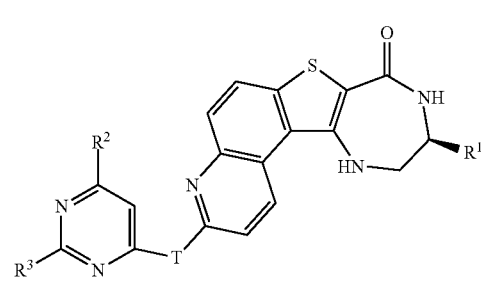

IV

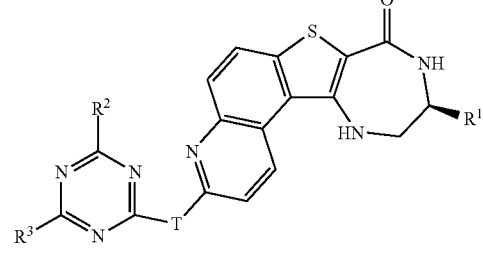

V

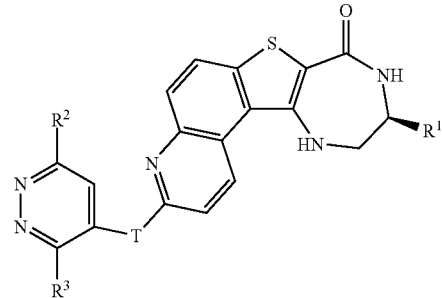

VI or a pharmaceutically acceptable salt thereof, wherein each of R¹, T, R², and R³ is as defined above and described herein.

In some embodiments, the present invention provides a compound of any one of formulas VII, VIII, IX, X, XI, or XII:

VII
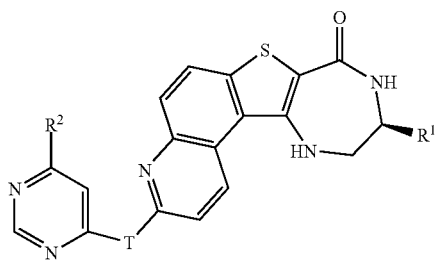
VIII
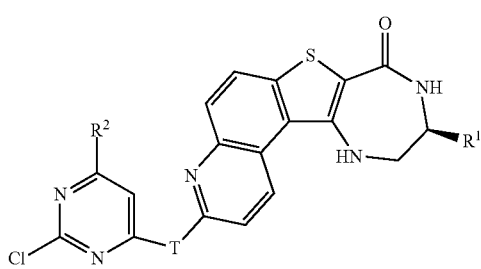
IX
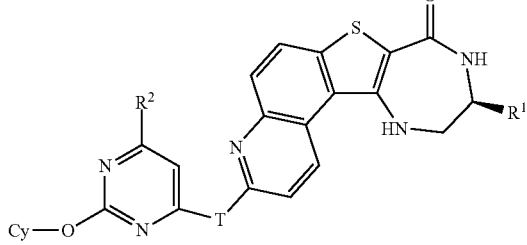
X
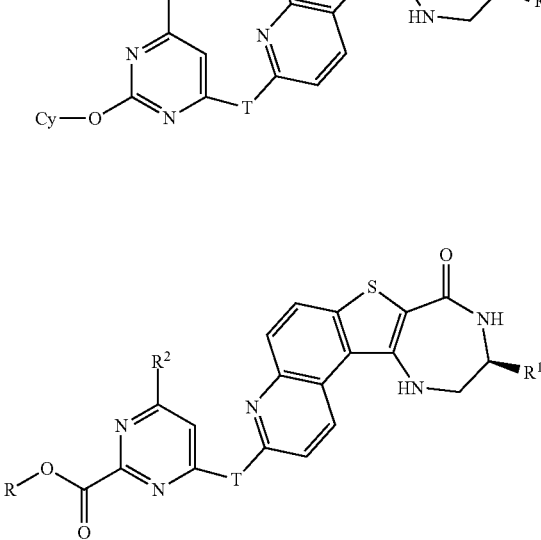
XI
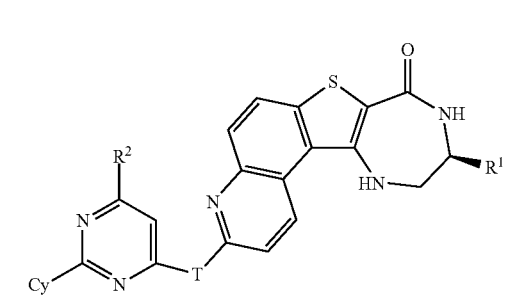
XII
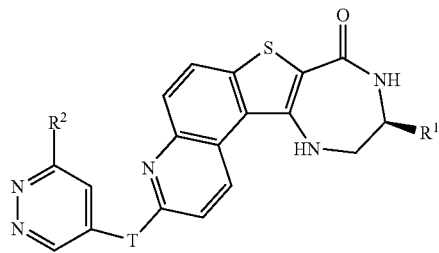
or a pharmaceutically acceptable salt thereof, wherein each of $R^1$, T, $R^2$, R, and -Cy is as defined above and described herein.
In some embodiments, the present invention provides a compound of any one of formulas XIII, XIV, XV, XVI, XVII, XVIII, XIX, XX, XXI, or XXII:
XIII
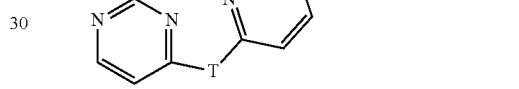
XIV
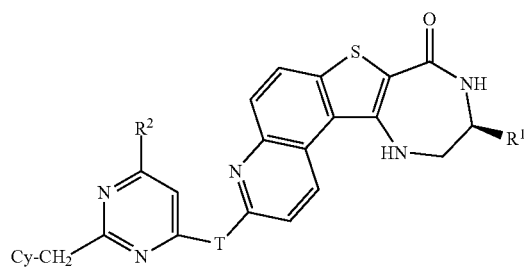
XVI
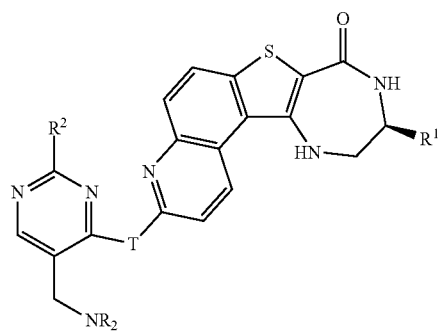

XVII
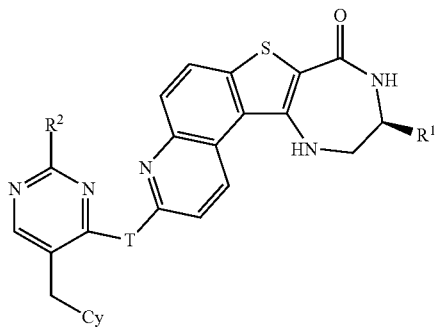
XVIII
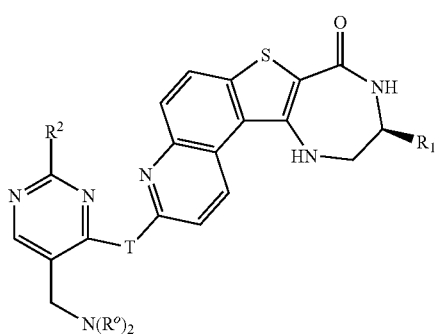
XIX
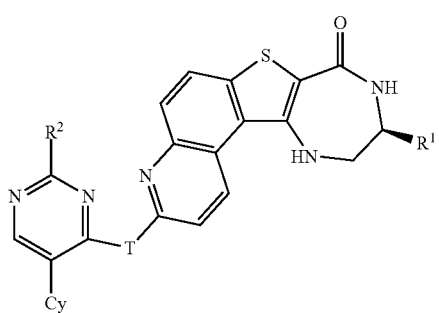
XX
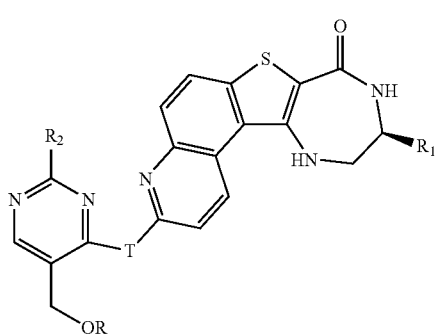
XXI
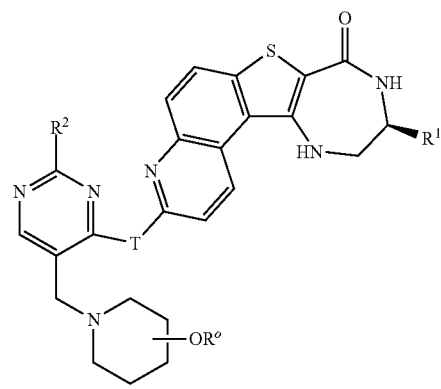
XXII
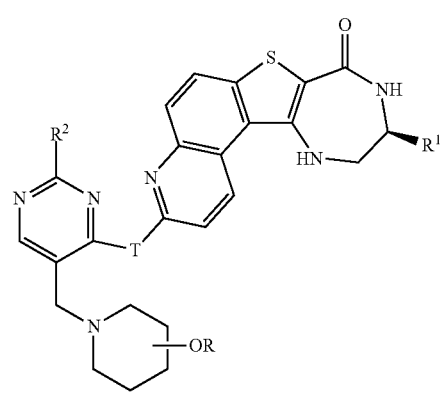
XXIII
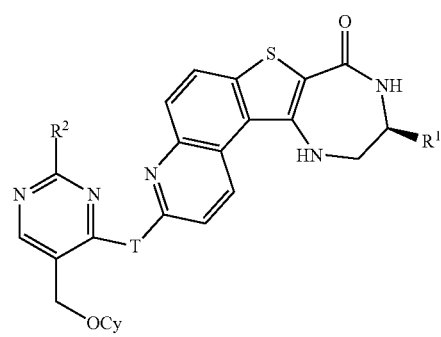
XXIV
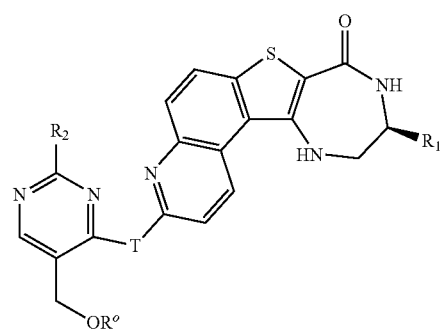
or a pharmaceutically acceptable salt thereof, wherein each of $R^1$, T, $R^2$, R, $R^o$, and -Cy is as defined above and described herein.
In some embodiments, the present invention provides a compound of any one of formulas XXV or XXVI:

XXV

XXVI

In certain embodiments, the present invention provides a compound of any one of formulas I through VI. In certain embodiments, the present invention provides a compound of any one of formulas VII through XIV. In certain embodiments, the present invention provides a compound of any one of formulas II, III, or IV. In certain embodiments, the present invention provides a compound of any one of formulas II, III, or V. In certain embodiments, the present invention provides a compound of any one of formulas II, IV, or V. In certain embodiments, the present invention provides a compound of any one of formulas III, IV, or V. In certain embodiments, the present invention provides a compound of any one of formulas III, IV, or VI. In certain embodiments, the present invention provides a compound of any one of formulas III, V, or VI. In certain embodiments, the present invention provides a compound of any one of formulas VII, VIII, IX, X, XII, XIII, or XIV. In certain embodiments, the present invention provides a compound of any one of formulas VII, VIII, IX, XII, XIII, or XIV. In certain embodiments, the present invention provides a compound of any one of formulas VII, IX, XII, XIII, or XIV. In certain embodiments, the present invention provides a compound of any one of formulas VIII, X, XI, or XIII. In certain embodiments, the present invention provides a compound of any one of formulas XX or XXI. In certain embodiments, the present invention provides a compound of any of of formulas XVII or XVIII. In certain embodiments, the present invention provides a compound of any one of formulas XXV or XXVI.

In certain embodiments, the present invention provides a compound of any one of formulas I through XXVI wherein T is —O—. In certain embodiments, the present invention provides a compound of any one of formulas I through XIV wherein T is —O—. In certain embodiments, the present invention provides a compound of any one of formulas I through VI wherein T is —O—. In certain embodiments, the present invention provides a compound of any one of formulas VII through XIV wherein T is —O—. In certain embodiments, the present invention provides a compound of any one of formulas II, III, or IV wherein T is —O—. In certain embodiments, the present invention provides a compound of any one of formulas II, III, or V wherein T is —O—. In certain embodiments, the present invention provides a compound of any one of formulas II, IV, or V wherein T is —O—. In certain embodiments, the present invention provides a compound of any one of formulas III, IV, or V wherein T is —O—. In certain embodiments, the present invention provides a compound of any one of formulas III, IV, or VI wherein T is —O—. In certain embodiments, the present invention provides a compound of any one of formulas III, V, or VI wherein T is —O—. In certain embodiments, the present invention provides a compound of any one of formulas VII, VIII, IX, X, XII, XIII, or XIV wherein T is —O—. In certain embodiments, the present invention provides a compound of any one of formulas VII, VIII, IX, XII, XIII, or XIV wherein T is —O—. In certain embodiments, the present invention provides a compound of any one of formulas VII, IX, XII, XIII, or XIV wherein T is —O—. In certain embodiments, the present invention provides a compound of any one of formulas VIII, X, XI, or XIII wherein T is —O—.

In certain embodiments, the present invention provides a compound of any one of formulas I through XXVI wherein T is —NH—. In certain embodiments, the present invention provides a compound of any one of formulas I through XIV wherein T is —NH—. In certain embodiments, the present invention provides a compound of any one of formulas I through VI wherein T is —NH—. In certain embodiments, the present invention provides a compound of any one of formulas VII through XIV wherein T is —NH—. In certain embodiments, the present invention provides a compound of any one of formulas II, III, or IV wherein T is —NH—. In certain embodiments, the present invention provides a compound of any one of formulas II, III, or V wherein T is —NH—. In certain embodiments, the present invention provides a compound of any one of formulas II, IV, or V wherein T is —NH—. In certain embodiments, the present invention provides a compound of any one of formulas III, IV, or V wherein T is —NH—. In certain embodiments, the present invention provides a compound of any one of formulas III, IV, or VI wherein T is —NH—. In certain embodiments, the present invention provides a compound of any one of formulas III, V, or VI wherein T is —NH—. In certain embodiments, the present invention provides a compound of any one of formulas VII, VIII, IX, X, XII, XIII, or XIV wherein T is —NH—. In certain embodiments, the present invention provides a compound of any one of formulas VII, VIII, IX, XII, XIII, or XIV wherein T is —NH—. In certain embodiments, the present invention provides a compound of any one of formulas VII, IX, XII, XIII, or XIV wherein T is —NH—. In certain embodiments, the present invention provides a compound of any one of formulas VIII, X, XI, or XIII wherein T is —NH—.

In certain embodiments, the present invention provides a compound of any one of formulas I through XXIV wherein $R^2$ is chloro or fluoro. In certain embodiments, the present invention provides a compound of any one of formulas I through XIV wherein $R^2$ is chloro or fluoro. In certain embodiments, the present invention provides a compound of any one of formulas I through VI wherein $R^2$ is chloro or fluoro. In certain embodiments, the present invention provides a compound of any one of formulas VII through XIV wherein $R^2$ is chloro or fluoro. In certain embodiments, the present invention provides a compound of any one of formulas II, III, or IV wherein $R^2$ is chloro or fluoro. In certain embodiments, the present invention provides a compound of any one of formulas II, III, or V wherein $R^2$ is chloro or fluoro. In certain embodiments, the present invention provides a compound of any one of formulas II, IV, or V wherein $R^2$ is chloro or fluoro. In certain embodiments, the present invention provides a compound of any one of formulas III, IV, or V wherein $R^2$ is chloro or fluoro. In certain embodiments, the present invention provides a compound of any one of formulas III, IV, or VI wherein $R^2$ is chloro or fluoro. In certain embodiments, the present invention provides a compound of any one of formulas III, V, or VI wherein $R^2$ is chloro or fluoro. In certain embodiments, the present invention provides a compound of any one of formulas VII, VIII, IX, X, XII, XIII, or XIV wherein $R^2$ is chloro or fluoro. In certain embodiments, the present invention provides a compound of any one of formulas VII, VIII, IX, XII, XIII, or XIV wherein $R^2$ is chloro or fluoro. In certain embodiments, the present invention provides a compound of any one of formulas VII, IX, XII, XIII, or XIV wherein $R^2$ is chloro or fluoro. In certain embodiments, the present invention provides a compound of any one of formulas VIII, X, XI, or XIII wherein $R^2$ is chloro or fluoro.

In certain embodiments, the present invention provides a compound of formula I or III, wherein $R^2$ is halogen. In certain embodiments, the present invention provides a compound of formula I or III, wherein $R^2$ is halogen.

In certain embodiments, the present invention provides a compound of formula I or III, wherein T is —O— and $R^2$ is halogen. In certain embodiments, the present invention provides a compound of formula I or III, wherein T is —O—, $R^2$ is halogen, and $R^3$ is —CH$_2$Cy. In certain embodiments, the present invention provides a compound of formula I or III, wherein T is —O—, $R^2$ is halogen, and $R^3$ is —(CH$_2$)$_m$Cy, —(CH$_2$)$_n$OCy, or C$_{1-6}$ aliphatic substituted by —(CH$_2$)$_{0-4}$N(R°)$_2$, or —(CH$_2$)$_{0-4}$OR°. In some such embodiments, R° is as defined above and described herein.

In certain embodiments, the present invention provides a compound of formula I wherein T is —O—, $R^2$ is halogen, and $R^3$ is —(CH$_2$)$_m$Cy, —(CH$_2$)$_n$OCy, —(CH$_2$)$_m$N(R)$_2$, or —(CH$_2$)$_m$OR.

In certain embodiments, the present invention provides a compound of formula I or III, wherein $R^3$ is —(CH$_2$)$_m$Cy, —(CH$_2$)$_n$OCy, or C$_{1-6}$ aliphatic substituted by —(CH$_2$)$_{0-4}$N(R°)$_2$, or —(CH$_2$)$_{0-4}$OR. In some such embodiments, R° is as defined above and described herein. In certain embodiments, the present invention provides a compound of formula I or III, wherein $R^3$ is —(CH$_2$)$_m$Cy, or —(CH$_2$)$_n$OCy. In some embodiments the present invention provides a compound of formula I or III, wherein $R^3$ is C$_{1-6}$ aliphatic substituted by —(CH$_2$)$_{0-4}$N(R°)$_2$, or —(CH$_2$)$_{0-4}$OR°. In some such embodiments, R° is as defined above and described herein. In certain embodiments, the present invention provides a compound of formula I or III, wherein $R^3$ is C$_{1-6}$ aliphatic substituted by —(CH$_2$)$_{0-4}$N(R°)$_2$, or —(CH$_2$)$_{0-4}$OR°, wherein R° is hydrogen, C$_{1-6}$ aliphatic, or a 5-6-membered saturated, partially unsaturated, or aryl ring having 0-4 heteroatoms independently selected from nitrogen, oxygen, or sulfur, wherein R° is optionally substituted by halogen, —CN or —(CH$_2$)$_{0-2}$OR$^●$, wherein R$^●$ is C$_{1-4}$ aliphatic. In certain embodiments, the present invention provides a compound of formula I or III, wherein $R^3$ is —(CH$_2$)$_m$Cy or C$_{1-6}$ aliphatic substituted by —(CH$_2$)$_{0-4}$OR°. In some such embodiments, R° is as defined above and described herein. In certain embodiments, the present invention provides a compound of formula I or III, wherein $R^3$ is —(CH$_2$)$_m$Cy or C$_{1-6}$ aliphatic substituted by —(CH$_2$)$_{0-4}$OR°, wherein R° is hydrogen, C$_{1-6}$ aliphatic, or a 5-6-membered saturated, partially unsaturated, or aryl ring having 0-4 heteroatoms independently selected from nitrogen, oxygen, or sulfur, wherein R° is optionally substituted by halogen, —CN or —(CH$_2$)$_{0-2}$OR$^●$, wherein R$^●$ is C$_{1-4}$ aliphatic. In certain embodiments, the present invention provides a compound of formula I or III, wherein $R^3$ is —(CH$_2$)$_m$Cy. In certain embodiments, the present invention provides a compound of formula I or III, wherein $R^3$ is —(CH$_2$)$_n$OCy. In some embodiments the present invention provides a compound of formula I or III, wherein $R^3$ is C$_{1-6}$ aliphatic substituted by —(CH$_2$)$_{0-4}$N(R°)$_2$. In some such embodiments, R° is as defined above and described herein. In some embodiments, the present invention provides a compound of formula I or III, wherein $R^3$ is C$_{1-6}$ aliphatic substituted by —(CH$_2$)$_{0-4}$N(R°)$_2$, wherein R° is hydrogen, C$_{1-6}$ aliphatic, or a 5-6-membered saturated, partially unsaturated, or aryl ring having 0-4 heteroatoms independently selected from nitrogen, oxygen, or sulfur, wherein R° is optionally substituted by —(CH$_2$)$_{0-2}$OR$^●$, wherein R$^●$ is C$_{1-4}$ aliphatic. In some embodiments the present invention provides a compound of formula I or III, wherein $R^3$ is C$_{1-6}$ aliphatic substituted by —(CH$_2$)$_{0-4}$OR°. In some such embodiments, R° is as defined above and described herein. In some embodiments the present invention provides a compound of formula I or III, wherein $R^3$ is C$_{1-6}$ aliphatic substituted by —(CH$_2$)$_{0-4}$OR°, wherein R° is hydrogen, C$_{1-6}$ aliphatic, or a 5-6-membered saturated, partially unsaturated, or aryl ring having 0-4 heteroatoms independently selected from nitrogen, oxygen, or sulfur, wherein R° is optionally substituted by halogen, —CN or —(CH$_2$)$_{0-2}$OR$^●$, wherein R$^●$ is C$_{1-4}$ aliphatic. In certain embodiments, the present invention provides a compound of formula I or III, wherein $R^3$ is —(CH$_2$)$_m$Cy, —(CH$_2$)$_n$OCy, or C$_{1-6}$ aliphatic substituted by —(CH$_2$)$_{0-4}$N(R°)$_2$, or —(CH$_2$)$_{0-4}$OR, wherein each R° is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur; and R° may be substituted by halogen, —(CH$_2$)$_{0-2}$R$^●$, -(haloR$^●$), —(CH$_2$)$_{0-2}$OH, —(CH$_2$)$_{0-2}$OR$^●$, —(CH$_2$)$_{0-2}$CH(OR$^●$)$_2$; —O(haloR$^●$), —CN, —N$_3$, —(CH$_2$)$_{0-2}$C(O)R$^●$, —(CH$_2$)$_{0-2}$C(O)OH, —(CH$_2$)$_{0-2}$C(O)OR$^●$, —(CH$_2$)$_{0-2}$SR$^●$, —(CH$_2$)$_{0-2}$SH, —(CH$_2$)$_{0-2}$NH$_2$, —(CH$_2$)$_{0-2}$NHR$^●$, —(CH$_2$)$_{0-2}$NR$^●$$_2$, —NO$_2$, —SiR$^●$$_3$, —OSiR$^●$$_3$, —C(O)SR$^●$, —(C$_{1-4}$ straight or branched alkylene)C(O)OR$^●$, or —SSR$^●$. In some such embodiments, R is C$_{1-4}$ aliphatic.

In certain embodiments, the present invention provides a compound of one of formula I, wherein $R^3$ is —(CH$_2$)$_m$Cy, —(CH$_2$)$_n$OCy, —(CH$_2$)$_m$N(R)$_2$, or —(CH$_2$)$_m$OR. In certain embodiments, the present invention provides a compound of formula I, wherein $R^3$ is —(CH$_2$)$_m$Cy, or —(CH$_2$)$_n$OCy. In some embodiments the present invention provides a compound of formula I, wherein $R^3$ is —(CH$_2$)$_m$N(R)$_2$, or —(CH$_2$)$_m$OR. In certain embodiments, the present invention provides a compound of one of formula I wherein $R^3$ is —(CH$_2$)$_m$Cy or —(CH$_2$)$_m$OR. In certain embodiments, the present invention provides a compound of formula I, wherein $R^3$ is —(CH$_2$)$_m$Cy. In certain embodiments, the present invention provides a compound of formula I, wherein $R^3$ is —(CH$_2$)$_n$OCy. In some embodiments the present invention provides a compound of formula I, wherein $R^3$ is —(CH$_2$)$_m$N(R)$_2$. In some embodiments the present invention provides a compound of formula I, wherein $R^3$ is —(CH$_2$)$_m$OR. In certain embodiments, the present invention provides a compound of one of formula I, wherein $R^3$ is —(CH$_2$)$_m$Cy, —(CH$_2$)$_n$OCy, —(CH$_2$)$_m$N(R)$_2$, or —(CH$_2$)$_m$OR, wherein each R is independently hydrogen or C$_{1-6}$ aliphatic, wherein said aliphatic or said Cy may be substituted with halogen; —(CH$_2$)$_{0-4}$R°; —(CH$_2$)$_{0-4}$OR;

—O(CH$_2$)$_{0-4}$R, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —(CH$_2$)$_{0-4}$SC(O)R°; —(CH$_2$)$_{0-4}$C(O)NR°$_2$; —C(S)NR°$_2$; —C(S)SR°; —SC(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R; —N(OR)R°; —C(NH)NR°$_2$; —P(O)$_2$R; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur; and R° may be substituted by halogen, —(CH$_2$)$_{0-2}$R$^●$, -(haloR$^●$), —(CH$_2$)$_{0-2}$OH, —(CH$_2$)$_{0-2}$OR$^●$—(CH$_2$)$_{0-2}$CH(OR$^●$)$_2$; —O(haloR$^●$), —CN, —N$_3$, —(CH$_2$)$_{0-2}$C(O)R$^●$, —(CH$_2$)$_{0-2}$C(O)OH, —(CH$_2$)$_{0-2}$C(O)OR$^●$, —(CH$_2$)$_{0-2}$SR$^●$, —(CH$_2$)$_{0-2}$SH, —(CH$_2$)$_{0-2}$NH$_2$, —(CH$_2$)$_{0-2}$NHR$^●$, —(CH$_2$)$_{0-2}$NR$^●_2$, —NO$_2$, —SiR$^●_3$, —OSiR$^●_3$, —C(O)SR$^●$, —(C$_{1-4}$ straight or branched alkylene)C(O)OR$^●$, or —SSR$^●$. In some such embodiments, R$^●$ is C$_{1-4}$ aliphatic.

In certain embodiments, the present invention provides a compound of formula I or III, wherein R$^3$ is —(CH$_2$)$_m$Cy where Cy is an optionally substituted 3-9 membered saturated or partially unsaturated monocyclic heterocyclic ring having 1-3 heteroatoms independently selected from nitrogen, oxygen, and sulfur; or a 7-12 membered saturated or partially unsaturated fused or bridged bicyclic heterocyclic ring having 1-3 heteroatoms independently selected from nitrogen, oxygen, and sulfur. In certain embodiments, the present invention provides a compound of formula I or III, wherein R$^3$ is —(CH$_2$)$_m$Cy where Cy is an optionally substituted 3-9 membered saturated or partially unsaturated monocyclic heterocyclic ring having 1-3 heteroatoms independently selected from nitrogen, oxygen, and sulfur. In certain embodiments, the present invention provides a compound of formula I or III, wherein R$^3$ is —(CH$_2$)$_m$Cy where Cy is an optionally substituted 7-12 membered saturated fused or bridged bicyclic heterocyclic ring having 1-3 heteroatoms independently selected from nitrogen, oxygen, and sulfur. In certain embodiments, the present invention provides a compound of formula I or III, wherein R$^3$ is —(CH$_2$)$_m$Cy where Cy is a 3-9 membered saturated or partially unsaturated monocyclic heterocyclic ring having 1-3 heteroatoms independently selected from nitrogen, oxygen, and sulfur, wherein said ring is optionally substituted with oxo, halogen; —(CH$_2$)$_{0-4}$R°; —(CH$_2$)$_{0-4}$OR°. In some such embodiments, R° is as defined above and described herein. In certain embodiments, the present invention provides a compound of formula I or III, wherein R$^3$ is —(CH$_2$)$_m$Cy where Cy is an optionally substituted 3-9 membered saturated or partially unsaturated monocyclic heterocyclic ring having 1-3 heteroatoms independently selected from nitrogen, oxygen, and sulfur, wherein: a substitutable carbon atom on Cy is optionally substituted with halogen, —(CH$_2$)$_{0-4}$R°, or —(CH$_2$)$_{0-4}$OR, and a substitutable nitrogen atom on Cy is optionally substituted with —R$^†$, wherein R° is hydrogen or C$_{1-6}$ aliphatic optionally substituted by halogen or —(CH$_2$)$_{0-2}$OR$^●$, wherein R$^●$ is C$_{1-4}$ aliphatic, and R$^†$ is C$_{1-6}$ aliphatic. In some such embodiments, two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of formula I or III, wherein R$^3$ is —CH$_2$Cy where Cy is an optionally substituted 3-9 membered saturated or partially unsaturated monocyclic heterocyclic ring having 1-3 heteroatoms independently selected from nitrogen, oxygen, and sulfur; or a 7-12 membered saturated or partially unsaturated fused or bridged bicyclic heterocyclic ring having 1-3 heteroatoms independently selected from nitrogen, oxygen, and sulfur. In certain embodiments, the present invention provides a compound of formula I or III, wherein R$^3$ is —CH$_2$Cy where Cy is an optionally substituted 3-9 membered saturated or partially unsaturated monocyclic heterocyclic ring having 1-3 heteroatoms independently selected from nitrogen, oxygen, and sulfur. In certain embodiments, the present invention provides a compound of formula I or III, wherein R$^3$ is —CH$_2$Cy where Cy is an optionally substituted 7-12 membered saturated or partially unsaturated fused or bridged bicyclic heterocyclic ring having 1-3 heteroatoms independently selected from nitrogen, oxygen, and sulfur. In certain embodiments, the present invention provides a compound of formula I or III, wherein R$^3$ is —CH$_2$Cy where Cy is a 3-9 membered saturated or partially unsaturated monocyclic heterocyclic ring having 1-3 heteroatoms independently selected from nitrogen, oxygen, and sulfur, wherein said ring is optionally substituted with oxo, halogen; —(CH$_2$)$_{0-4}$R°; —(CH$_2$)$_{0-4}$OR°. In some such embodiments, R° is as defined above and described herein. In certain embodiments, the present invention provides a compound of formula I or III, wherein R$^3$ is —CH$_2$Cy where Cy is an optionally substituted 3-9 membered saturated or partially unsaturated monocyclic heterocyclic ring having 1-3 heteroatoms independently selected from nitrogen, oxygen, and sulfur, wherein: a substitutable carbon atom on Cy is optionally substituted with halogen, —(CH$_2$)$_{0-4}$R°, or —(CH$_2$)$_{0-4}$OR, and a substitutable nitrogen atom on Cy is optionally substituted with —R$^†$, wherein R° is hydrogen or C$_{1-6}$ aliphatic optionally substituted by halogen or —(CH$_2$)$_{0-2}$OR$^●$, wherein R$^●$ is C$_{1-4}$ aliphatic, and R$^†$ is C$_{1-6}$ aliphatic. In some such embodiments, two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of formula I or III, wherein R$^3$ is —CH$_2$Cy where Cy is a 7-12 membered saturated or partially unsaturated fused or bridged bicyclic heterocyclic ring having 1-3 heteroatoms independently selected from nitrogen, oxygen, and sulfur, wherein said ring is optionally substituted with oxo, halogen, —(CH$_2$)$_{0-4}$R°, —(CH$_2$)$_{0-4}$OR°. In some such embodiments, R° is as defined above and described herein. In certain embodiments, the present invention provides a compound of formula I or III, wherein R$^3$ is —CH$_2$Cy where Cy is a 7-12 membered saturated or partially unsaturated fused or bridged bicyclic heterocyclic ring having 1-3 heteroatoms independently selected from nitrogen, oxygen, and sulfur, wherein: a substitutable carbon atom on Cy is optionally substituted with halogen, —$(CH_2)_{0-4}R°$, or —$(CH_2)_{0-4}OR^{\bullet}$, and a substitutable nitrogen atom on Cy is optionally substituted with —$R^{\dagger}$, wherein R° is hydrogen or $C_{1-6}$ aliphatic optionally substituted by halogen or —$(CH_2)_{0-2}OR^{\bullet}$, wherein $R^{\bullet}$ is $C_{1-4}$ aliphatic, and $R^{\dagger}$ is $C_{1-6}$ aliphatic. In some such embodiments, two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur.

In certain embodiments, the present invention provides a compound of formula I, wherein $R^3$ is —$(CH_2)_m$Cy where Cy is an optionally substituted 3-9 membered saturated or partially unsaturated monocyclic heterocyclic ring having 1-3 heteroatoms independently selected from nitrogen, oxygen, and sulfur; or a 6-12 membered saturated or partially unsaturated fused or bridged bicyclic heterocyclic ring having 1-3 heteroatoms independently selected from nitrogen, oxygen, and sulfur. In certain embodiments, the present invention provides a compound of formula I, wherein $R^3$ is —$(CH_2)_m$Cy where Cy is an optionally substituted 3-9 membered saturated or partially unsaturated monocyclic heterocyclic ring having 1-3 heteroatoms independently selected from nitrogen, oxygen, and sulfur. In certain embodiments, the present invention provides a compound of formula I, wherein $R^3$ is —$(CH_2)_m$Cy where Cy is an optionally substituted 6-12 membered saturated or partially unsaturated fused or bridged bicyclic heterocyclic ring having 1-3 heteroatoms independently selected from nitrogen, oxygen, and sulfur. In certain embodiments, the present invention provides a compound of formula I, wherein $R^3$ is —$(CH_2)_m$Cy where Cy is a 3-9 membered saturated or partially unsaturated monocyclic heterocyclic ring having 1-3 heteroatoms independently selected from nitrogen, oxygen, and sulfur, wherein said ring is optionally substituted with oxo, halogen; —$(CH_2)_{0-4}R°$; —$(CH_2)_{0-4}OR°$. In some such embodiments, R° is as defined above and described herein. In certain embodiments, the present invention provides a compound of formula I wherein $R^3$ is —$(CH_2)_m$Cy where Cy is a 3-9 membered saturated or partially unsaturated monocyclic heterocyclic ring having 1-3 heteroatoms independently selected from nitrogen, oxygen, and sulfur, wherein: a substitutable carbon atom on Cy is optionally substituted with halogen, —$(CH_2)_{0-4}R°$, or —$(CH_2)_{0-4}OR°$, and a substitutable nitrogen atom on Cy is optionally substituted with —$R^{\dagger}$, wherein R° is hydrogen or $C_{1-6}$ aliphatic optionally substituted by halogen or —$(CH_2)_{0-2}OR^{\bullet}$, wherein $R^{\bullet}$ is $C_{1-4}$ aliphatic, and $R^{\dagger}$ is $C_{1-6}$ aliphatic. In some such embodiments, two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of formula I, wherein $R^3$ is —$CH_2$Cy where Cy is an optionally substituted 3-9 membered saturated or partially unsaturated monocyclic heterocyclic ring having 1-3 heteroatoms independently selected from nitrogen, oxygen, and sulfur; or a 6-12 membered saturated or partially unsaturated fused or bridged bicyclic heterocyclic ring having 1-3 heteroatoms independently selected from nitrogen, oxygen, and sulfur. In certain embodiments, the present invention provides a compound of formula I, wherein $R^3$ is —$CH_2$Cy where Cy is an optionally substituted 3-9 membered saturated or partially unsaturated monocyclic heterocyclic ring having 1-3 heteroatoms independently selected from nitrogen, oxygen, and sulfur. In certain embodiments, the present invention provides a compound of formula I, wherein $R^3$ is —$CH_2$Cy where Cy is an optionally substituted 6-12 membered saturated fused or bridged bicyclic heterocyclic ring having 1-3 heteroatoms independently selected from nitrogen, oxygen, and sulfur. In certain embodiments, the present invention provides a compound of formula I, wherein $R^3$ is —$CH_2$Cy where Cy is a 3-9 membered saturated or partially unsaturated monocyclic heterocyclic ring having 1-3 heteroatoms independently selected from nitrogen, oxygen, and sulfur, wherein said ring is optionally substituted with oxo, halogen; —$(CH_2)_{0-4}R°$; —$(CH_2)_{0-4}OR°$. In some such embodiments, R° is as defined above and described herein. In certain embodiments, the present invention provides a compound of formula I, wherein $R^3$ is —$CH_2$Cy where Cy is a 3-9 membered saturated or partially unsaturated monocyclic heterocyclic ring having 1-3 heteroatoms independently selected from nitrogen, oxygen, and sulfur, wherein: a substitutable carbon atom on Cy is optionally substituted with halogen, —$(CH_2)_{0-4}R°$, or —$(CH_2)_{0-4}OR$, and a substitutable nitrogen atom on Cy is optionally substituted with —$R^{\dagger}$, wherein R° is hydrogen or $C_{1-6}$ aliphatic optionally substituted by halogen or —$(CH_2)_{0-2}OR^{\bullet}$, wherein $R^{\bullet}$ is $C_{1-4}$ aliphatic, and $R^{\dagger}$ is $C_{1-6}$ aliphatic. In some such embodiments, two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of formula I, wherein $R^3$ is —$CH_2$Cy where Cy is a 6-12 membered saturated fused or bridged bicyclic heterocyclic ring having 1-3 heteroatoms independently selected from nitrogen, oxygen, and sulfur, wherein said ring is optionally substituted with oxo, halogen; —$(CH_2)_{0-4}R°$; —$(CH_2)_{0-4}OR°$. In some such embodiments, R° is as defined above and described herein. In certain embodiments, the present invention provides a compound of formula I, wherein $R^3$ is —$CH_2$Cy where Cy is a 6-12 membered saturated fused or bridged bicyclic heterocyclic ring having 1-3 heteroatoms independently selected from nitrogen, oxygen, and sulfur, wherein: a substitutable carbon atom on Cy is optionally substituted with halogen, —$(CH_2)_{0-4}R°$, or —$(CH_2)_{0-4}OR°$, and a substitutable nitrogen atom on Cy is optionally substituted with —$R^{\dagger}$, wherein R° is hydrogen or $C_{1-6}$ aliphatic optionally substituted by halogen or —$(CH_2)_{0-2}OR^{\bullet}$, wherein $R^{\bullet}$ is $C_{1-4}$ aliphatic, and $R^{\dagger}$ is $C_{1-6}$ aliphatic. In some such embodiments, two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur.

In certain embodiments, the present invention provides a compound of formula I or III, wherein $R^3$ is —$(CH_2)_n$OCy where Cy is a 3-9 membered saturated or partially unsaturated monocyclic heterocyclic ring having 1-3 heteroatoms independently selected from nitrogen, oxygen, and sulfur; or a 7-12 membered saturated or partially unsaturated fused or bridged bicyclic heterocyclic ring having 1-3 heteroatoms independently selected from nitrogen, oxygen, and sulfur. In certain embodiments, the present invention provides a compound of formula I or III, wherein $R^3$ is —$(CH_2)_n$OCy where Cy is a 3-9 membered saturated or partially unsaturated monocyclic heterocyclic ring having 1-3 heteroatoms independently selected from nitrogen, oxygen, and sulfur. In certain embodiments, the present invention provides a compound of formula I or III, wherein $R^3$ is —$(CH_2)_n$OCy where Cy is a 7-12 membered saturated or partially unsaturated fused or bridged bicyclic heterocyclic ring having 1-3 heteroatoms independently selected from nitrogen, oxygen, and sulfur. In certain embodiments, the present invention provides a compound of formula I or III, wherein $R^3$ is —$(CH_2)_n$ OCy where Cy is a 3-9 membered saturated or partially unsaturated monocyclic heterocyclic ring having 1-3 heteroatoms independently selected from nitrogen, oxygen, and sulfur, wherein said ring is optionally substituted with oxo, halogen; —$(CH_2)_{0-4}R°$; —$(CH_2)_{0-4}OR°$. In some such embodiments, $R°$ is as defined above and described herein. In certain embodiments, the present invention provides a compound of formula I or III, wherein $R^3$ is —$(CH_2)_n$ OCy where Cy is a 3-9 membered saturated or partially unsaturated monocyclic heterocyclic ring having 1-3 heteroatoms independently selected from nitrogen, oxygen, and sulfur, wherein: a substitutable carbon atom on Cy is optionally substituted with halogen, —$(CH_2)_{0-4}R°$, or —$(CH_2)_{0-4}OR°$, and a substitutable nitrogen atom on Cy is optionally substituted with —$R^†$, wherein $R°$ is hydrogen or $C_{1-6}$ aliphatic optionally substituted by halogen or —$(CH_2)_{0-2}OR^●$, wherein $R^●$ is $C_{1-4}$ aliphatic, and $R^†$ is $C_{1-6}$ aliphatic. In some such embodiments, two independent occurrences of $R°$ may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of formula I or III, wherein $R^3$ is —$(CH_2)_n$OCy where Cy is a 7-12 membered saturated or partially unsaturated fused or bridged bicyclic heterocyclic ring having 1-3 heteroatoms independently selected from nitrogen, oxygen, and sulfur, wherein said ring is optionally substituted with oxo, halogen; —$(CH_2)_{0-4}R°$; —$(CH_2)_{0-4}OR°$. In some such embodiments, $R°$ is as defined above and described herein. In certain embodiments, the present invention provides a compound of formula I or III, wherein $R^3$ is —$(CH_2)_n$OCy where Cy is a 7-12 membered saturated or partially unsaturated fused or bridged bicyclic heterocyclic ring having 1-3 heteroatoms independently selected from nitrogen, oxygen, and sulfur, wherein: a substitutable carbon atom on Cy is optionally substituted with halogen, —$(CH_2)_{0-4}R°$, or —$(CH_2)_{0-4}OR°$, and a substitutable nitrogen atom on Cy is optionally substituted with —$R^†$, wherein $R°$ is hydrogen or $C_{1-6}$ aliphatic optionally substituted by halogen or —$(CH_2)_{0-2}OR^●$, wherein $R^●$ is $C_{1-4}$ aliphatic, and $R^†$ is $C_{1-6}$ aliphatic. In some such embodiments, two independent occurrences of $R°$ may be optionally taken together with their intervening atom(s), form a 3-12-membered saturated, partially unsaturated, or aryl mono- or bicyclic ring having 0-4 heteroatoms independently selected from nitrogen, oxygen, or sulfur.

In certain embodiments, the present invention provides a compound of formula I, wherein $R^3$ is —$(CH_2)_n$OCy where Cy is a 3-9 membered saturated or partially unsaturated monocyclic heterocyclic ring having 1-3 heteroatoms independently selected from nitrogen, oxygen, and sulfur; or a 6-12 membered saturated or partially unsaturated fused or bridged bicyclic heterocyclic ring having 1-3 heteroatoms independently selected from nitrogen, oxygen, and sulfur. In certain embodiments, the present invention provides a compound of formula I, wherein $R^3$ is —$(CH_2)_n$OCy where Cy is a 3-9 membered saturated or partially unsaturated monocyclic heterocyclic ring having 1-3 heteroatoms independently selected from nitrogen, oxygen, and sulfur. In certain embodiments, the present invention provides a compound of formula I, wherein $R^3$ is —$(CH_2)_n$OCy where Cy is a 6-12 membered saturated or partially unsaturated fused or bridged bicyclic heterocyclic ring having 1-3 heteroatoms independently selected from nitrogen, oxygen, and sulfur. In certain embodiments, the present invention provides a compound of formula I, wherein $R^3$ is —$(CH_2)_n$OCy where Cy is a 3-9 membered saturated or partially unsaturated monocyclic heterocyclic ring having 1-3 heteroatoms independently selected from nitrogen, oxygen, and sulfur; or a 6-12 membered saturated or partially unsaturated fused or bridged bicyclic heterocyclic ring having 1-3 heteroatoms independently selected from nitrogen, oxygen, and sulfur, wherein said ring is optionally substituted with oxo, halogen; —$(CH_2)_{0-4}R°$; —$(CH_2)_{0-4}OR°$. In some such embodiments, $R°$ is as defined above and described herein. In certain embodiments, the present invention provides a compound of formula I, wherein $R^3$ is —$(CH_2)_n$OCy where Cy is a 3-9 membered saturated or partially unsaturated monocyclic heterocyclic ring having 1-3 heteroatoms independently selected from nitrogen, oxygen, and sulfur; or a 6-12 membered saturated or partially unsaturated fused or bridged bicyclic heterocyclic ring having 1-3 heteroatoms independently selected from nitrogen, oxygen, and sulfur, wherein: a substitutable carbon atom of Cy is optionally substituted with halogen, —$(CH_2)_{0-4}R°$, or —$(CH_2)_{0-4}OR°$, and a substitutable nitrogen atom of Cy is optionally substituted with —$R^†$; wherein $R°$ is hydrogen or $C_{1-6}$ aliphatic optionally substituted by halogen or —$(CH_2)_{0-2}OR^●$, wherein $R^●$ is $C_{1-4}$ aliphatic, and $R^†$ is $C_{1-6}$ aliphatic. In some such embodiments, two independent occurrences of $R°$ may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of formula I, wherein $R^3$ is —$(CH_2)_n$OCy where Cy is a 3-9 membered saturated or partially unsaturated monocyclic heterocyclic ring having 1-3 heteroatoms independently selected from nitrogen, oxygen, and sulfur, wherein said ring is optionally substituted with oxo, halogen; —$(CH_2)_{0-4}R°$; —$(CH_2)_{0-4}OR°$. In some such embodiments, $R°$ is as defined above and described herein. In certain embodiments, the present invention provides a compound of formula I, wherein $R^3$ is —$(CH_2)_n$OCy where Cy is a 3-9 membered saturated or partially unsaturated monocyclic heterocyclic ring having 1-3 heteroatoms independently selected from nitrogen, oxygen, and sulfur, wherein: a substitutable carbon atom of Cy is optionally substituted with halogen, —$(CH_2)_{0-4}R°$, or —$(CH_2)_{0-4}OR°$, and a substitutable nitrogen atom of Cy is optionally substituted with —$R^†$, wherein $R°$ is hydrogen or $C_{1-6}$ aliphatic optionally substituted by halogen or —$(CH_2)_{0-2}OR^●$, wherein $R^●$ is $C_{1-4}$ aliphatic, and $R^†$ is $C_{1-6}$ aliphatic. In some such embodiments, two independent occurrences of $R°$ may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of formula I, wherein $R^3$ is —$(CH_2)_n$OCy where Cy is a 6-12 membered saturated or partially unsaturated fused or bridged bicyclic heterocyclic ring having 1-3 heteroatoms independently selected from nitrogen, oxygen, and sulfur, wherein said ring is optionally substituted with oxo, halogen; —$(CH_2)_{0-4}R°$; —$(CH_2)_{0-4}OR°$. In some such embodiments, $R°$ is as defined above and described herein. In certain embodiments, the present invention provides a compound of formula I wherein $R^3$ is —$(CH_2)_n$OCy where Cy is a 6-12 membered saturated or partially unsaturated fused or bridged bicyclic heterocyclic ring having 1-3 heteroatoms independently selected from nitrogen, oxygen, and sulfur, wherein: a substitutable carbon atom of Cy is optionally substituted with halogen, —$(CH_2)_{0-4}R°$, or —$(CH_2)_{0-4}OR°$, and a substitutable nitrogen atom of Cy is optionally substituted with —$R^†$, wherein R° is hydrogen or $C_{1-6}$ aliphatic optionally substituted by halogen or —$(CH_2)_{0-2}OR^●$, wherein $R^●$ is $C_{1-4}$ aliphatic, and $R^†$ is $C_{1-6}$ aliphatic. In some such embodiments, two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur.

In certain embodiments, the present invention provides a compound of formula I or III, wherein $R^3$ is $C_{1-6}$ aliphatic substituted by —$(CH_2)_{0-4}OR°$, wherein R° is hydrogen or $C_{1-6}$ aliphatic, wherein each R° may be substituted by halogen, —$(CH_2)_{0-2}R^●$, -(haloR$^●$), —$(CH_2)_{0-2}OH$, —$(CH_2)_{0-2}OR^●$, —$(CH_2)_{0-2}CH(OR^●)_2$; —$O(haloR^●)$, —CN, —$N_3$, —$(CH_2)_{0-2}C(O)R^●$, —$(CH_2)_{0-2}C(O)OH$, —$(CH_2)_{0-2}C(O)OR°$, —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —$SiR^●_3$, —$OSiR^●_3$, —$C(O)SR^●$, —$(C_{1-4}$ straight or branched alkylene$)C(O)OR^●$, or —$SSR^●$. In some such embodiments, $R^●$ is $C_{1-4}$ aliphatic. In certain embodiments, the present invention provides a compound of formula I or III, wherein $R^3$ is $C_{1-6}$ aliphatic substituted by —$(CH_2)_{0-4}OR°$, wherein R° is hydrogen. In certain embodiments, the present invention provides a compound of formula I or III, wherein $R^3$ is $C_{1-6}$ aliphatic substituted by —$(CH_2)_{0-4}OR°$, wherein R° is $C_{1-6}$ aliphatic, wherein each R° may be substituted by halogen, —$(CH_2)_{0-2}R^●$, -(haloR$^●$), —$(CH_2)_{0-2}OH$, —$(CH_2)_{0-2}OR^●$, —$(CH_2)_{0-2}CH(OR^●)_2$; —$O(haloR^●)$, —CN, —$N_3$, —$(CH_2)_{0-2}C(O)R^●$, —$(CH_2)_{0-2}C(O)OH$, —$(CH_2)_{0-2}C(O)OR^●$, —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —$SiR^●_3$, —$OSiR^●_3$, —$C(O)SR^●$, —$(C_{1-4}$ straight or branched alkylene$)C(O)OR^●$, or —$SSR^●$. In some such embodiments, $R^●$ is $C_{1-4}$ aliphatic.

In certain embodiments, the present invention provides a compound of formula I, wherein $R^3$ is —$(CH_2)_mOR$, wherein R is hydrogen or optionally substituted $C_{1-6}$ aliphatic. In certain embodiments, the present invention provides a compound of formula I, wherein $R^3$ is —$(CH_2)_mOR$, wherein R is hydrogen. In certain embodiments, the present invention provides a compound of formula I, wherein $R^3$ is —$(CH_2)_mOR$, wherein R is optionally substituted $C_{1-6}$ aliphatic. In certain embodiments, the present invention provides a compound of formula I, wherein $R^3$ is —$(CH_2)_mOR$, wherein R is $C_{1-6}$ aliphatic substituted with oxo, halogen, —CN, —$(CH_2)_{0-4}R°$, —$(CH_2)_{0-4}OR$, or —$(CH_2)_{0-4}S(O)_2R°$. In some such embodiments, R° is as defined above and described herein. In certain embodiments, the present invention provides a compound of formula I, wherein $R^3$ is —$(CH_2)_mOR$, wherein R is $C_{1-6}$ alkyl substituted with oxo, halogen, —CN, —$(CH_2)_{0-4}R°$, —$(CH_2)_{0-4}OR$, or —$(CH_2)_{0-4}S(O)_2R°$. In some such embodiments, R° is as defined above and described herein. In certain embodiments, the present invention provides a compound of formula I, wherein $R^3$ is —$(CH_2)_mOR$, wherein R is $C_{1-6}$ alkyl substituted with oxo, halogen, —CN, —$(CH_2)_{0-4}R°$, —$(CH_2)_{0-4}OR°$, —$(CH_2)_{0-4}N(R°)_2$, or —$(CH_2)_{0-4}S(O)_2R°$, wherein R° is $C_{1-6}$ aliphatic or a 5-6-membered saturated, partially unsaturated, or aryl ring having 0-4 heteroatoms independently selected from nitrogen, oxygen, or sulfur, wherein R° is optionally substituted with —$(CH_2)_{0-2}R^●$, wherein $R^●$ is $C_{1-4}$ aliphatic. In certain embodiments, the present invention provides a compound of formula I, wherein $R^3$ is —$(CH_2)_mOR$, wherein R is ethyl substituted with oxo, halogen, —CN, —$(CH_2)_{0-4}R°$, —$(CH_2)_{0-4}OR$, or —$(CH_2)_{0-4}S(O)_2R°$. In some such embodiments, R° is as defined above and described herein. In certain embodiments, the present invention provides a compound of formula I, wherein $R^3$ is —$(CH_2)_mOR$, wherein R is $C_{1-6}$ aliphatic substituted with oxo, halogen, —CN, —$(CH_2)_{0-4}R°$, —$(CH_2)_{0-4}OR°$, or —$(CH_2)_{0-4}S(O)_2R°$, wherein R° is independently hydrogen or $C_{1-6}$ aliphatic, wherein each R° may be substituted by halogen, —$(CH_2)_{0-2}R^●$, -(haloR$^●$), —$(CH_2)_{0-2}OH$, —$(CH_2)_{0-2}OR^●$, —$(CH_2)_{0-2}CH(OR^●)_2$; —$O(haloR^●)$, —CN, —$N_3$, —$(CH_2)_{0-2}C(O)R^●$, —$(CH_2)_{0-2}C(O)OH$, —$(CH_2)_{0-2}C(O)OR^●$, —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —$SiR^●_3$, —$OSiR^●_3$, —$C(O)SR^●$, —$(C_{1-4}$ straight or branched alkylene$)C(O)OR^●$, or —$SSR^●$. In some such embodiments, $R^●$ is $C_{1-4}$ aliphatic. In certain embodiments, the present invention provides a compound of formula I, wherein $R^3$ is —$(CH_2)_mOR$, wherein R is ethyl substituted with oxo, halogen, —CN, —$(CH_2)_{0-4}R°$, —$(CH_2)_{0-4}OR°$, or —$(CH_2)_{0-4}N(R°)_2$, or —$(CH_2)_{0-4}S(O)_2R°$, wherein R° is $C_{1-6}$ aliphatic or a 5-6-membered saturated, partially unsaturated, or aryl ring having 0-4 heteroatoms independently selected from nitrogen, oxygen, or sulfur, wherein R° is optionally substituted with —$(CH_2)_{0-2}R^●$, wherein $R^●$ is $C_{1-4}$ aliphatic.

In certain embodiments, the present invention provides a compound of formula I or III, wherein $R^3$ is $C_{1-6}$ aliphatic substituted by —$(CH_2)_{0-4}N(R°)_2$, wherein each R° is independently hydrogen or $C_{1-6}$ aliphatic, wherein each R° may be substituted by halogen, —$(CH_2)_{0-2}R^●$, -(haloR$^●$), —$(CH_2)_{0-2}OH$, —$(CH_2)_{0-2}OR^●$, —$(CH_2)_{0-2}CH(OR^●)_2$; —$O(haloR^●)$, —CN, —$N_3$, —$(CH_2)_{0-2}C(O)R^●$, —$(CH_2)_{0-2}C(O)OH$, —$(CH_2)_{0-2}C(O)OR^●$, —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —$SiR^●_3$, —$OSiR^●_3$, —$C(O)SR^●$, —$(C_{1-4}$ straight or branched alkylene$)C(O)OR^●$, or —$SSR^●$. In some such embodiments, $R^●$ is $C_{1-4}$ aliphatic. In certain embodiments, the present invention provides a compound of formula I or III, wherein $R^3$ is $C_{1-6}$ aliphatic substituted by —$(CH_2)_{0-4}N(R°)_2$, wherein each R° is hydrogen. In certain embodiments, the present invention provides a compound of formula I or III, wherein $R^3$ is $C_{1-6}$ aliphatic substituted by —$(CH_2)_{0-4}N(R°)_2$, wherein each R° is $C_{1-6}$ aliphatic, wherein each R° may be substituted by halogen, —$(CH_2)_{0-2}R^●$, -(haloR$^●$), —$(CH_2)_{0-2}OH$, —$(CH_2)_{0-2}OR^●$, —$(CH_2)_{0-2}CH(OR^●)_2$; —$O(haloR^●)$, —CN, —$N_3$, —$(CH_2)_{0-2}C(O)R^●$, —$(CH_2)_{0-2}C(O)OH$, —$(CH_2)_{0-2}C(O)OR^●$, —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —$SiR^●_3$, —$OSiR^●_3$, —$C(O)SR^●$, —$(C_{1-4}$ straight or branched alkylene$)C(O)OR^●$, or —$SSR^●$. In some such embodiments, $R^●$ is $C_{1-4}$ aliphatic.

In certain embodiments, the present invention provides a compound of formula I, wherein $R^3$ is —$(CH_2)_mN(R)_2$, wherein each R is independently hydrogen or optionally substituted $C_{1-6}$ aliphatic. In certain embodiments, the present invention provides a compound of formula I, wherein $R^3$ is —$(CH_2)_mN(R)_2$, wherein each R is hydrogen. In certain embodiments, the present invention provides a compound of formula I, wherein $R^3$ is —$(CH_2)_mN(R)_2$, wherein each R is optionally substituted $C_{1-6}$ aliphatic. In certain embodiments, the present invention provides a compound of formula I, wherein $R^3$ is —$(CH_2)_mN(R)_2$, wherein R is $C_{1-6}$ aliphatic substituted with oxo, halogen, —CN, —(CH$_2$)$_{0-4}$ R°, —(CH$_2$)$_{0-4}$OR°, or —(CH$_2$)$_{0-4}$S(O)$_2$R°. In some such embodiments, R° is as defined above and described herein. In certain embodiments, the present invention provides a compound of formula I, wherein R$^3$ is —(CH$_2$)$_m$N(R)$_2$, wherein each R is C$_{1-6}$ alkyl substituted with oxo, halogen, —CN, —(CH$_2$)$_{0-4}$R°, —(CH$_2$)$_{0-4}$OR°, or —(CH$_2$)$_{0-4}$S(O)$_2$R°. In some such embodiments, R° is as defined above and described herein. In certain embodiments, the present invention provides a compound of formula I, wherein R$^3$ is —(CH$_2$)$_m$N(R)$_2$, wherein each R is C$_{1-6}$ alkyl optionally substituted with oxo, halogen, —CN, —(CH$_2$)$_{o04}$R°, —(CH$_2$)$_{0-4}$OR°, or —(CH$_2$)$_{0-4}$S(O)$_2$R°, wherein R° is C$_{1-6}$ aliphatic. In certain embodiments, the present invention provides a compound of formula I, wherein R$^3$ is —(CH$_2$)$_m$N(R)$_2$, wherein each R is ethyl substituted with oxo, halogen, —CN, —(CH$_2$)$_{0-4}$R°, —(CH$_2$)$_{0-4}$OR, or —(CH$_2$)$_{0-4}$S(O)$_2$R°. In some such embodiments, R° is as defined above and described herein. In certain embodiments, the present invention provides a compound of formula I, wherein R$^3$ is —(CH$_2$)$_m$N(R)$_2$, wherein each R is ethyl substituted with oxo, halogen, —CN, —(CH$_2$)$_{0-4}$R°, —(CH$_2$)$_{0-4}$OR°, or —(CH$_2$)$_{0-4}$S(O)$_2$R°, wherein R° is C$_{1-6}$ aliphatic. In certain embodiments, the present invention provides a compound of formula I, wherein R$^3$ is —(CH$_2$)$_m$N(R)$_2$, wherein R is C$_{1-6}$ aliphatic substituted with oxo, halogen, —CN, —(CH$_2$)$_{0-4}$R°, —(CH$_2$)$_{0-4}$OR°, or —(CH$_2$)$_{0-4}$S(O)$_2$R°, wherein R° is C$_{1-6}$ aliphatic, wherein each R° may be substituted by halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet{}_3$, —OSiR$^\bullet{}_3$, —C(O)SR$^\bullet$, —(C$_{1-4}$ straight or branched alkylene)C(O)OR$^\bullet$, or —SSR$^\bullet$. In some such embodiments, R$^\bullet$ is C$_{1-4}$ aliphatic.

In certain embodiments, the present invention provides a compound of formula I or III, wherein R$^3$ is —CH$_2$N(R°)$_2$, wherein each R° is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur; wherein R° may be substituted by halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet{}_3$, —OSiR$^\bullet{}_3$, —C(O)SR$^\bullet$, —(C$_{1-4}$ straight or branched alkylene)C(O)OR$^\bullet$, or —SSR$^\bullet$. In some such embodiments, R$^\bullet$ is C$_{1-4}$ aliphatic.

In certain embodiments, the present invention provides a compound of formula I, wherein R$^3$ is —CH$_2$N(R)$_2$. In certain embodiments, the present invention provides a compound of formula I, wherein R$^3$ is —CH$_2$N(R)$_2$, wherein each R is independently hydrogen or optionally substituted C$_{1-6}$ aliphatic. In certain embodiments, the present invention provides a compound of formula I, wherein R$^3$ is —CH$_2$N(R)$_2$, wherein each R is independently hydrogen or C$_{1-6}$ aliphatic substituted with oxo, halogen, —CN, —(CH$_2$)$_{0-4}$R°, —(CH$_2$)$_{0-4}$OR, or —(CH$_2$)$_{0-4}$S(O)$_2$R°. In some such embodiments, R° is as defined above and described herein. In certain embodiments, the present invention provides a compound of formula I, wherein R$^3$ is —CH$_2$N(R)$_2$, wherein each R is independently hydrogen or C$_{1-6}$ aliphatic optionally substituted with oxo, halogen, —CN, —(CH$_2$)$_{0-4}$R°, —(CH$_2$)$_{0-4}$OR°, or —(CH$_2$)$_{0-4}$S(O)$_2$R$_o$, wherein R° is C$_{1-6}$ aliphatic. In certain embodiments, the present invention provides a compound of formula I, wherein R$^3$ is —CH$_2$N (R)$_2$, wherein each R is independently hydrogen or C$_{1-6}$ aliphatic substituted with oxo, halogen, —CN, —(CH$_2$)$_{0-4}$R°, —(CH$_2$)$_{0-4}$OR°, or —(CH$_2$)$_{0-4}$S(O)$_2$R°. In some such embodiments, R° is as defined above and described herein. In certain embodiments, the present invention provides a compound of formula I, wherein R$^3$ is —CH$_2$N(R)$_2$, wherein each R is independently hydrogen or C$_{1-6}$ aliphatic optionally substituted with oxo, halogen, —CN, —(CH$_2$)$_{0-4}$R°, —(CH$_2$)$_{0-4}$OR°, or —(CH$_2$)$_{0-4}$S(O)$_2$R°, wherein R° is C$_{1-6}$ aliphatic, or two R groups on the same nitrogen are taken together with the nitrogen to form a 3-7 membered saturated or partially unsaturated heterocyclic ring having 1-3 heteroatoms selected from nitrogen, oxygen, or sulfur.

In certain embodiments, the present invention provides a compound of formula I or III, wherein R$^3$ is C$_{1-6}$ aliphatic substituted by —CH$_2$OR°, wherein R° is hydrogen or C$_{1-6}$ aliphatic, wherein each R° may be substituted by halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet{}_3$, —OSiR$^\bullet{}_3$, —C(O)SR$^\bullet$, —(C$_{1-4}$ straight or branched alkylene)C(O)OR$^\bullet$, or —SSR$^\bullet$. In some such embodiments, R$^\bullet$ is C$_{1-4}$ aliphatic. In certain embodiments, the present invention provides a compound of formula I or III, wherein R$^3$ is C$_{1-6}$ aliphatic substituted by —CH$_2$OR$^\bullet$, wherein R° is hydrogen. In certain embodiments, the present invention provides a compound of formula I or III, wherein R$^3$ is C$_{1-6}$ aliphatic substituted by —CH$_2$OR°, wherein R° is C$_{1-6}$ aliphatic, wherein each R° may be substituted by halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet{}_3$, —OSiR$^\bullet{}_3$, —C(O)SR$^\bullet$, —(C$_{1-4}$ straight or branched alkylene)C(O)OR$^\bullet$, or —SSR$^\bullet$. In some such embodiments, R$^\bullet$ is C$_{1-4}$ aliphatic.

In certain embodiments, the present invention provides a compound of formula I, wherein R$^3$ is —CH$_2$OR, wherein R is hydrogen or optionally substituted C$_{1-6}$ aliphatic. In certain embodiments, the present invention provides a compound of formula I, wherein R$^3$ is —CH$_2$OR, wherein R is hydrogen. In certain embodiments, the present invention provides a compound of formula I, wherein R$^3$ is —CH$_2$OR, wherein R is optionally substituted C$_{1-6}$ aliphatic. In certain embodiments, the present invention provides a compound of formula I, wherein R$^3$ is —CH$_2$OR, wherein R is C$_{1-6}$ aliphatic substituted with oxo, halogen, —CN, —(CH$_2$)$_{0-4}$R, —(CH$_2$)$_{0-4}$OR°, or —(CH$_2$)$_{0-4}$S(O)$_2$R°. In some such embodiments, R° is as defined above and described herein. In certain embodiments, the present invention provides a compound of formula I, wherein R$^3$ is —CH$_2$OR, wherein R is C$_{1-6}$ aliphatic substituted with oxo, halogen, —CN, —(CH$_2$)$_{0-4}$R°, —(CH$_2$)$_{0-4}$OR°, or —(CH$_2$)$_{0-4}$S(O)$_2$R°, wherein R° is C$_{1-6}$ aliphatic. In certain embodiments, the present invention provides a compound of formula I, wherein R$^3$ is —CH$_2$OR, wherein R is C$_{1-6}$ alkyl substituted with oxo, halogen, —CN, —(CH$_2$)$_{0-4}$R°, —(CH$_2$)$_{0-4}$OR, or —(CH$_2$)$_{0-4}$S(O)$_2$R°. In some embodiments, R° is as defined above and described herein. In certain embodiments, the present invention provides a compound of formula I, wherein R$^3$ is —CH$_2$OR, wherein R is C$_{1-6}$ alkyl substituted with oxo, halogen, —CN, —(CH$_2$)$_{0-4}$R°, —(CH$_2$)$_{0-4}$OR°, or —(CH$_2$)$_{0-4}$S(O)$_2$R°, wherein R° is C$_{1-6}$ aliphatic. In certain embodiments, the present invention provides a compound of formula I, wherein R$^3$ is —CH$_2$OR, wherein R is ethyl substituted with oxo, halogen, —CN, —(CH$_2$)$_{0-4}$R°, —(CH$_2$)$_{0-4}$OR, or —(CH$_2$)$_{0-4}$S(O)$_2$R°. In some such embodiments, R° is as defined above and described herein. In some embodiments of formula I, R$^3$ is —CH$_2$OR, wherein R is ethyl substituted with oxo, halogen, —CN, —(CH$_2$)$_{0-4}$R°, —(CH$_2$)$_{0-4}$OR°, or —(CH$_2$)$_{0-4}$S(O)$_2$R°, R° is C$_{1-6}$ aliphatic. In certain embodiments, the present invention provides a compound of formula I, wherein R$^3$ is —CH$_2$OR, wherein R is C$_{1-6}$ aliphatic substituted with oxo, halogen, —CN, —(CH$_2$)$_{0-4}$R°, —(CH$_2$)$_{0-4}$OR°, or —(CH$_2$)$_{0-4}$S(O)$_2$R°, wherein each R° is independently hydrogen or C$_{1-6}$ aliphatic, wherein R° may be substituted by halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$. In some such embodiments, R$^\bullet$ is C$_{1-4}$ aliphatic.

In certain embodiments, the present invention provides a compound of formula I or III, wherein R$^3$ is —(CH$_2$)$_m$Cy where Cy is optionally substituted piperidinyl. In certain embodiments, the present invention provides a compound of formula I or III, wherein R$^3$ is —(CH$_2$)$_m$Cy where Cy is piperidinyl optionally substituted with oxo, halogen, —(CH$_2$)$_{0-4}$R, or —(CH$_2$)$_{0-4}$OR, wherein R° is as defined above and described herein. In certain embodiments, the present invention provides a compound of formula I or III, wherein R$^3$ is —(CH$_2$)$_m$Cy where Cy is piperidinyl optionally substituted with oxo, halogen, —(CH$_2$)$_{0-4}$R°, or —(CH$_2$)$_{0-4}$OR, wherein each R° is independently C$_{1-6}$ aliphatic, wherein two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of formula I or III, wherein R$^3$ is —(CH$_2$)$_n$OCy where Cy is optionally substituted oxetanyl. In certain embodiments, the present invention provides a compound of formula I or III, wherein R$^3$ is —(CH$_2$)$_n$OCy where Cy is oxetanyl optionally substituted with oxo, halogen, —(CH$_2$)$_{0-4}$R°, or —(CH$_2$)$_{0-4}$OR°, wherein R° is C$_{1-6}$ aliphatic. In certain embodiments, the present invention provides a compound of formula I or III, wherein R$^3$ is —(CH$_2$)$_n$OCy where Cy is oxetanyl optionally substituted with oxo, halogen, —(CH$_2$)$_{0-4}$R°, or —(CH$_2$)$_{0-4}$OR°, wherein R° is C$_{1-6}$ aliphatic, wherein two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of formula I or III, wherein R$^3$ is —(CH$_2$)$_n$OCy where Cy is oxetanyl optionally substituted with oxo, halogen, —(CH$_2$)$_{0-4}$R°, or —(CH$_2$)$_{0-4}$OR°, wherein each R° is C$_{1-6}$ aliphatic, wherein two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur.

In certain embodiments, the present invention provides a compound of formula I, wherein R$^3$ is —(CH$_2$)$_m$Cy where Cy is optionally substituted piperidinyl. In certain embodiments, the present invention provides a compound of formula I, wherein R$^3$ is —(CH$_2$)$_m$Cy where Cy is piperidinyl optionally substituted with oxo, halogen, —(CH$_2$)$_{0-4}$R°, or —(CH$_2$)$_{0-4}$OR°, wherein each R° is C$_{1-6}$ aliphatic, wherein two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of formula I, wherein R$^3$ is —(CH$_2$)$_n$OCy where Cy is optionally substituted oxetanyl. In certain embodiments, the present invention provides a compound of formula I, wherein R$^3$ is —(CH$_2$)$_n$OCy where Cy is oxetanyl optionally substituted with oxo, halogen, —(CH$_2$)$_{0-4}$R, or —(CH$_2$)$_{0-4}$OR°, wherein each R° is C$_{1-6}$ aliphatic, wherein two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of formula I, wherein R$^3$ is —(CH$_2$)$_n$OCy where Cy is oxetanyl optionally substituted with oxo, halogen, —(CH$_2$)$_{0-4}$R°, or —(CH$_2$)$_{0-4}$OR°, wherein each R° is C$_{1-6}$ aliphatic, wherein two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur.

In certain embodiments, the present invention provides a compound of formula I selected from those depicted in Table 1, below.

TABLE 1

| Compound # | Structure |
|---|---|
| I-1 | 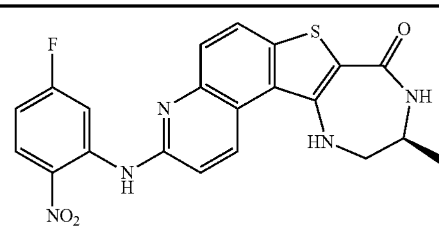 |

TABLE 1-continued

| Compound # | Structure |
|---|---|
| I-2 | 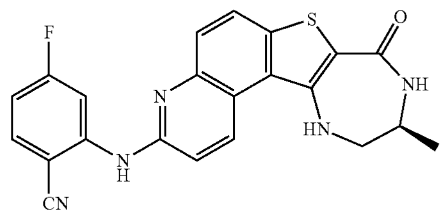 [SMILES: C[C@H]1CNc2c(sc3ccc4nc(Nc5cc(F)ccc5C#N)ccc4c23)C(=O)N1] |
| I-3 | 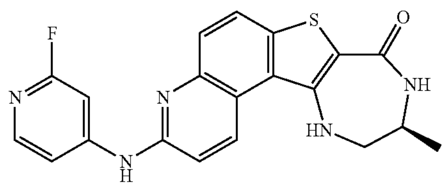 [SMILES: C[C@H]1CNc2c(sc3ccc4nc(Nc5ccnc(F)c5)ccc4c23)C(=O)N1] |
| I-4 | 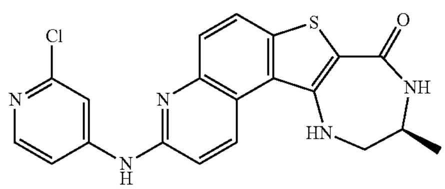 [SMILES: C[C@H]1CNc2c(sc3ccc4nc(Nc5ccnc(Cl)c5)ccc4c23)C(=O)N1] |
| I-5 | 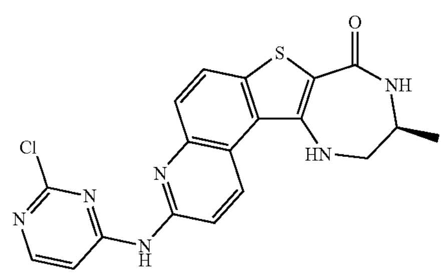 [SMILES: C[C@H]1CNc2c(sc3ccc4nc(Nc5ccnc(Cl)n5)ccc4c23)C(=O)N1] |
| I-6 | 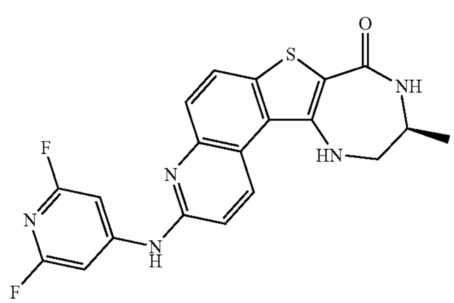 [SMILES: C[C@H]1CNc2c(sc3ccc4nc(Nc5cc(F)nc(F)c5)ccc4c23)C(=O)N1] |
| I-7 | 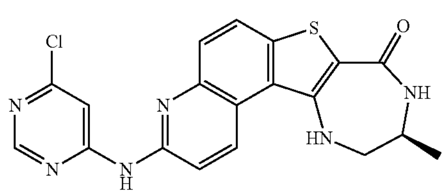 [SMILES: C[C@H]1CNc2c(sc3ccc4nc(Nc5cc(Cl)ncn5)ccc4c23)C(=O)N1] |

TABLE 1-continued

| Compound # | Structure |
|---|---|
| I-8 | 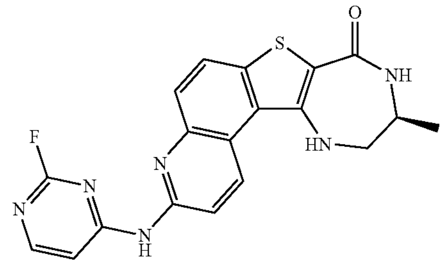 [SMILES: C[C@H]1CNc2c(sc3ccc4nc(Nc5ccnc(F)n5)ccc4c23)C(=O)N1] |
| I-9 | 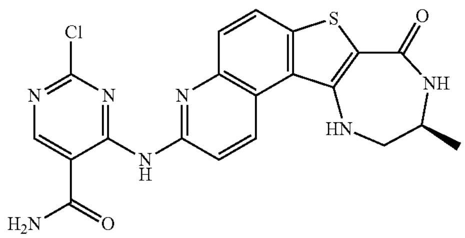 [SMILES: C[C@H]1CNc2c(sc3ccc4nc(Nc5nc(Cl)ncc5C(N)=O)ccc4c23)C(=O)N1] |
| I-10 | 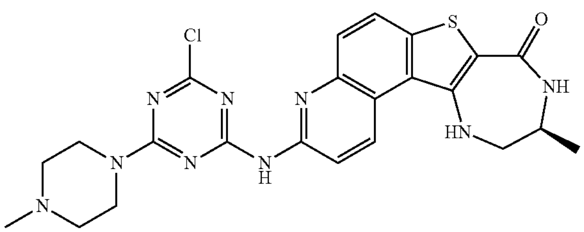 |
| I-11 | 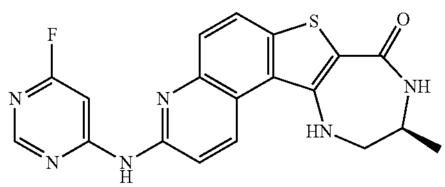 [SMILES: C[C@H]1CNc2c(sc3ccc4nc(Nc5cc(F)ncn5)ccc4c23)C(=O)N1] |
| I-12 | 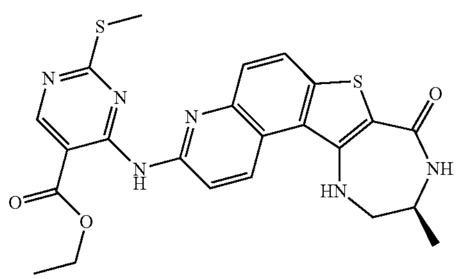 [SMILES: CCOC(=O)c1cnc(SC)nc1Nc1ccc2c(ccc3sc4c(c32)NC[C@H](C)NC4=O)n1] |
| I-13 | 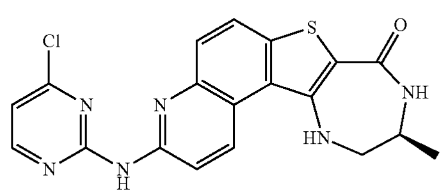 [SMILES: C[C@H]1CNc2c(sc3ccc4nc(Nc5nccc(Cl)n5)ccc4c23)C(=O)N1] |

TABLE 1-continued

| Compound # | Structure |
|---|---|
| I-14 | 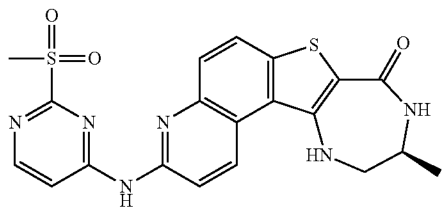 |
| I-15 | 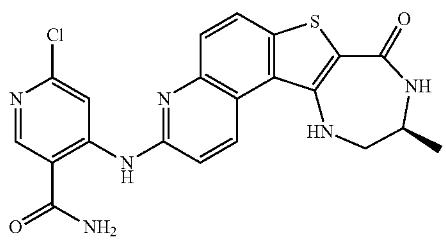 [SMILES: C[C@H]1CNc2c(sc3ccc4nc(Nc5cc(Cl)ncc5C(N)=O)ccc4c23)C(=O)N1] |
| I-16 | 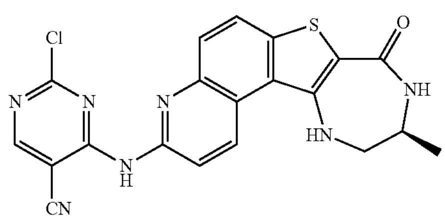 [SMILES: C[C@H]1CNc2c(sc3ccc4nc(Nc5nc(Cl)ncc5C#N)ccc4c23)C(=O)N1] |
| I-17 | 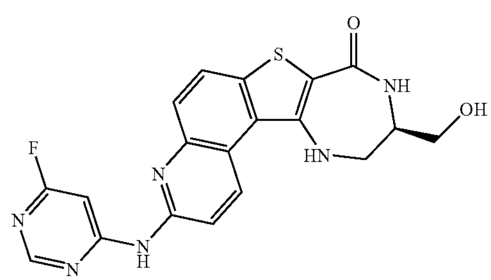 [SMILES: O=C1N[C@@H](CO)CNc2c1sc1ccc3nc(Nc4cc(F)ncn4)ccc3c21] |
| I-18 | 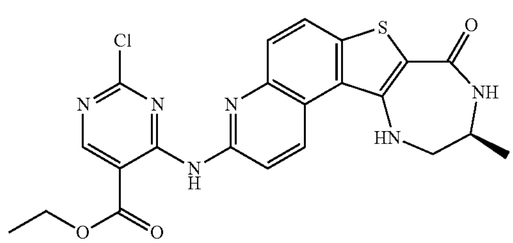 [SMILES: CCOC(=O)c1cnc(Cl)nc1Nc1ccc2c(ccc3sc4c(c32)NC[C@H](C)NC4=O)n1] |
| I-19 | 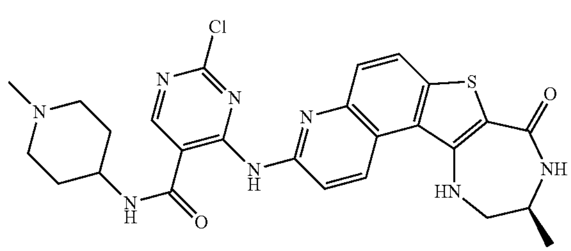 [SMILES: C[C@H]1CNc2c(sc3ccc4nc(Nc5nc(Cl)ncc5C(=O)NC5CCN(C)CC5)ccc4c23)C(=O)N1] |

TABLE 1-continued
| Compound # | Structure |
|---|---|
| I-20 | 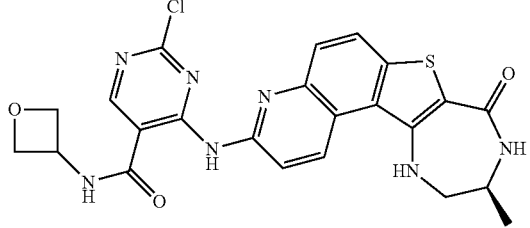 [SMILES: C[C@H]1CNc2c(sc3ccc4nc(Nc5nc(Cl)ncc5C(=O)NC5COC5)ccc4c23)C(=O)N1] |
| I-21 | 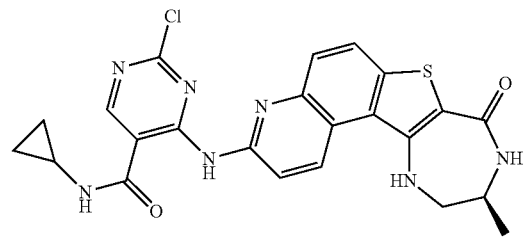 [SMILES: C[C@H]1CNc2c(sc3ccc4nc(Nc5nc(Cl)ncc5C(=O)NC5CC5)ccc4c23)C(=O)N1] |
| I-22 | 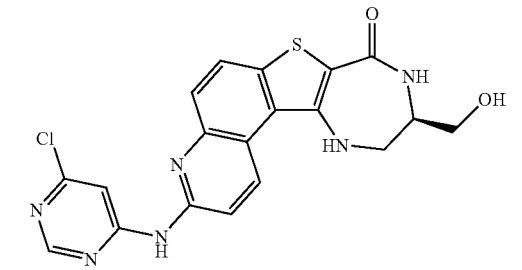 [SMILES: O=C1N[C@@H](CO)CNc2c1sc1ccc3nc(Nc4cc(Cl)ncn4)ccc3c21] |
| I-23 | 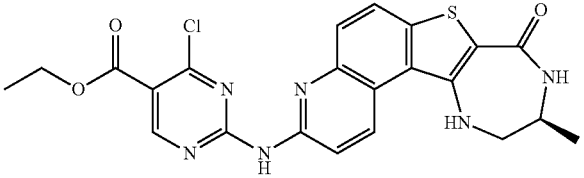 [SMILES: CCOC(=O)c1cnc(Nc2ccc3c(ccc4sc5c(c43)NC[C@H](C)NC5=O)n2)nc1Cl] |
| I-24 | 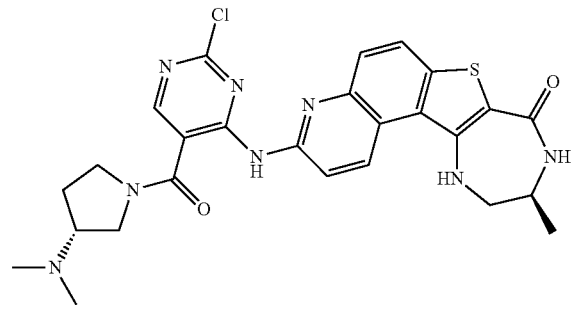 [SMILES: C[C@H]1CNc2c(sc3ccc4nc(Nc5nc(Cl)ncc5C(=O)N5CC[C@@H](N(C)C)C5)ccc4c23)C(=O)N1] |
| I-25 | 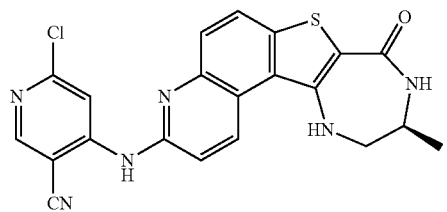 [SMILES: C[C@H]1CNc2c(sc3ccc4nc(Nc5cc(Cl)ncc5C#N)ccc4c23)C(=O)N1] |

TABLE 1-continued
| Compound # | Structure |
|---|---|
| I-26 | 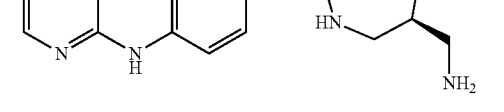 |
| I-27 | 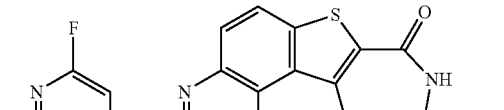 |
| I-28 | 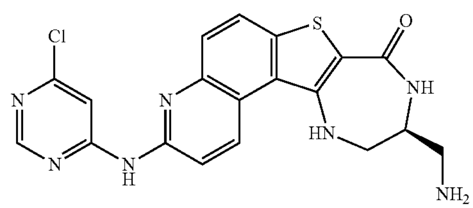 [SMILES: NC[C@H]1CNc2c(sc3ccc4nc(Nc5cc(Cl)ncn5)ccc4c23)C(=O)N1] |
| I-29 | 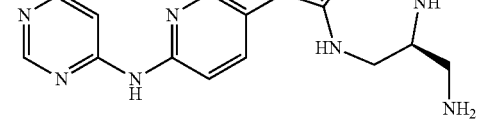 |
| I-30 | 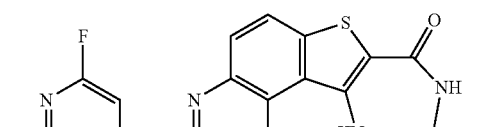 |
| I-31 | 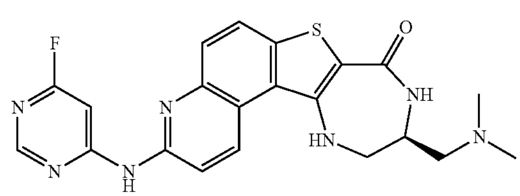 [SMILES: CN(C)C[C@H]1CNc2c(sc3ccc4nc(Nc5cc(F)ncn5)ccc4c23)C(=O)N1] |

TABLE 1-continued

| Compound # | Structure |
|---|---|
| I-32 | 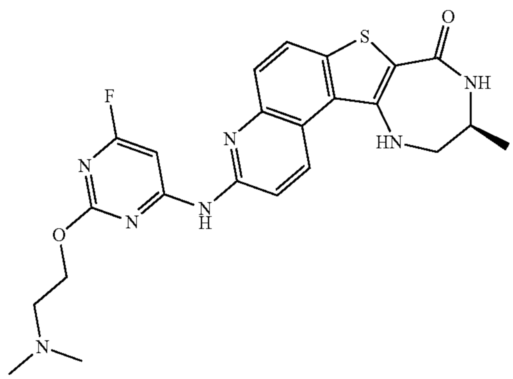 |
| I-33 | 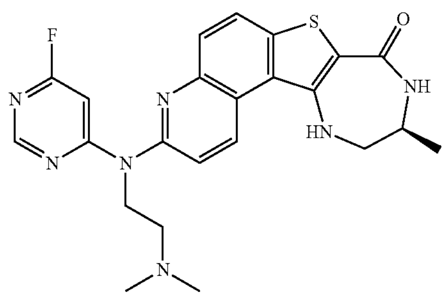 [SMILES: C[C@H]1CNc2c(sc3ccc4nc(N(CCN(C)C)c5cc(F)ncn5)ccc4c23)C(=O)N1] |
| I-34 | 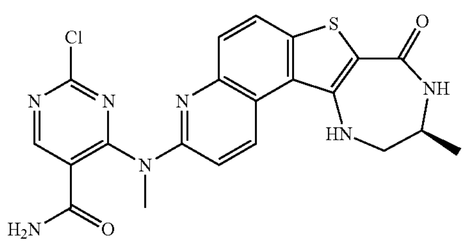 [SMILES: C[C@H]1CNc2c(sc3ccc4nc(N(C)c5nc(Cl)ncc5C(N)=O)ccc4c23)C(=O)N1] |
| I-35 | 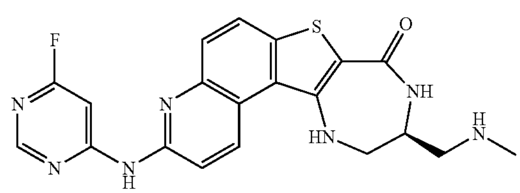 [SMILES: CNC[C@H]1CNc2c(sc3ccc4nc(Nc5cc(F)ncn5)ccc4c23)C(=O)N1] |
| I-36 | 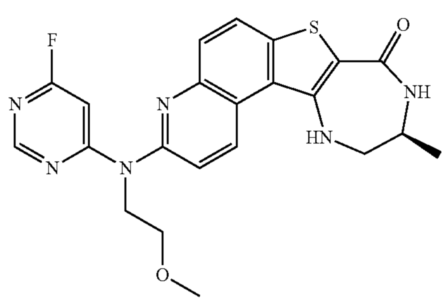 [SMILES: COCCN(c1cc(F)ncn1)c1ccc2c(ccc3sc4c(c32)NC[C@H](C)NC4=O)n1] |

TABLE 1-continued

| Compound # | Structure |
|---|---|
| I-37 | 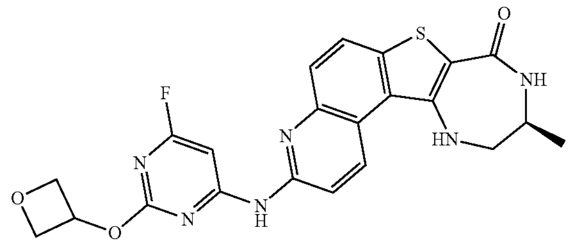 [SMILES: C[C@H]1CNc2c(sc3ccc4nc(Nc5cc(F)nc(OC6COC6)n5)ccc4c23)C(=O)N1] |
| I-38 | 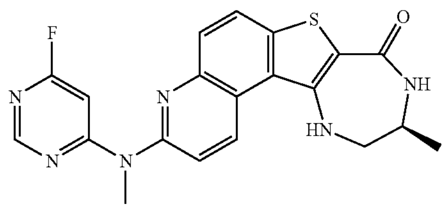 [SMILES: C[C@H]1CNc2c(sc3ccc4nc(N(C)c5cc(F)ncn5)ccc4c23)C(=O)N1] |
| I-39 | 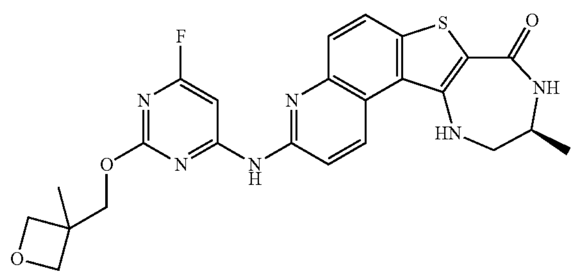 [SMILES: C[C@H]1CNc2c(sc3ccc4nc(Nc5cc(F)nc(OCC6(C)COC6)n5)ccc4c23)C(=O)N1] |
| I-40 | 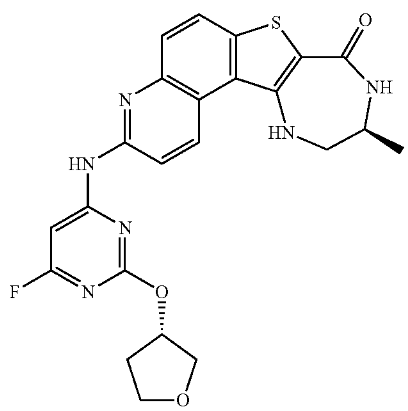 [SMILES: C[C@H]1CNc2c(sc3ccc4nc(Nc5cc(F)nc(O[C@H]6CCOC6)n5)ccc4c23)C(=O)N1] |
| I-41 | 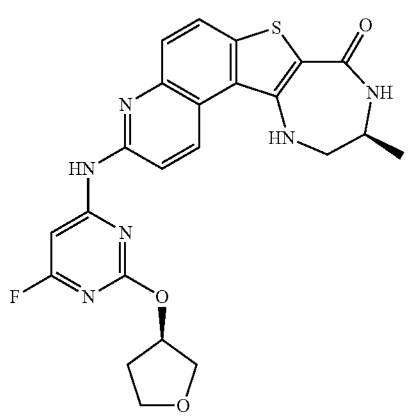 [SMILES: C[C@H]1CNc2c(sc3ccc4nc(Nc5cc(F)nc(O[C@@H]6CCOC6)n5)ccc4c23)C(=O)N1] |

TABLE 1-continued

| Compound # | Structure |
|---|---|
| I-42 | 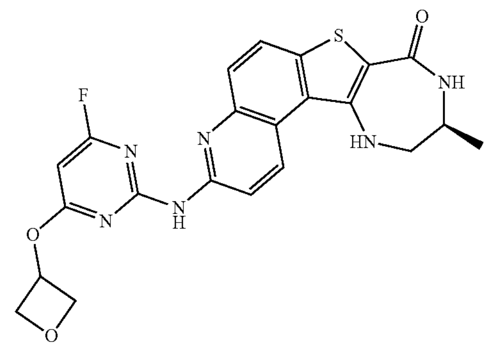 [SMILES: C[C@H]1CNc2c(sc3ccc4nc(Nc5nc(F)cc(OC6COC6)n5)ccc4c23)C(=O)N1] |
| I-43 | 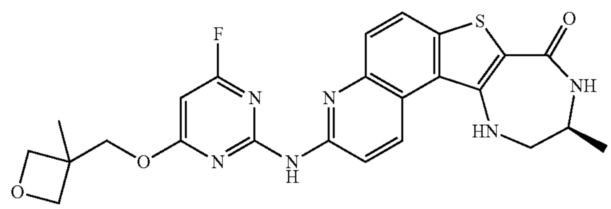 [SMILES: C[C@H]1CNc2c(sc3ccc4nc(Nc5nc(F)cc(OCC6(C)COC6)n5)ccc4c23)C(=O)N1] |
| I-44 | 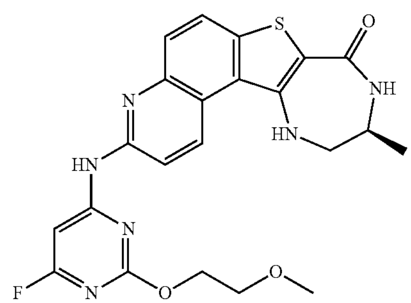 [SMILES: COCCOc1nc(F)cc(Nc2ccc3c(ccc4sc5c(c43)NC[C@H](C)NC5=O)n2)n1] |
| I-45 | 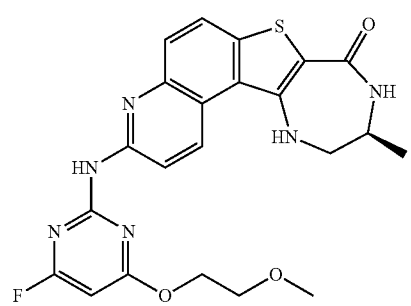 [SMILES: COCCOc1cc(F)nc(Nc2ccc3c(ccc4sc5c(c43)NC[C@H](C)NC5=O)n2)n1] |
| I-46 | 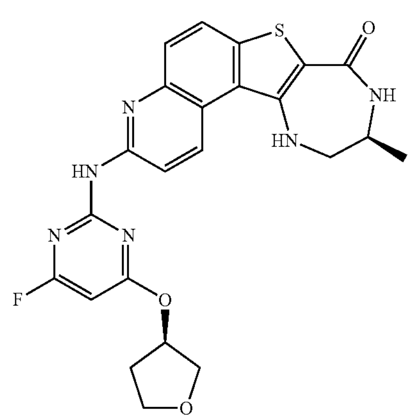 [SMILES: C[C@H]1CNc2c(sc3ccc4nc(Nc5nc(F)cc(O[C@@H]6CCOC6)n5)ccc4c23)C(=O)N1] |

TABLE 1-continued

| Compound # | Structure |
|---|---|
| I-47 | 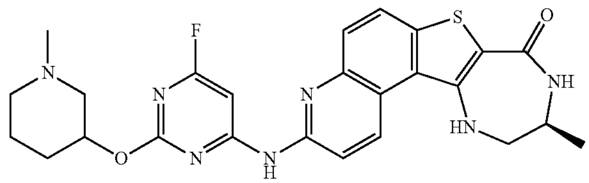 [SMILES: C[C@H]1CNc2c(sc3ccc4nc(Nc5cc(F)nc(OC6CCCN(C)C6)n5)ccc4c23)C(=O)N1] |
| I-48 | 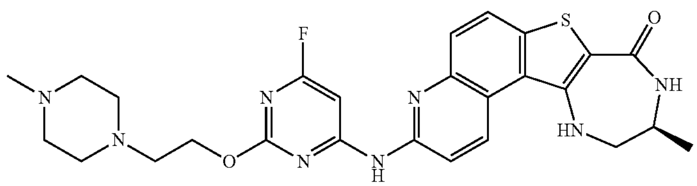 |
| I-49 | 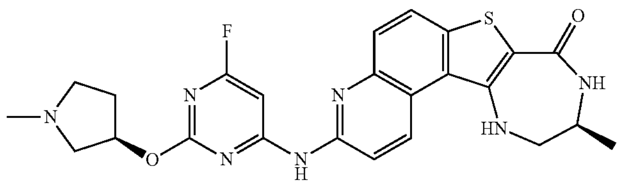 |
| I-50 | 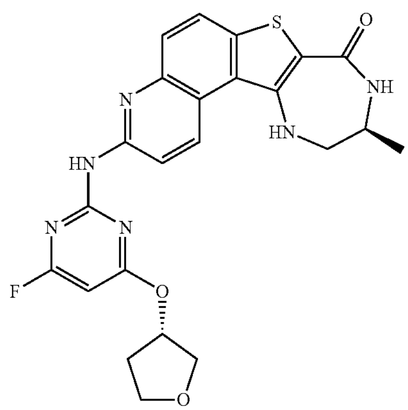 [SMILES: C[C@H]1CNc2c(sc3ccc4nc(Nc5nc(F)cc(O[C@H]6CCOC6)n5)ccc4c23)C(=O)N1] |
| I-51 | 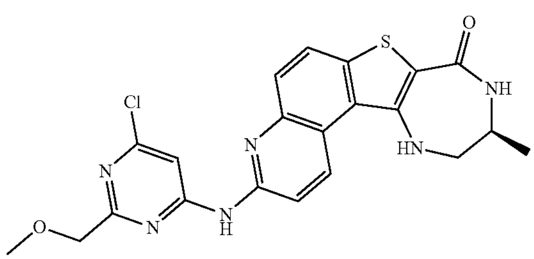 |
| I-52 | 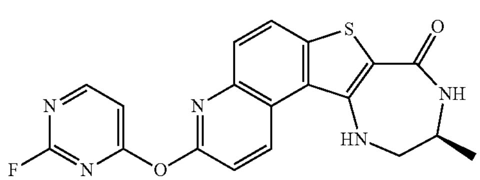 [SMILES: C[C@H]1CNc2c(sc3ccc4nc(Oc5ccnc(F)n5)ccc4c23)C(=O)N1] |
| I-53 | 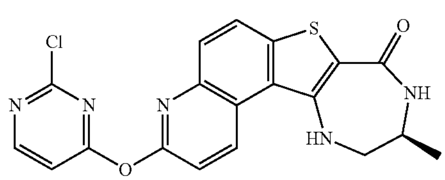 [SMILES: C[C@H]1CNc2c(sc3ccc4nc(Oc5ccnc(Cl)n5)ccc4c23)C(=O)N1] |

TABLE 1-continued

| Compound # | Structure |
|---|---|
| I-54 | 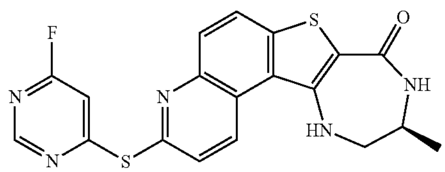 [SMILES: C[C@H]1CNc2c(sc3ccc4nc(Sc5cc(F)ncn5)ccc4c23)C(=O)N1] |
| I-55 | 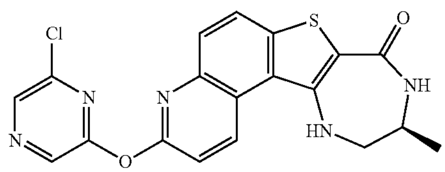 [SMILES: C[C@H]1CNc2c(sc3ccc4nc(Oc5cncc(Cl)n5)ccc4c23)C(=O)N1] |
| I-56 | 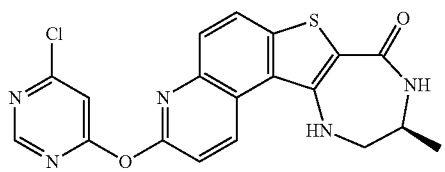 |
| I-57 | 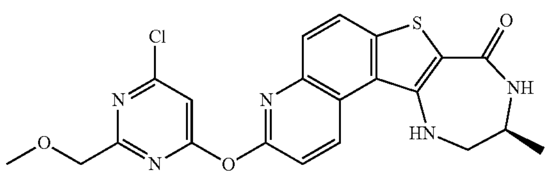 |
| I-58 | 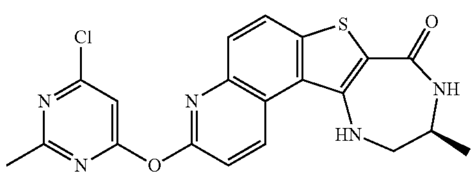 |
| I-59 | 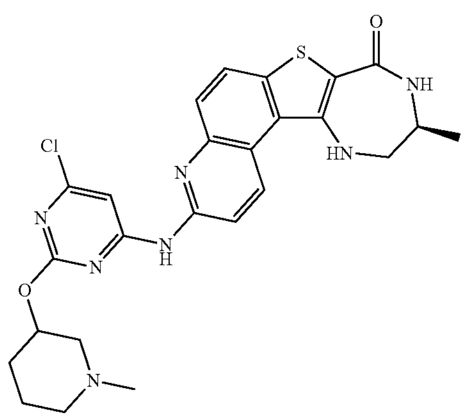 [SMILES: C[C@H]1CNc2c(sc3ccc4nc(Nc5cc(Cl)nc(OC6CCCN(C)C6)n5)ccc4c23)C(=O)N1] |
| I-60 | 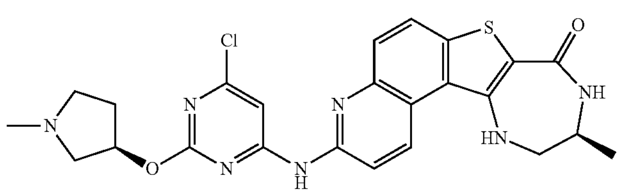 |

TABLE 1-continued

| Compound # | Structure |
|---|---|
| I-61 | 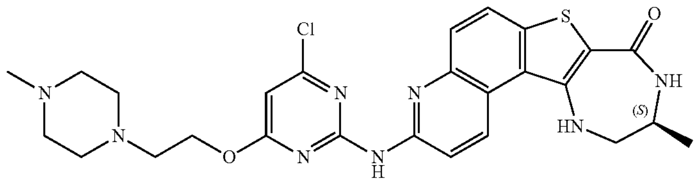 |
| I-62 | 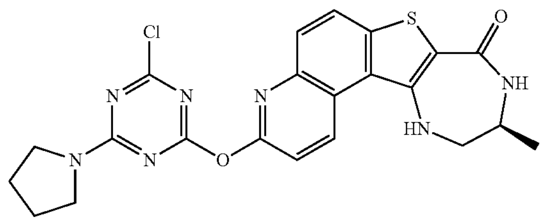 [SMILES: C[C@H]1CNc2c(sc3ccc4nc(Oc5nc(Cl)nc(N6CCCC6)n5)ccc4c23)C(=O)N1] |
| I-63 | 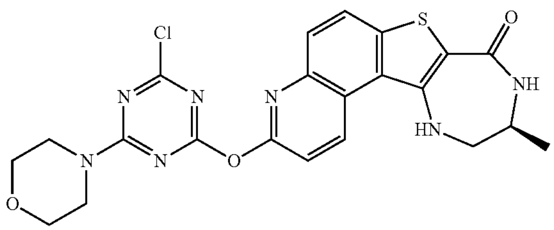 [SMILES: C[C@H]1CNc2c(sc3ccc4nc(Oc5nc(Cl)nc(N6CCOCC6)n5)ccc4c23)C(=O)N1] |
| I-64 | 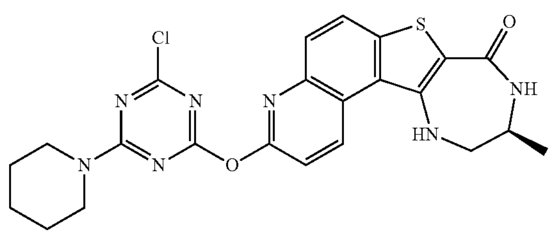 [SMILES: C[C@H]1CNc2c(sc3ccc4nc(Oc5nc(Cl)nc(N6CCCCC6)n5)ccc4c23)C(=O)N1] |
| I-65 | 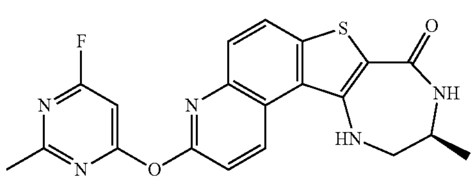 |
| I-66 | 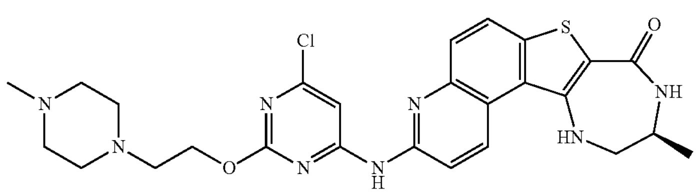 |
| I-67 | 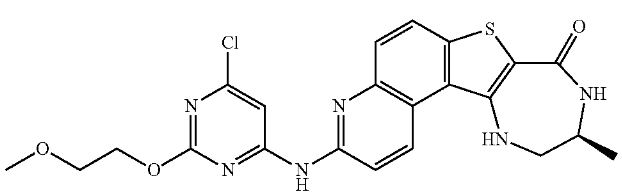 |

TABLE 1-continued

| Compound # | Structure |
|---|---|
| I-68 | 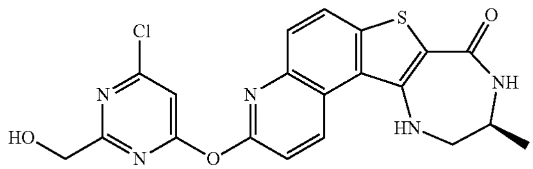 [SMILES: C[C@H]1CNc2c(sc3ccc4nc(Oc5cc(Cl)nc(CO)n5)ccc4c23)C(=O)N1] |
| I-69 | 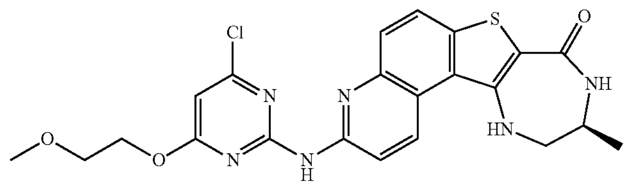 |
| I-70 | 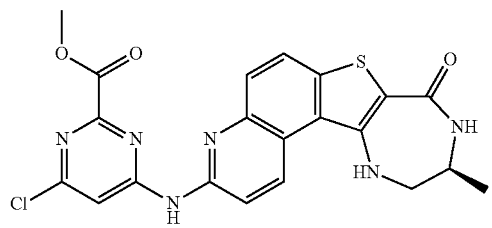 [SMILES: COC(=O)c1nc(Cl)cc(Nc2ccc3c(ccc4sc5c(c43)NC[C@H](C)NC5=O)n2)n1] |
| I-71 | 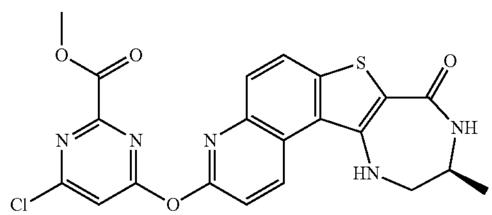 [SMILES: COC(=O)c1nc(Cl)cc(Oc2ccc3c(ccc4sc5c(c43)NC[C@H](C)NC5=O)n2)n1] |
| I-72 | 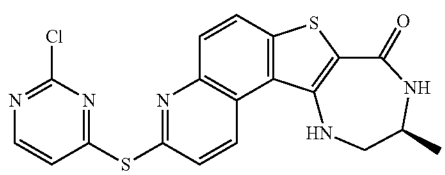 [SMILES: C[C@H]1CNc2c(sc3ccc4nc(Sc5ccnc(Cl)n5)ccc4c23)C(=O)N1] |
| I-73 | 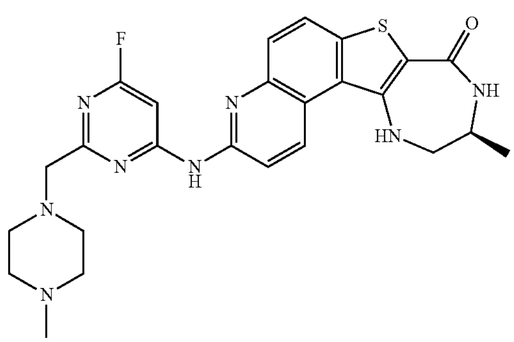 [SMILES: C[C@H]1CNc2c(sc3ccc4nc(Nc5cc(F)nc(CN6CCN(C)CC6)n5)ccc4c23)C(=O)N1] |
| I-74 | 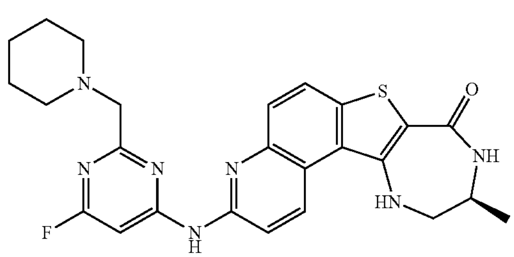 [SMILES: C[C@H]1CNc2c(sc3ccc4nc(Nc5cc(F)nc(CN6CCCCC6)n5)ccc4c23)C(=O)N1] |

TABLE 1-continued

| Compound # | Structure |
|---|---|
| I-75 | 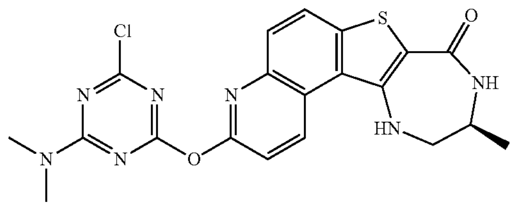 |
| I-76 | 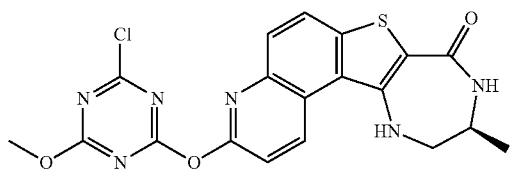 |
| I-77 | 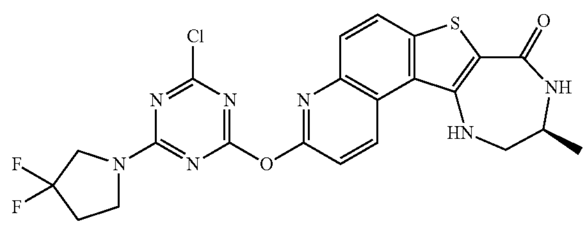 [SMILES: C[C@H]1CNc2c(sc3ccc4nc(Oc5nc(Cl)nc(N6CCC(F)(F)C6)n5)ccc4c23)C(=O)N1] |
| I-78 | 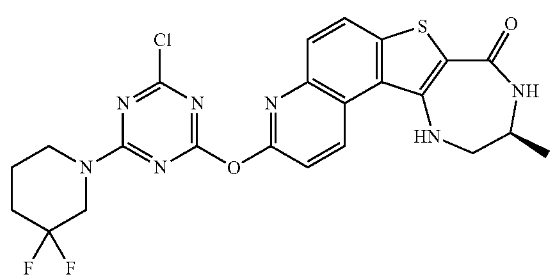 [SMILES: C[C@H]1CNc2c(sc3ccc4nc(Oc5nc(Cl)nc(N6CCCC(F)(F)C6)n5)ccc4c23)C(=O)N1] |
| I-79 | 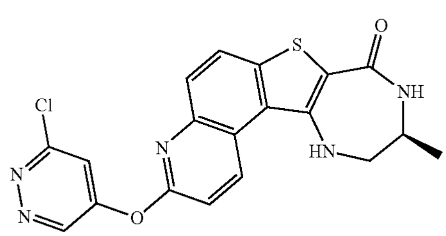 [SMILES: C[C@H]1CNc2c(sc3ccc4nc(Oc5cnnc(Cl)c5)ccc4c23)C(=O)N1] |
| I-80 | 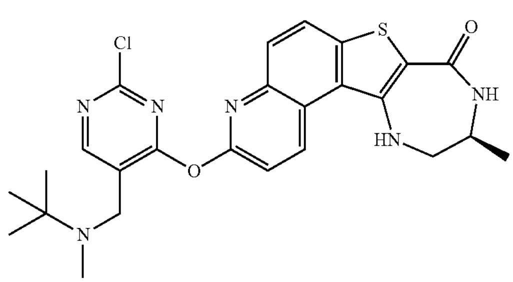 [SMILES: C[C@H]1CNc2c(sc3ccc4nc(Oc5nc(Cl)ncc5CN(C)C(C)(C)C)ccc4c23)C(=O)N1] |

TABLE 1-continued

| Compound # | Structure |
|---|---|
| I-81 | 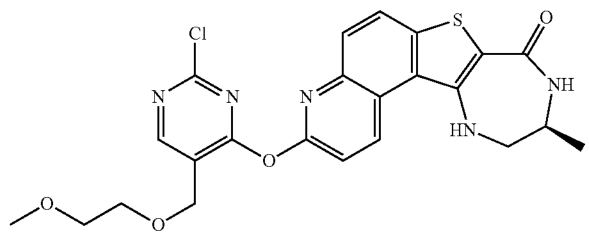 |
| I-82 | 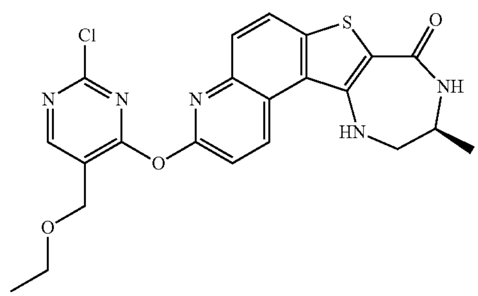 |
| I-83 | 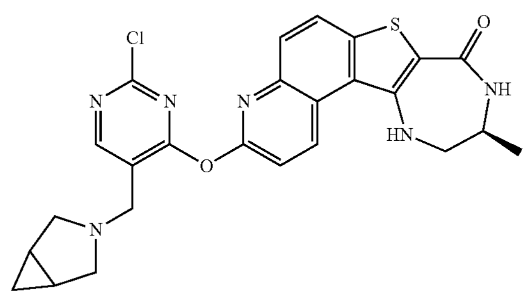 [SMILES: C[C@H]1CNc2c(sc3ccc4nc(Oc5nc(Cl)ncc5CN5CC6CC6C5)ccc4c23)C(=O)N1] |
| I-84 | 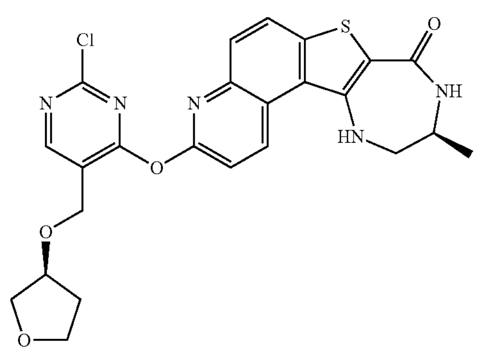 [SMILES: C[C@H]1CNc2c(sc3ccc4nc(Oc5nc(Cl)ncc5CO[C@H]5CCOC5)ccc4c23)C(=O)N1] |
| I-85 | 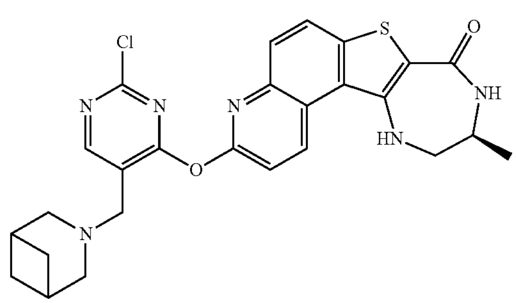 [SMILES: C[C@H]1CNc2c(sc3ccc4nc(Oc5nc(Cl)ncc5CN5CC6CC(C6)C5)ccc4c23)C(=O)N1] |

TABLE 1-continued

| Compound # | Structure |
|---|---|
| I-86 | 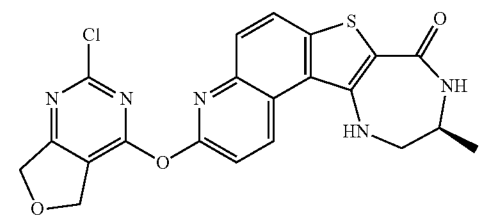 [SMILES: C[C@H]1CNc2c(sc3ccc4nc(Oc5nc(Cl)nc6c5COC6)ccc4c23)C(=O)N1] |
| I-87 | 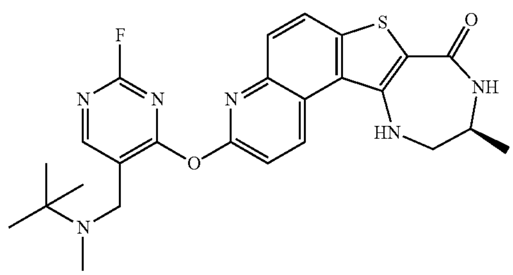 [SMILES: C[C@H]1CNc2c(sc3ccc4nc(Oc5nc(F)ncc5CN(C)C(C)(C)C)ccc4c23)C(=O)N1] |
| I-88 | 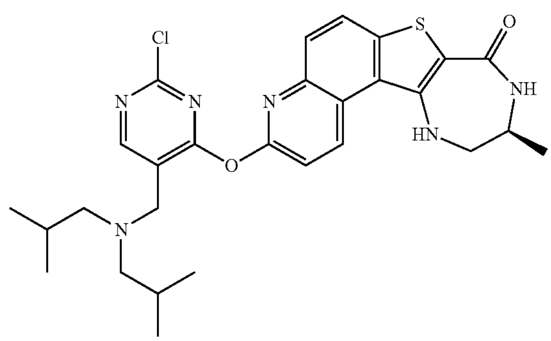 [SMILES: CC(C)CN(Cc1cnc(Cl)nc1Oc1ccc2c(ccc3sc4c(c32)NC[C@H](C)NC4=O)n1)CC(C)C] |
| I-89 | 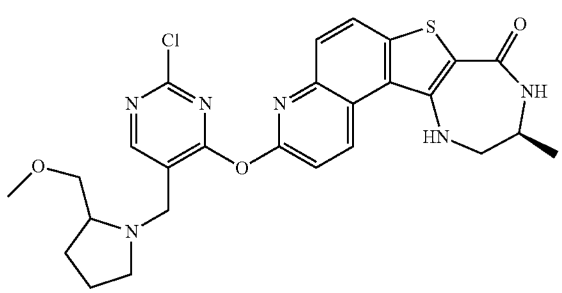 |
| I-90 | 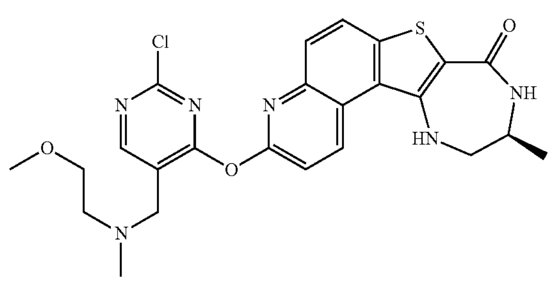 |

TABLE 1-continued

| Compound # | Structure |
|---|---|
| I-91 | 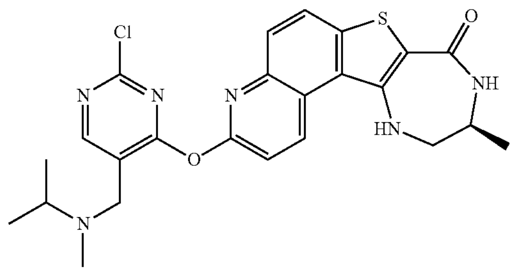 [SMILES: CC(C)N(C)Cc1cnc(Cl)nc1Oc1ccc2c(ccc3sc4c(c32)NC[C@H](C)NC4=O)n1] |
| I-92 | 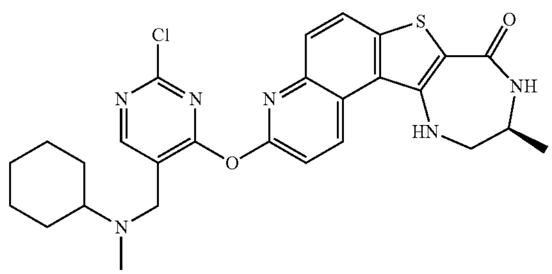 [SMILES: C[C@H]1CNc2c(sc3ccc4nc(Oc5nc(Cl)ncc5CN(C)C5CCCCC5)ccc4c23)C(=O)N1] |
| I-93 | 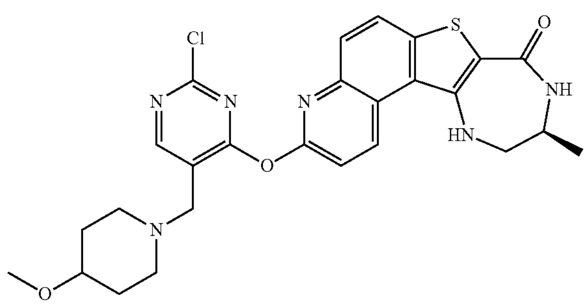 |
| I-94 | 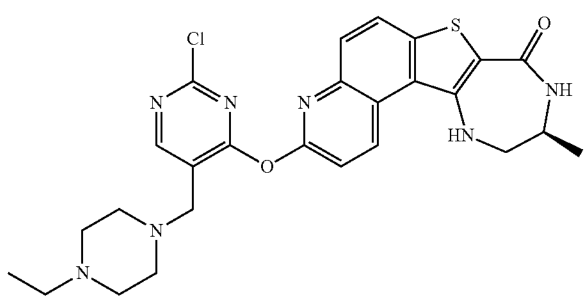 [SMILES: CCN1CCN(Cc2cnc(Cl)nc2Oc2ccc3c(ccc4sc5c(c43)NC[C@H](C)NC5=O)n2)CC1] |
| I-95 | 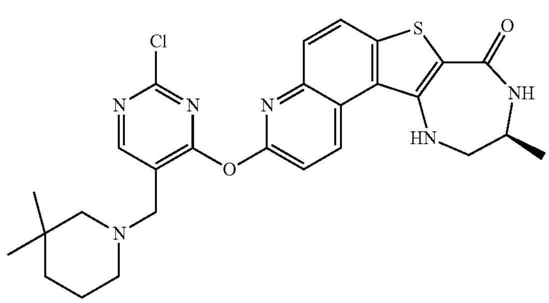 |

TABLE 1-continued

| Compound # | Structure |
|---|---|
| I-96 | 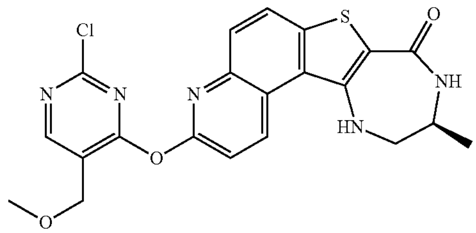 |
| I-97 | 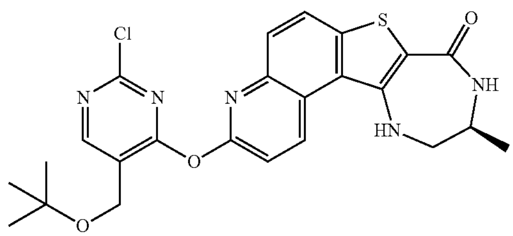 [SMILES: C[C@H]1CNc2c(sc3ccc4nc(Oc5nc(Cl)ncc5COC(C)(C)C)ccc4c23)C(=O)N1] |
| I-98 | 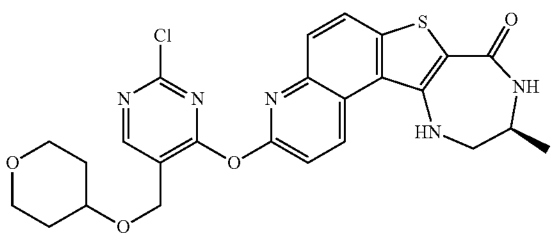 [SMILES: C[C@H]1CNc2c(sc3ccc4nc(Oc5nc(Cl)ncc5COC5CCOCC5)ccc4c23)C(=O)N1] |
| I-99 | 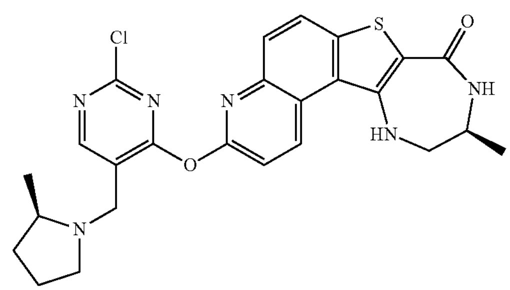 [SMILES: C[C@@H]1CCCN1Cc1cnc(Cl)nc1Oc1ccc2c(ccc3sc4c(c32)NC[C@H](C)NC4=O)n1] |
| I-100 | 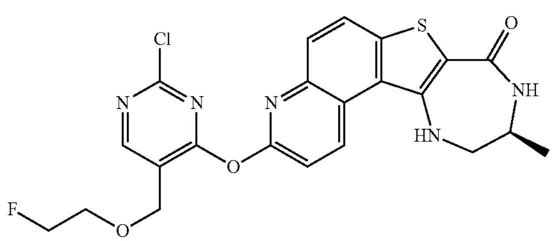 [SMILES: C[C@H]1CNc2c(sc3ccc4nc(Oc5nc(Cl)ncc5COCCF)ccc4c23)C(=O)N1] |
| I-101 | 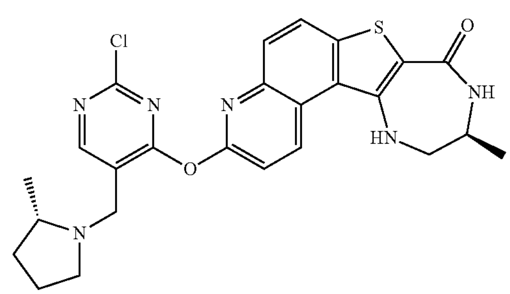 [SMILES: C[C@H]1CNc2c(sc3ccc4nc(Oc5nc(Cl)ncc5CN5CCC[C@@H]5C)ccc4c23)C(=O)N1] |

TABLE 1-continued

| Compound # | Structure |
|---|---|
| I-102 | 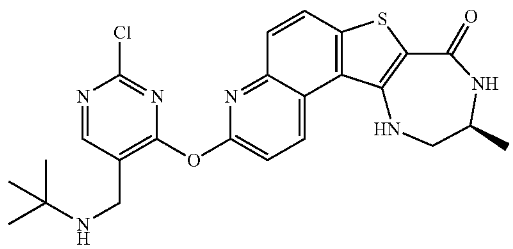 [SMILES: C[C@H]1CNc2c(sc3ccc4nc(Oc5nc(Cl)ncc5CNC(C)(C)C)ccc4c23)C(=O)N1] |
| I-103 | 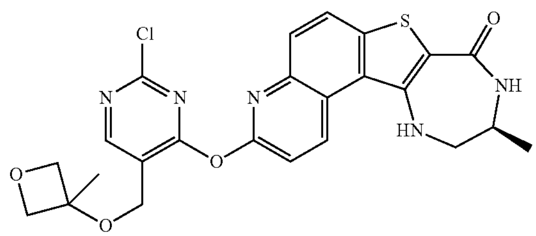 [SMILES: C[C@H]1CNc2c(sc3ccc4nc(Oc5nc(Cl)ncc5COC5(C)COC5)ccc4c23)C(=O)N1] |
| I-104 | 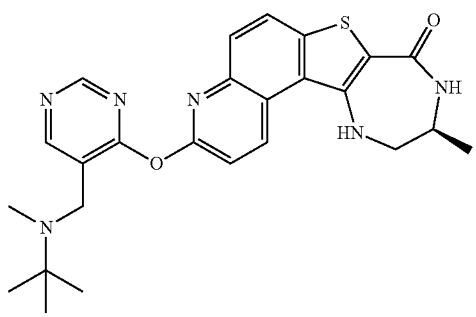 |
| I-105 | 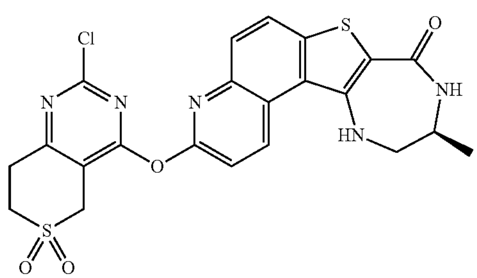 [SMILES: C[C@H]1CNc2c(sc3ccc4nc(Oc5nc(Cl)nc6c5CS(=O)(=O)CC6)ccc4c23)C(=O)N1] |
| I-106 | 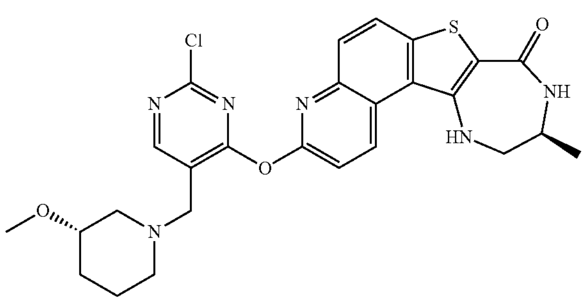 |

TABLE 1-continued

| Compound # | Structure |
| --- | --- |
| I-107 | 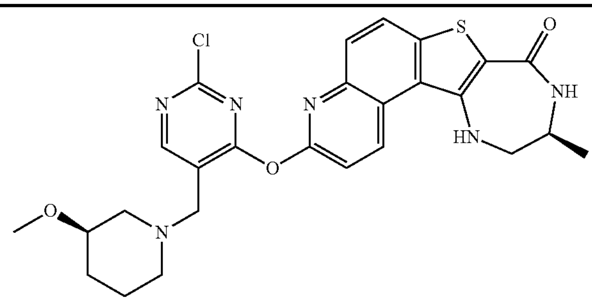 |
| I-108 | 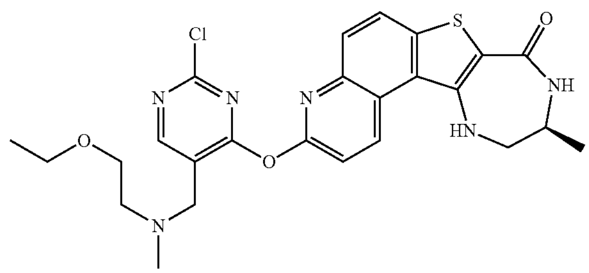 [SMILES: CCOCCN(C)Cc1cnc(Cl)nc1Oc1ccc2c(ccc3sc4c(c32)NC[C@H](C)NC4=O)n1] |
| I-109 | 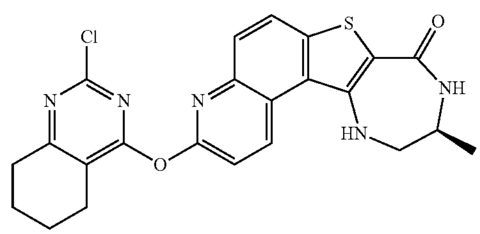 [SMILES: C[C@H]1CNc2c(sc3ccc4nc(Oc5nc(Cl)nc6c5CCCC6)ccc4c23)C(=O)N1] |
| I-110 | 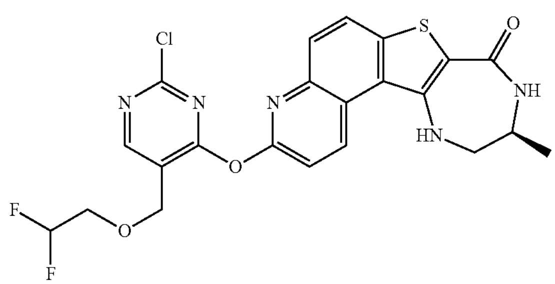 [SMILES: C[C@H]1CNc2c(sc3ccc4nc(Oc5nc(Cl)ncc5COCC(F)F)ccc4c23)C(=O)N1] |
| I-111 | 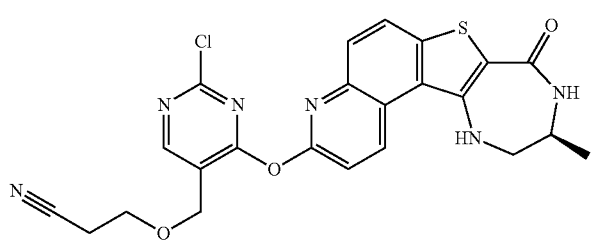 [SMILES: C[C@H]1CNc2c(sc3ccc4nc(Oc5nc(Cl)ncc5COCCC#N)ccc4c23)C(=O)N1] |
| I-112 | 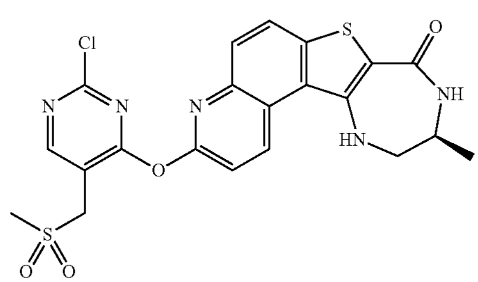 |

TABLE 1-continued

| Compound # | Structure |
|---|---|
| I-113 | 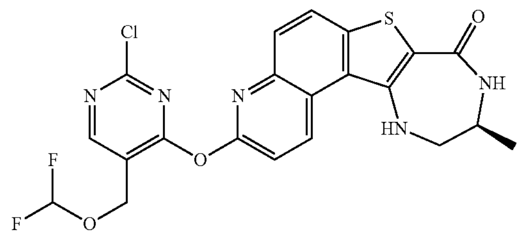 [SMILES: C[C@H]1CNc2c(sc3ccc4nc(Oc5nc(Cl)ncc5COC(F)F)ccc4c23)C(=O)N1] |
| I-114 | 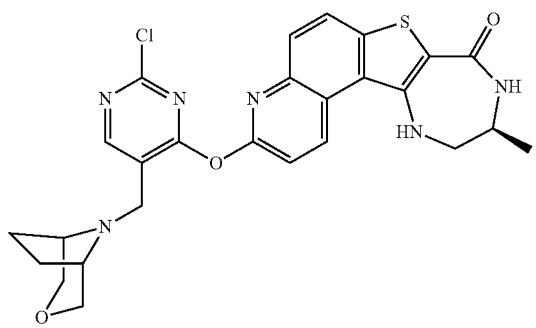 [SMILES: C[C@H]1CNc2c(sc3ccc4nc(Oc5nc(Cl)ncc5CN5C6CCC5COC6)ccc4c23)C(=O)N1] |
| I-115 | 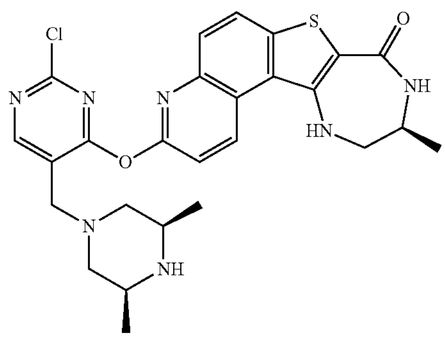 [SMILES: C[C@@H]1CN(Cc2cnc(Cl)nc2Oc2ccc3c(ccc4sc5c(c43)NC[C@H](C)NC5=O)n2)C[C@H](C)N1] |
| I-116 | 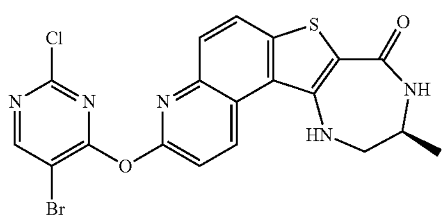 [SMILES: C[C@H]1CNc2c(sc3ccc4nc(Oc5nc(Cl)ncc5Br)ccc4c23)C(=O)N1] |
| I-117 | 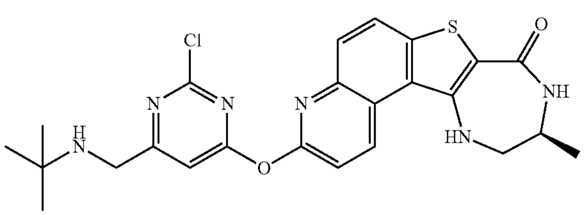 [SMILES: C[C@H]1CNc2c(sc3ccc4nc(Oc5cc(CNC(C)(C)C)nc(Cl)n5)ccc4c23)C(=O)N1] |
| I-118 | 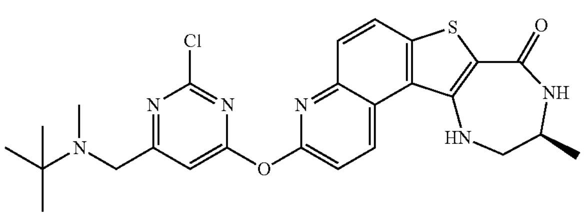 [SMILES: C[C@H]1CNc2c(sc3ccc4nc(Oc5cc(CN(C)C(C)(C)C)nc(Cl)n5)ccc4c23)C(=O)N1] |

TABLE 1-continued

| Compound # | Structure |
|---|---|
| I-119 | 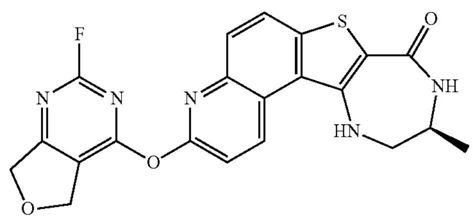 |
| I-120 | 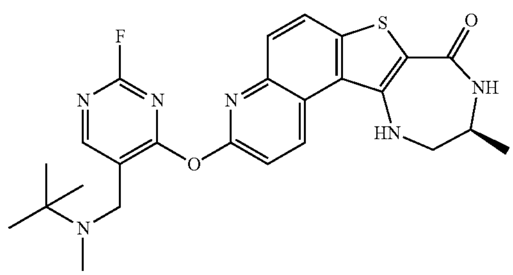 [SMILES: C[C@H]1CNc2c(sc3ccc4nc(Oc5nc(F)ncc5CN(C)C(C)(C)C)ccc4c23)C(=O)N1] |
| I-121 | 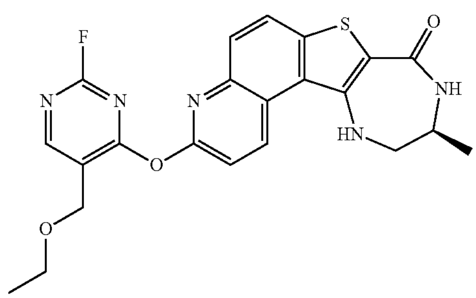 |
| I-122 | 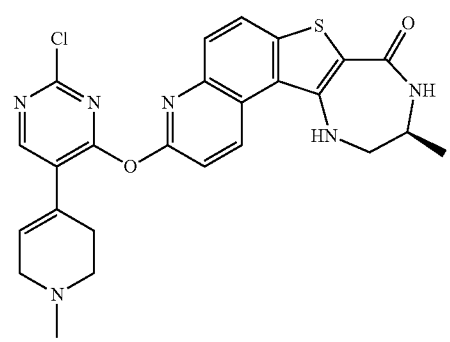 [SMILES: C[C@H]1CNc2c(sc3ccc4nc(Oc5nc(Cl)ncc5C5=CCN(C)CC5)ccc4c23)C(=O)N1] |
| I-123 | 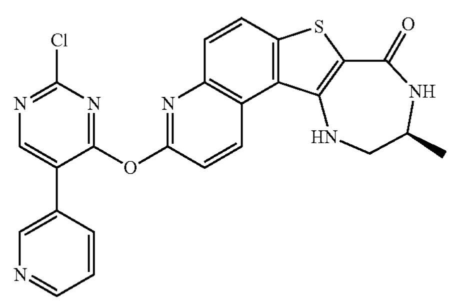 [SMILES: C[C@H]1CNc2c(sc3ccc4nc(Oc5nc(Cl)ncc5-c5cccnc5)ccc4c23)C(=O)N1] |

TABLE 1-continued
| Compound # | Structure |
|---|---|
| I-124 | 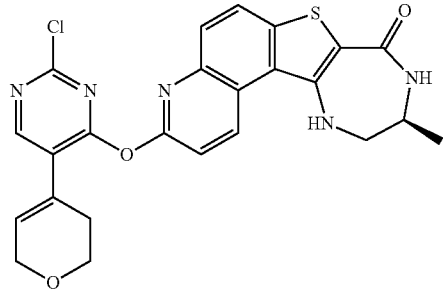 [SMILES: C[C@H]1CNc2c(sc3ccc4nc(Oc5nc(Cl)ncc5C5=CCOCC5)ccc4c23)C(=O)N1] |
| I-125 | 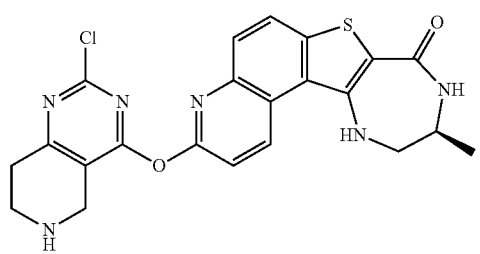 [SMILES: C[C@H]1CNc2c(sc3ccc4nc(Oc5nc(Cl)nc6c5CNCC6)ccc4c23)C(=O)N1] |
| I-126 | 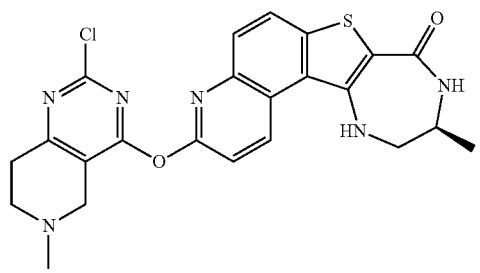 [SMILES: C[C@H]1CNc2c(sc3ccc4nc(Oc5nc(Cl)nc6c5CN(C)CC6)ccc4c23)C(=O)N1] |
| I-127 | 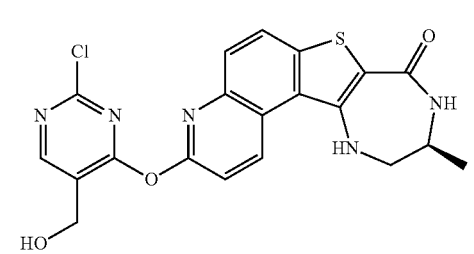 [SMILES: C[C@H]1CNc2c(sc3ccc4nc(Oc5nc(Cl)ncc5CO)ccc4c23)C(=O)N1] |
| I-128 | 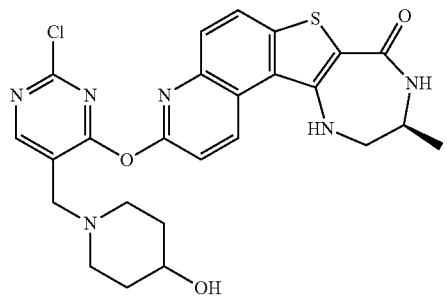 [SMILES: C[C@H]1CNc2c(sc3ccc4nc(Oc5nc(Cl)ncc5CN5CCC(O)CC5)ccc4c23)C(=O)N1] |

TABLE 1-continued
| Compound # | Structure |
|---|---|
| I-129 | 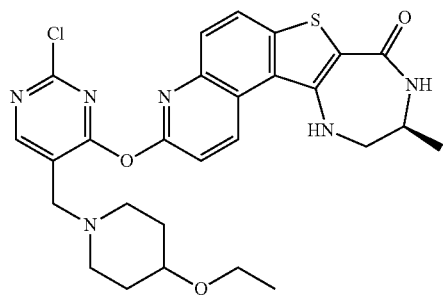 [SMILES: CCOC1CCN(Cc2cnc(Cl)nc2Oc2ccc3c(ccc4sc5c(c43)NC[C@H](C)NC5=O)n2)CC1] |
| I-130 | 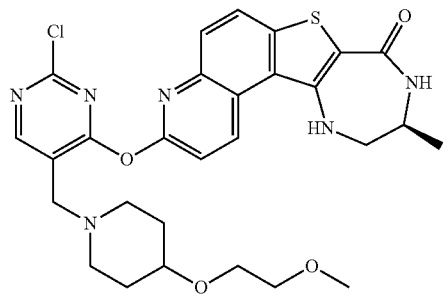 [SMILES: COCCOC1CCN(Cc2cnc(Cl)nc2Oc2ccc3c(ccc4sc5c(c43)NC[C@H](C)NC5=O)n2)CC1] |
| I-131 | 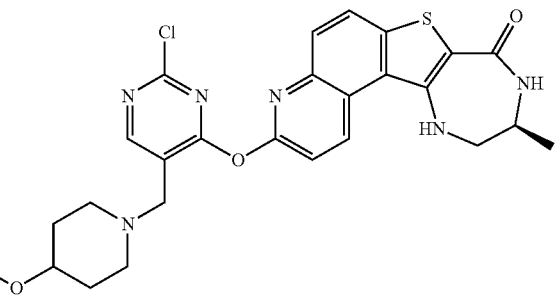 |
| I-132 | 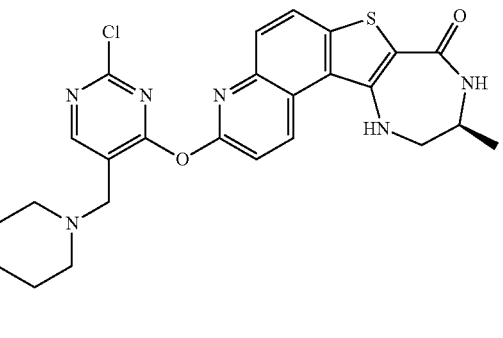 |
| I-133 | 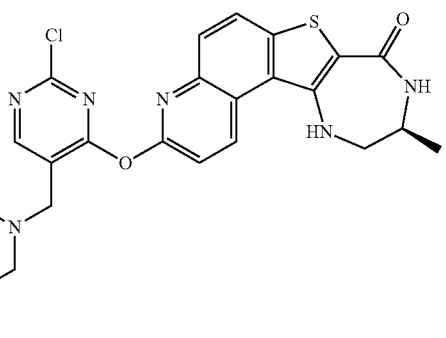 |

TABLE 1-continued

| Compound # | Structure |
|---|---|
| I-134 | 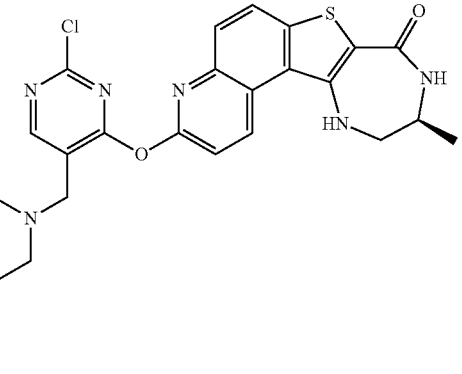 |
| I-135 | 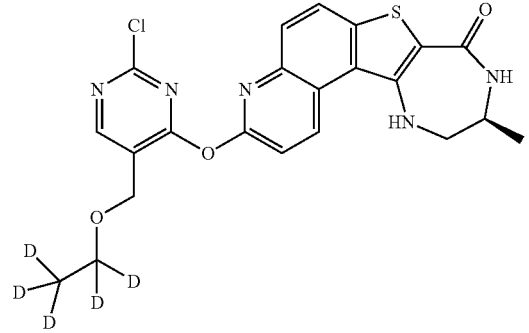 [SMILES: [2H]C([2H])([2H])C([2H])([2H])OCc1cnc(Cl)nc1Oc1ccc2c(ccc3sc4c(c32)NC[C@H](C)NC4=O)n1] |

In some embodiments, the present invention provides a compound depicted in Table 1, or a pharmaceutically acceptable salt thereof.

4. Uses, Formulation and Administration

Pharmaceutically Acceptable Compositions

According to another embodiment, the invention provides a composition comprising a compound of this invention or a pharmaceutically acceptable salt thereof and a pharmaceutically acceptable carrier, adjuvant, or vehicle. In certain embodiments, the amount of compound in compositions of this invention is such that it is effective to measurably inhibit MK2, or a mutant thereof, in a biological sample or in a patient. In certain embodiments, a composition of this invention is formulated for administration to a patient in need of such composition. In some embodiments, a composition of this invention is formulated for oral administration to a patient.

Compounds and compositions, according to method of the present invention, are administered using any amount and any route of administration effective for treating or lessening the severity of a disorder provided herein (i.e., an MK2-mediated disease or disorder). The exact amount required will vary from subject to subject, depending on the species, age, and general condition of the subject, the severity of the infection, the particular agent, its mode of administration, and the like. Compounds of the invention are preferably formulated in unit dosage form for ease of administration and uniformity of dosage.

Compositions of the present invention may be administered orally, parenterally, by inhalation spray, topically, rectally, nasally, buccally, vaginally, intraperitoneally, intracisternally or via an implanted reservoir. In some embodiments, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In some embodiments, provided pharmaceutically acceptable compositions are formulated for oral administration. Such formulations may be administered with or without food. In some embodiments, pharmaceutically acceptable compositions of this invention are administered without food. In other embodiments, pharmaceutically acceptable compositions of this invention are administered with food. Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and/or i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Uses of Compounds and Pharmaceutically Acceptable Compositions

Compounds and compositions described herein are generally useful for the inhibition of kinase activity of one or more enzymes. Examples of kinases that are inhibited by the compounds and compositions described herein and against which the methods described herein are useful include MK2, or a mutant thereof.

The activity of a compound utilized in this invention as an inhibitor of a MK2 kinase, or a mutant thereof, may be assayed in vitro, in vivo or in a cell line. In vitro assays include assays that determine inhibition of either the phosphorylation activity and/or the subsequent functional consequences, or ATPase activity of activated MK2 kinase, or a mutant thereof. Alternate in vitro assays quantitate the ability of the test compound to bind to MK2. Inhibitor binding may be measured by radiolabeling the test compound prior to binding, isolating the test compound/MK2 complex and determining the amount of radiolabel bound. Alternatively, inhibitor binding may be determined by running a competition experiment where test compounds are incubated with MK2 kinase bound to known radioligands. Detailed conditions for assaying a compound utilized in this invention as an inhibitor of MK2, or a mutant thereof, are set forth in the Examples, below.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting MK2 kinase, or a mutant thereof, activity in a biological sample comprising the step of contacting said biological sample with a compound of this invention, or a composition comprising said compound. In certain embodiments, the invention relates to a method of irreversibly inhibiting MK2 kinase, or a mutant thereof, activity in a biological sample comprising the step of contacting said biological sample with a compound of this invention, or a composition comprising said compound.

According to another embodiment, the invention relates to a method of inhibiting MK2 kinase, or a mutant thereof, activity in a patient comprising the step of administering to said patient a compound of the present invention, or a composition comprising said compound. According to certain embodiments, the invention relates to a method of irreversibly inhibiting MK2 kinase, or a mutant thereof, activity in a patient comprising the step of administering to said patient a compound of the present invention, or a composition comprising said compound. In other embodiments, the present invention provides a method for treating an MK2-mediated disease or disorder, in a patient in need thereof, comprising the step of administering to said patient a compound according to the present invention or pharmaceutically acceptable composition thereof. Such disorders are described in detail herein.

MK2 Kinase

MAP kinase-activated protein kinase 2 ("MK2") is an enzyme that in humans is encoded by the MAPKAPK2 gene. The MAPKAPK2 gene encodes a member of the Ser/Thr protein kinase family and two transcript variants encoding two different isoforms have been found. MK2 is regulated through direct phosphorylation by p38 MAP kinase.

MK2 is a multi-domain protein consisting of an N-terminal proline-rich domain, a catalytic domain, an autoinhibitory domain and at the C-terminus a nuclear export signal (NES) and nuclear localization signal (NLS). Two isoforms of human MK2 have been characterized. One isoform consists of 400 amino acids and the other isoform 370 residues which is thought to be a splice variant missing the C-terminal NLS.

MK2 is known to be involved in many cellular processes including stress and inflammatory responses, nuclear export, gene expression regulation and cell proliferation. Indeed, MK2 regulates, by a post-transcriptional mechanism, biosynthesis of tumor necrosis factor α (TNFα) that is overproduced in inflammatory diseases such as rheumatoid arthritis and inflammatory bowel disease. See Natesan et al., J. Med. Chem. 2012, 55, 2035-2047.

Inhibition of Hsp27 phosphorylation occurs by inhibiting the formation of the p38 kinase-MK2-Hsp27 signaling complex. Phosphorylation of Hsp27 is the penultimate event in a complex signaling cascade that occurs in response to extracellular stimuli. See Zheng et al., *The Journal of Biological Chemistry*, vol. 281, no. 48, 37215-37226, Dec. 1, 2006. Hsp27 usually exists as oligomers and plays a role in regulation of many cellular functions such as inhibition of the death receptor-mediated apoptosis, promotion of proper refolding of denatured proteins by acting as a molecular chaperone, and regulation of cytoskeleton. The presence of MK2 is a necessary condition for the formation of p38 kinase-MK2-Hsp27 signaling complex in cells. See Zheng et al., *The Journal of Biological Chemistry*, vol. 281, no. 48, 37215-37226, Dec. 1, 2006.

Evidence suggests that many signaling proteins form multimeric complexes. See Zheng et al., *The Journal of Biological Chemistry*, vol. 281, no. 48, 37215-37226, Dec. 1, 2006. One such complex is the Hsp27/Akt (a serine/threonine kinase) dimer, which forms in the cytoplasm of a cell. Another complex is formed between MK2 and p38. See Ben-Levy et al., Current Biology 1998, 8:1049-1057; Natesan et al., J Med. Chem. 2012, 55, 2035-2047; Zheng et al., *The Journal of Biological Chemistry*, vol. 281, no. 48, 37215-37226, Dec. 1, 2006.

In unstimulated conditions, inactive p38 and unphosphorylated MK2 form such dimer in the nucleus of a cell. Upon activation, p38 phosphorylates MK2, thereby inducing a conformational change of the autoinhibitory domain of MK2 and exposing the active site for substrate binding. Once MK2 is phosphorylated, the p38-MK2 dimer is translocated to the cytoplasm, where it forms a quaternary complex with the Hsp27-Akt dimer. See Zheng et al., *The Journal of Biological Chemistry*, vol. 281, no. 48, 37215-37226, Dec. 1, 2006. Hsp27 is then phosphorylated by MK2, resulting in degradation of the quaternary complex and the release of p-Hsp27 monomers and dimers. Because inhibition of MK2 blocks phosphorylation of Hsp27, without wishing to be bound by theory, it is believed that inhibition of MK2 prevents degradation of the p38-MK2-Akt-Hsp27 quaternary complex, thereby altering downstream effects. Consequent to the inhibition of quaternary complex degradation, the amount of quaternary complex would thereby increase. Moreover, the equilibrium of p38 and MK2 between the cytoplasm and nucleus would be shifted towards the cytoplasm.

Interestingly, transport of the MK2/p38 complex out of the nucleus does not require catalytically active MK2, as the active site mutant, Asp207Ala, is still transported to the cytoplasm. Phosphorylation of human MK2 by p38 on residues T222, S272 and T334 is thought to activate the enzyme by inducing a conformational change of the autoinhibitory domain thus exposing the active site for substrate binding. Mutations of two autoinhibitory domain residues W332A and K326E in murine MK2 demonstrate an increase in basal activity and a C-terminal deletion of the autoinhibitory domain renders the enzyme constitutively active, providing additional evidence to the role of this domain in inhibition of MK2 activity.

Diseases or disorders associated with MK2 that are treated by compounds of the present invention include autoimmune disorders, chronic inflammatory disorders, acute inflammatory disorders, auto-inflammatory disorders, fibrotic disorders, metabolic disorders, neoplasias, or cardiovascular or cerebrovascular disorders. Thus, in some embodiments, the present invention provides a method for treating an MK2-mediated disease or disorder in a patient in need thereof, wherein said method comprises administering to said patient a therapeutically effective amount of a provided compound, or composition thereof. Such MK2-mediated diseases or disorders include, but are not limited to those described herein.

In some embodiments, the MK2-mediated disease or disorder is an autoimmune disorder, chronic and/or acute inflammatory disorder, and/or auto-inflammatory disorder. Exemplary autoimmune and/or inflammatory and/or auto-inflammatory disorders include: inflammatory bowel diseases (for example, ulcerative colitis or Crohn's disease), multiple sclerosis, psoriasis, arthritis, rheumatoid arthritis, osteoarthritis, juvenile arthritis, psoriatic arthritis, reactive arthritis, ankylosing spondylitis, cryopyrin associated periodic syndromes, Muckle-Wells syndrome, familial cold auto-inflammatory syndrome, neonatal-onset multisystem inflammatory disease, TNF receptor associated periodic syndrome, acute and chronic pancreatitis, atherosclerosis, gout, ankylosing spondylitis, fibrotic disorders (for example, hepatic fibrosis or idiopathic pulmonary fibrosis), nephropathy, sarcoidosis, scleroderma, anaphylaxis, diabetes (for example, diabetes mellitus type 1 or diabetes mellitus type 2), diabetic retinopathy, Still's disease, vasculitis, sarcoidosis, pulmonary inflammation, acute respiratory distress syndrome, wet and dry age-related macular degeneration, autoimmune hemolytic syndromes, autoimmune and inflammatory hepatitis, autoimmune neuropathy, autoimmune ovarian failure, autoimmune orchitis, autoimmune thrombocytopenia, silicone implant associated autoimmune disease, Sjogren's syndrome, familial Mediterranean fever, systemic lupus erythematosus, vasculitis syndromes (for example, temporal, Takayasu's and giant cell arteritis, Behcet's disease or Wegener's granulomatosis), vitiligo, secondary hematologic manifestation of autoimmune diseases (for example, anemias), drug-induced autoimmunity, Hashimoto's thyroiditis, hypophysitis, idiopathic thrombocytic pupura, metal-induced autoimmunity, myasthenia gravis, pemphigus, autoimmune deafness (for example, Meniere's disease), Goodpasture's syndrome, Graves' disease, HW-related autoimmune syndromes, Guillain-Barre disease, Addison's disease, anti-phospholipid syndrome, asthma, atopic dermatitis, Celiac disease, Cushing's syndrome, dermatomyositis, idiopathic adrenal adrenal atrophy, idiopathic thrombocytopenia, Kawasaki syndrome, Lambert-Eaton Syndrome, pernicious anemia, pollinosis, polyarteritis *nodosa*, primary biliary cirrhosis, primary sclerosing cholangitis, Raynaud's, Reiter's Syndrome, relapsing polychondritis, Schmidt's syndrome, thyrotoxidosis, sepsis, septic shock, endotoxic shock, exotoxin-induced toxic shock, gram negative sepsis, toxic shock syndrome, glomerulonephritis, peritonitis, interstitial cystitis, hyperoxia-induced inflammations, chronic obstructive pulmonary disease (COPD), vasculitis, graft vs. host reaction (for example, graft vs. host disease), allograft rejections (for example, acute allograft rejection or chronic allograft rejection), early transplantation rejection (for example, acute allograft rejection), reperfusion injury, pain (for example, acute pain, chronic pain, neuropathic pain, or fibromyalgia), chronic infections, meningitis, encephalitis, myocarditis, gingivitis, post surgical trauma, tissue injury, traumatic brain injury, enterocolitis, sinusitis, uveitis, ocular inflammation, optic neuritis, gastric ulcers, esophagitis, peritonitis, periodontitis, dermatomyositis, gastritis, myositis, polymyalgia, pneumonia and bronchitis.

In some embodiments, the MK2-mediated disease or disorder is a fibrotic disorder. Exemplary fibrotic disorders include systemic sclerosis/scleroderma, lupus nephritis, connective tissue disease, wound healing, surgical scarring, spinal cord injury, CNS scarring, acute lung injury, pulmonary fibrosis (for example, idiopathic pulmonary fibrosis or cystic fibrosis), chronic obstructive pulmonary disease, adult respiratory distress syndrome, acute lung injury, drug-induced lung injury, glomerulonephritis, chronic kidney disease (for example, diabetic nephropathy), hypertension-induced nephropathy, alimentary track or gastrointestinal fibrosis, renal fibrosis, hepatic or biliary fibrosis, liver fibrosis (for example, nonalcoholic steatohepatitis, hepatitis C, or hepatocellular carcinoma), cirrhosis (for example, primary biliary cirrhosis or cirrhosis due to fatty liver disease (for example, alcoholic and nonalcoholic steatosis)), radiation-induced fibrosis (for example, head and neck, gastrointestinal or pulmonary), primary sclerosing cholangitis, restenosis, cardiac fibrosis (for example, endomyocardial fibrosis or atrial fibrosis), opthalmic scarring, fibrosclerosis, fibrotic cancers, fibroids, fibroma, fibroadenomas, fibrosarcomas, transplant arteriopathy, keloid, mediastinal fibrosis, myelofibrosis, retroperitoneal fibrosis, progressive massive fibrosis, and nephrogenic systemic fibrosis.

In some embodiments, the MK2-mediated disease or disorder is a metabolic disorder. Exemplary metabolic disorders include obesity, steroid-resistance, glucose intolerance, and metabolic syndrome.

In some embodiments, the MK2-mediated disease or disorder is a neoplasia. Exemplary neoplasias include cancers. In some embodiments, exemplary neoplasias include angiogenesis disorders, multiple myeloma, leukemias (for example, acute lymphocytic leukemia, acute and chronic myelogenous leukemia, chronic lymphocytic leukemia, acute lymphoblastic leukemia, or promyelocytic leukemia), lymphomas (for example, B-cell lymphoma, T-cell lymphoma, mantle cell lymphoma, hairy cell lymphoma, Burkitt's lymphoma, mast cell tumors, Hodgkin's disease or non-Hodgkin's disease), myelodysplastic syndrome, fibrosarcoma, rhabdomyosarcoma; astrocytoma, neuroblastoma, glioma and schwannomas; melanoma, seminoma, teratocarcinoma, osteosarcoma, xenoderma pigmentosum, keratoctanthoma, thyroid follicular cancer, Kaposi's sarcoma, melanoma, teratoma, rhabdomyosarcoma, metastatic and bone disorders, as well as cancer of the bone, mouth/pharynx, esophagus, larynx, stomach, intestine, colon, rectum, lung (for example, non-small cell lung cancer or small cell lung cancer), liver, pancreas, nerve, brain (for example, glioma or glioblastoma multiforme), head and neck, throat, ovary, uterus, prostate, testis, bladder, kidney, breast, gall bladder, cervix, thyroid, prostate, and skin.

In some embodiments, the MK2-mediated disorder is a cardiovascular or cerebrovascular disorder. Exemplary cardiovascular disorders include atherosclerosis, restenosis of an atherosclerotic coronary artery, acute coronary syndrome, myocardial infarction, cardiac-allograft vasculopathy and stroke. Exemplary cerebrovascular diseases include central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

EXEMPLIFICATION

| Table of abbreviations | |
|---|---|
| TFA | trifluoroacetic acid |
| THF | tetrahydrofuran |
| TEA | triethylamine |
| DMF | N,N-dimethylformamide |
| DCM | dichloromethane |
| AcOH/MeCO₂H | acetic acid |
| mCPBA | m-chloroperoxybenzoic acid |
| DMAP | 4-dimethylaminopyridine |
| dba | dibenzylideneacetone |
| BINAP | (±)-2,2'-Bis(diphenylphosphino)-1,1'-binaphthyl |

Example 1

Compounds of the present invention can be prepared using the procedures detailed in WO 2016/044463, published Mar. 24, 2016 ("the '463 application"), incorporated by reference in its entirety. For example, compounds of the present invention can be prepared racemically and the enantiomers separated.

Alternatively, compounds of the present invention, and in particular, the compounds set forth in Table 1, can be prepared using the procedures detailed in the '463 application. For example, compounds I-1 through I-8, I-11, I-15, I-32, I-33, and I-36 through I-51 can be prepared from intermediate S1-12, following the procedures described in the '463 application. Intermediate S1-12 can be prepared according to Scheme 1A or Scheme 1B, using procedures that are analogous to those described in the '463 application:

Scheme 1A

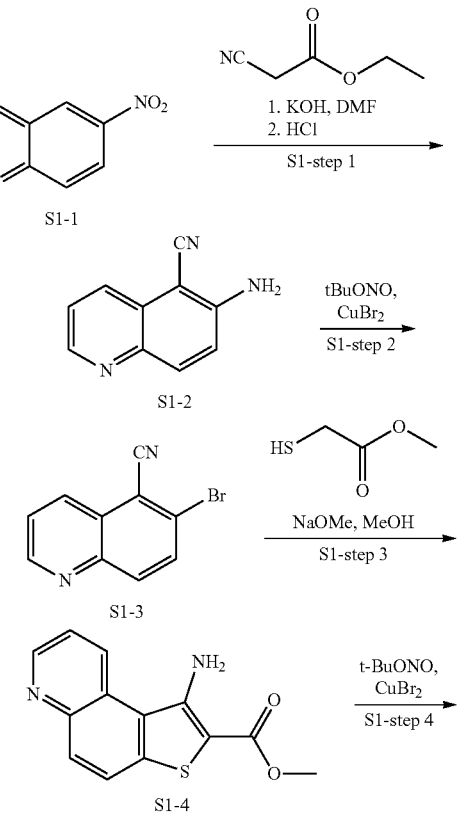

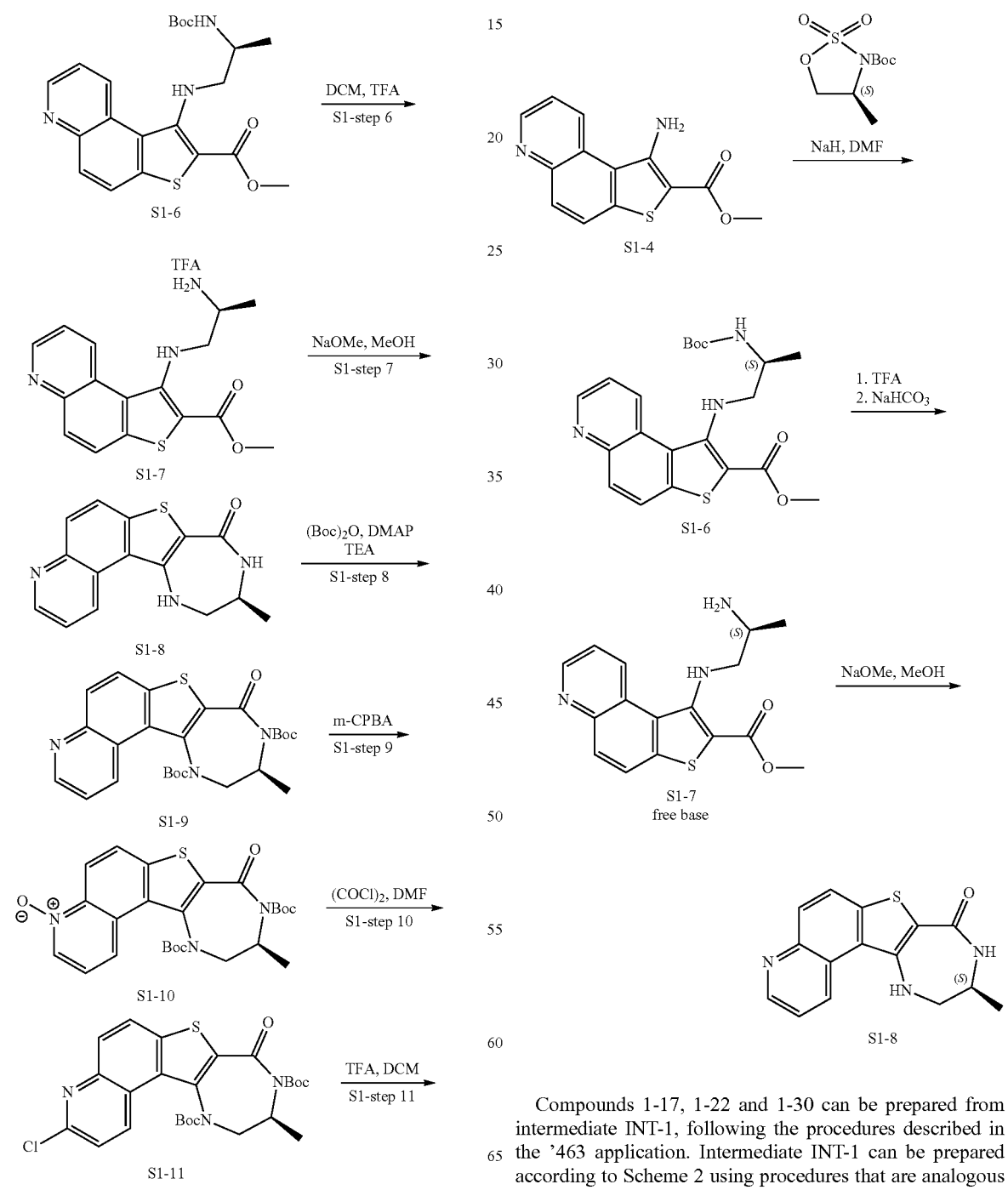
Compounds 1-17, 1-22 and 1-30 can be prepared from intermediate INT-1, following the procedures described in the '463 application. Intermediate INT-1 can be prepared according to Scheme 2 using procedures that are analogous to those described in the '463 application:

Scheme 2
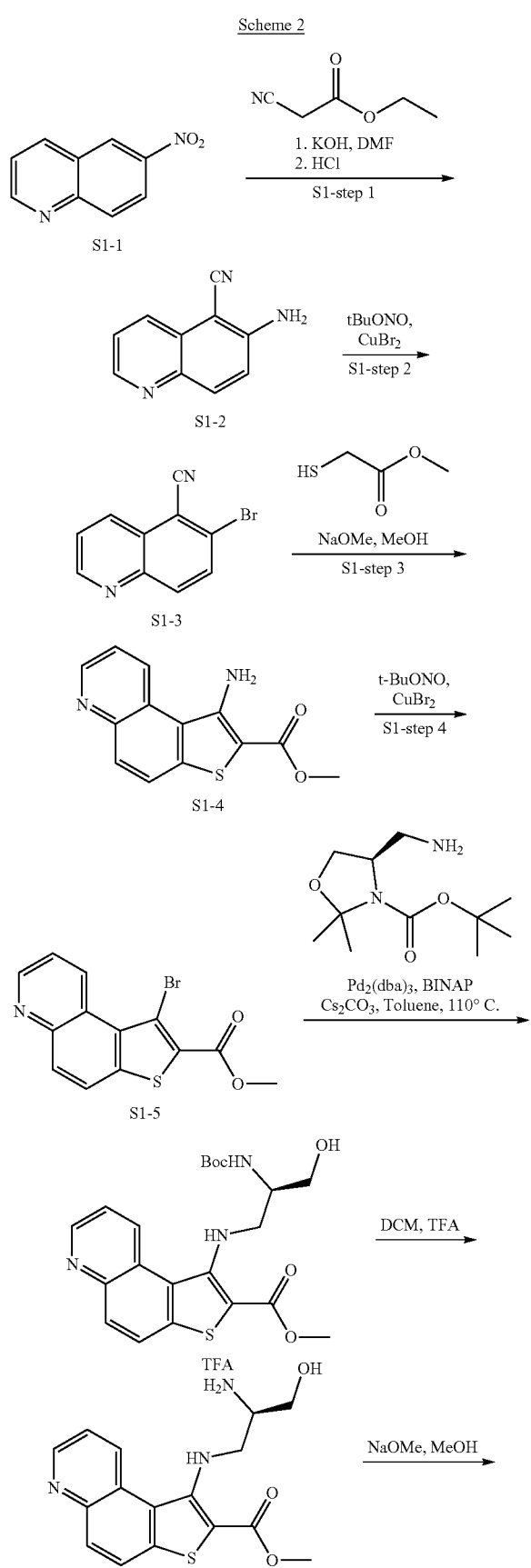
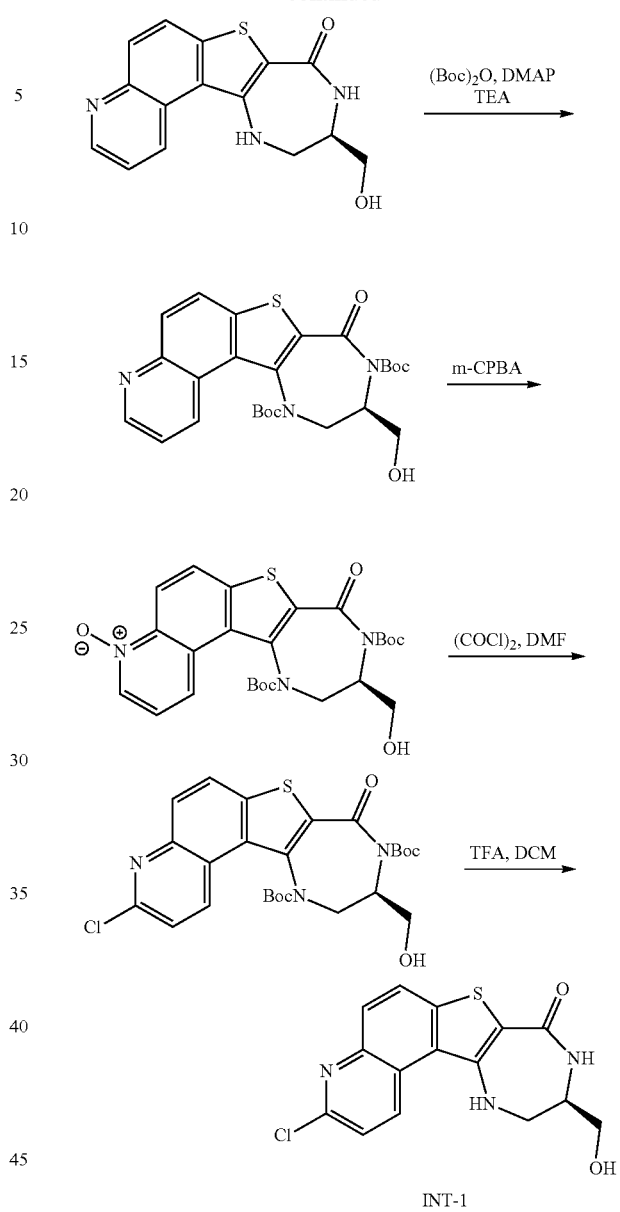
Compounds I-52, I-53, I-55 through I-58, I-62 through I-65, I-68, I-71, and I-75 through I-135 can be prepared from intermediate INT-6, following the procedures described in the '463 application. Intermediate INT-6 can be prepared according to Scheme 3 using procedures that are analogous to those described in the '463 application:
Scheme 3
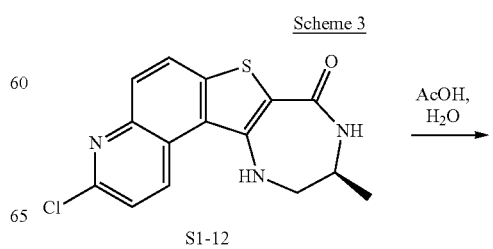

-continued

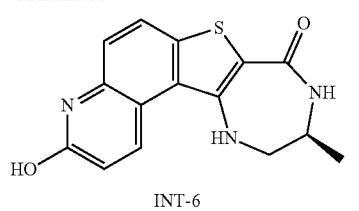

INT-6

Compounds I-9, I-10, I-12, I-13, I-23, I-34, I-59, I-60, I-61, I-66, I-67, I-69, I-70, I-73, and I-74 can be prepared from intermediate INT-5, following the procedures described in the '463 application. Intermediate INT-5 can be prepared according to Scheme 4 using procedures that are analogous to those described in the '463 application:

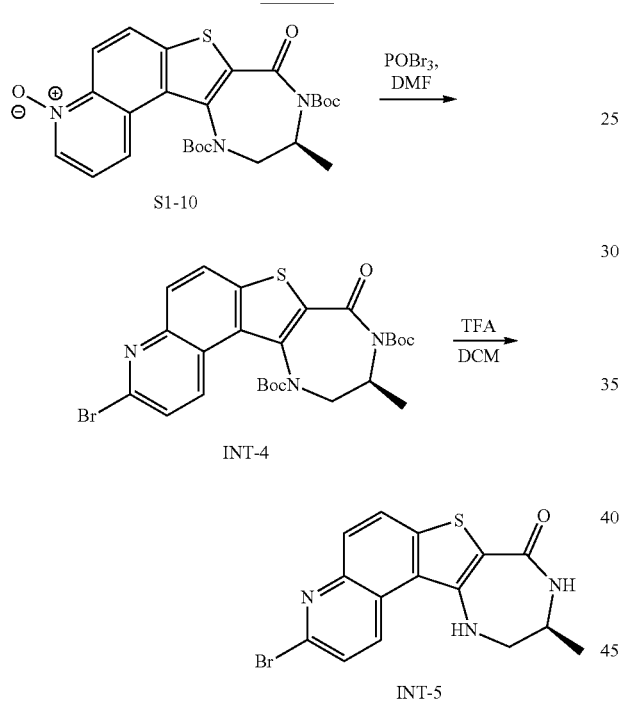

Compounds I-14, I-16, I-18 through I-21, I-24, I-25, I-27, and I-29 can be prepared from intermediate INT-3, following the procedures described in the '463 application. Intermediate INT-3 can be prepared according to Scheme 5 using procedures that are analogous to those described in the '463 application:

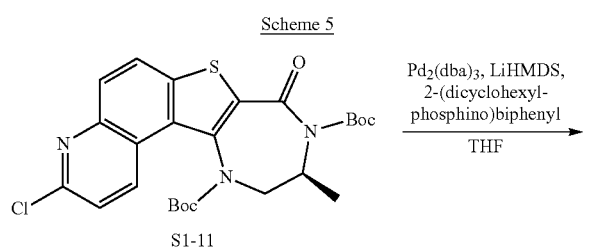

-continued

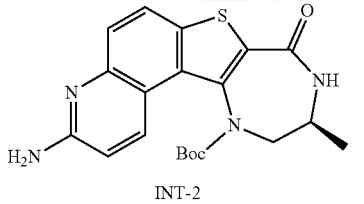

INT-2

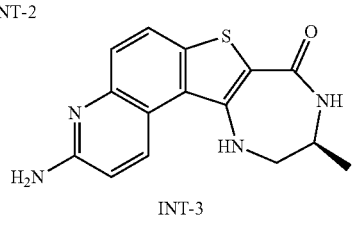

INT-3

Compound I-54 and I-72 can be prepared from intermediate INT-7, following the procedures described in the '463 application. Intermediate INT-7 can be prepared according to Scheme 6 using procedures that are analogous to those described in the '463 application:

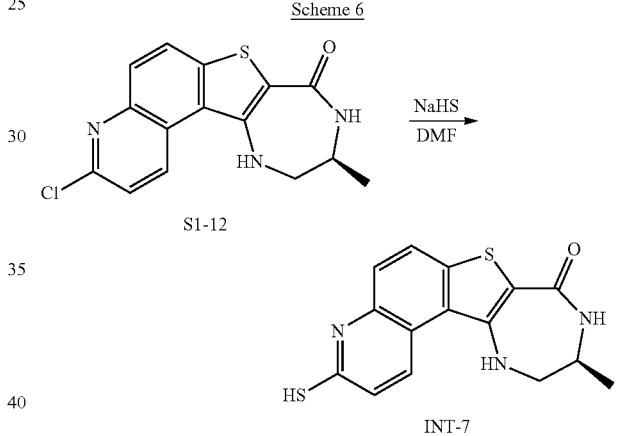

Compound I-26 can be prepared from intermediate S8-5, following the procedures described in the '463 application. Intermediate S8-5 can be prepared according to Scheme 7 using procedures that are analogous to those described in the '463 application:

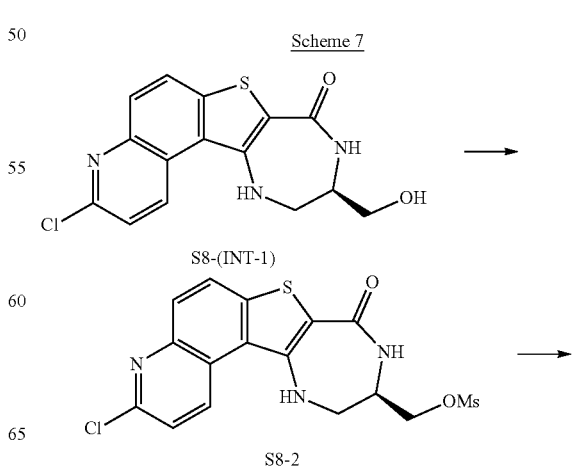

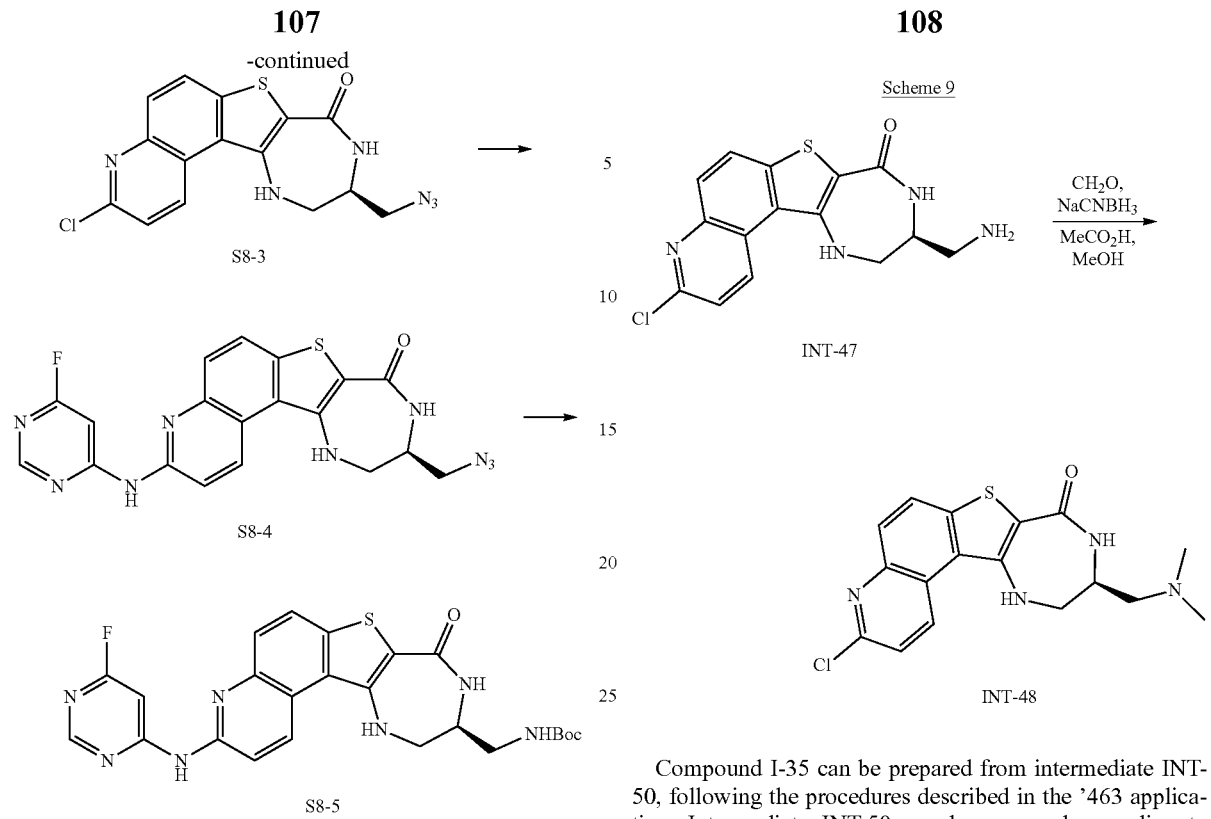

Compound I-28 can be prepared from intermediate INT-47, following the procedures described in the '463 application. Intermediate INT-47 can be prepared according to Scheme 8 using procedures that are analogous to those described in the '463 application:

Compound I-31 can be prepared from intermediate INT-48, following the procedures described in the '463 application. Intermediate INT-48 can be prepared according to Scheme 9 using procedures that are analogous to those described in the '463 application:

Compound I-35 can be prepared from intermediate INT-50, following the procedures described in the '463 application. Intermediate INT-50 can be prepared according to Scheme 10 using procedures that are analogous to those described in the '463 application:

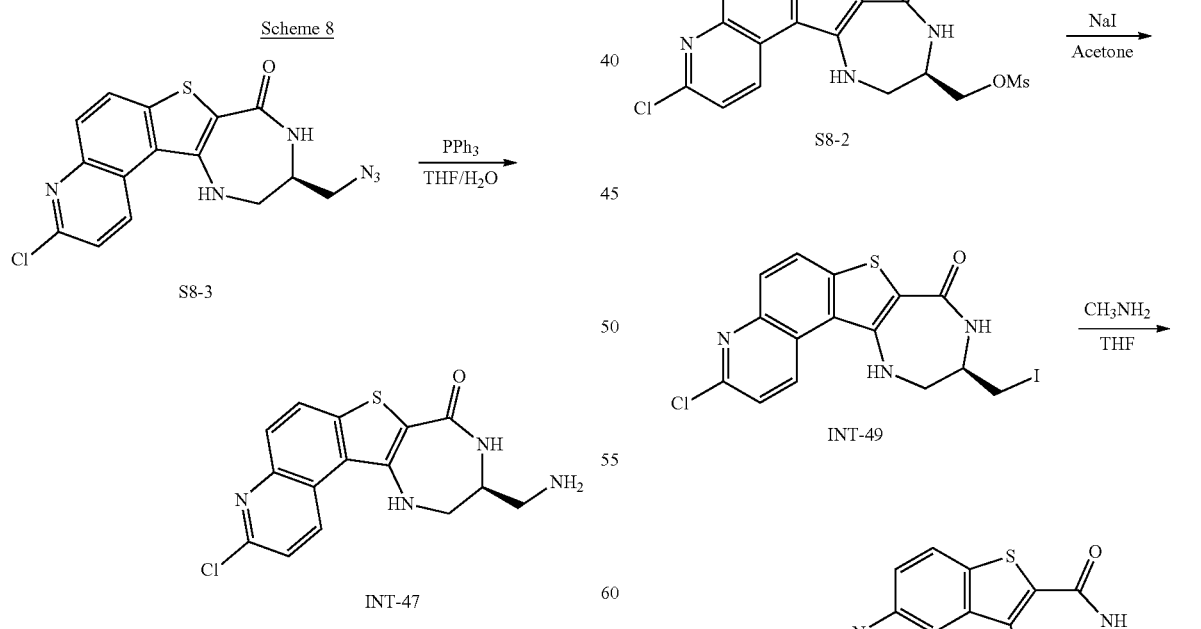

Example 2 (S)-3-((2-chloro-5-(ethoxymethyl)pyrimidin-4-yl)oxy)-10-methyl-9,10,11,12-tetrahydro-8H-[1,4]diazepino[5',6':4,5]thieno[3,2-f]quinolin-8-one

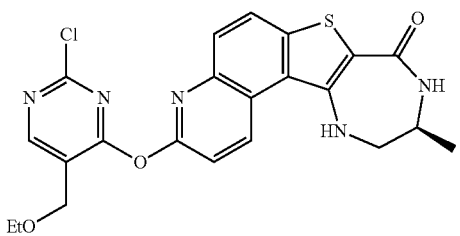 [SMILES: CCOCc1cnc(Cl)nc1Oc1ccc2c(ccc3sc4c(c32)NC[C@H](C)NC4=O)n1]

Step 1: Preparation of (S)-methyl 1-((2-aminopropyl)amino)-7-hydroxythieno[3,2-f]quinoline-2-carboxylate Benzenesulfonate

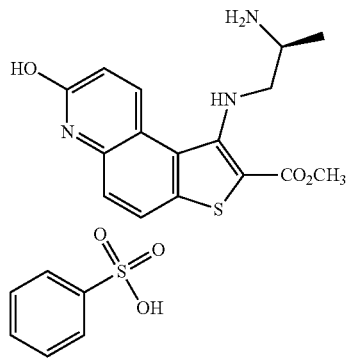

A hazy brown mixture of methyl 1-amino-7-(benzyloxy) thieno[3,2-f]quinoline-2-carboxylate (100 g, 274 mmol), (S)-tert-butyl 4-methyl-1,2,3-oxathiazolidine-3-carboxylate 2,2-dioxide (73.0 g, 302 mmol) in anhydrous NMP (400 ml, 4127 mmol) was stirred at ambient temperature for 30 minutes, followed by cooling the mixture to −15° C. to −20° C. Then a cloudy mixture of lithium tert-butoxide (27.4 g, 343 mmol) in anhydrous THF (135 ml) was charged over 90 min while keeping the reaction mixture less than −10° C. The reaction was kept at −10° C. for additional one hour and then quenched with acetic acid (19.6 ml, 343 mmol) over 10 minutes and then warmed to 20-25° C. over 30 minutes. The mixture was partitioned between 2-MeTHF (1000 ml) and 2.5% aqueous LiCl (500 ml). The aqueous phase is back extracted with 100 ml of 2-MeTHF. The organic phases were combined and washed two times with 5% aqueous LiCl (500 ml) and once with water (500 ml). The batch was heated to reflux and distilled at ~85° C. under atmospheric pressure until the batch volume was reduced to ~500 ml, followed by distillation at constant volume with addition of acetonitrile (1200 ml). Additional acetonitrile (200 ml) was added to bring the total batch volume to ~700 ml. The batch was cooled to 60-65° C. and a solution of benzenesulfonic acid (82 g, 494 mmol) in MeOH (200 ml) was added dropwise over 30 minutes. Additional MeOH (100 ml) was then added dropwise as a rinse and to bring the total batch volume to ~1000 ml. The reaction was held at 65-70° C. for at least 16 hours then cooled to 20-25° C. over 2 hours, held for 1h and then filtered. The yellow filter cake was then washed twice with (200 ml) 3:2 MeCN/MeOH. The final wet cake was then dried in a vacuum oven at 40° C. with a slow bleed of nitrogen for 12-16 hours to give a yellow solid (115.8 g, 86% yield); mp 283-285° C.; HPLC: Waters Ascentis Express C-18 HPLC column, 10 cm×4.6 m, 1 mL/min, 234 nm, gradient at 100% 0.1% $H_3PO_4$ to 100% $CH_3CN$ in 10 min, then hold at 100% $CH_3CN$ for 5 min): $t_R$=3.65 min (99.4%). $^1$H NMR (300 MHz, DMSO-$d_6$) δ ppm 1.25 (d, J=6.33 Hz, 3H) 3.02-3.19 (m, 1H) 3.22-3.44 (m, 2H) 3.90 (s, 3H) 6.25 (t, J=6.97 Hz, 1H) 6.71 (d, J=9.90 Hz, 1H) 7.25-7.40 (m, 3H) 7.51-7.66 (m, 3H) 7.85 (br s, 3H) 8.10 (d, J=8.80 Hz, 1H) 8.69 (d, J=9.90 Hz, 1H) 12.15 (s, 1H). $^{13}$C NMR (DMSO-$d_6$) δ 16.90, 47.28, 52.63, 52.85, 114.71, 114.95, 118.15, 122.45, 125.91, 126.29, 128.09, 128.58, 128.86, 134.24, 136.05, 138.54, 148.71, 151.46, 161.61, 164.53. LC/MS m/e=332. Anal. Calcd. for $C_{22}H_{23}N_3O_6S_2$: C, 53.98; H, 4.74; N, 8.58; S, 13.10. Found: C, 53.97; H, 4.92; N, 8.52; S, 12.96.

Step 2: Preparation of (S)-3-hydroxy-10-methyl-9,10,11,12-tetrahydro-8H-[1,4]diazepino[5',6':4,5]thieno[3,2-f]quinolin-8-one

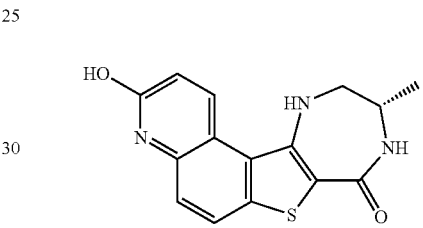

To a stirred yellow slurry of (S)-methyl 1-((2-aminopropyl)amino)-7-hydroxythieno[3,2-f]quinoline-2-carboxylate benzenesulfonate (110.3 g, 225 mmol) in methanol (2200 ml, 225 mmol) at ambient temperature under nitrogen was charged 2,3,4,6,7,8,9,10-octahydropyrimido[1,2-a]azepine ("DBU", 158 ml, 1127 mmol) slowly over 5 minutes with rapid agitation (300-400 rpm) while keeping temperature less than 35° C. The mixture was then heated to reflux (65-70° C.) for 24-36 hours until the benzenesulfonate was no more than 2% area by HPLC. If not met, heat for additional 18-24 hours. The batch was cooled to 20-30° C. over one hour and filtered. The cake was washed with MeOH (550 ml) and deliquored. The wet cake was transferred to a visually clean reactor and charged with MeCN (2200 ml), MeOH (550 ml) and 2,3,4,6,7,8,9,10-octahydropyrimido[1,2-a]azepine (33 ml). The mixture was heated to reflux (65-70° C.) for 18-24 hours until the benzenesulfonate was not more than 0.5% area by HPLC. The batch was cooled to 20-30° C. and filtered. The cake was washed with water (550 ml), MeOH:MeCN (1:1 v/v, 550 vol), deliquored and dried oven under vacuum at 45-55° C. for 18-24 hours to afford a yellow solid (62.6 g, 93% yield); HPLC: Waters Ascentis Express C-18 HPLC column, 10 cm×4.6 μm, 1 mL/min, 254 nm, gradient at 100% 0.1% $H_3PO_4$ to 100% $CH_3CN$ in 10 min, then hold at 100% $CH_3CN$ for 5 min): $t_R$=2.87 min (98.9%). $^1$H NMR (300 MHz, DMSO-$d_6$) δ ppm 1.16 (d, J=6.79 Hz, 3H) 3.33 (s, 3H) 3.38 (br d, J=4.68 Hz, 2H) 3.56 (br dd, J=6.60, 3.48 Hz, 1H) 6.60 (d, J=9.90 Hz, 1H) 6.86 (t, J=5.41 Hz, 1H) 7.43 (d, J=8.71 Hz, 1H) 7.93 (d, J=8.80 Hz, 1H) 8.08 (d, J=4.22 Hz, 1H) 8.80 (d, J=10.00 Hz, 1H) 12.05 (s, 1H); $^{13}$C NMR (DMSO-$d_6$) δ 19.11, 48.50, 52.39, 115.08, 116.57, 121.35, 125.90, 128.02, 134.45, 135.97, 138.41, 143.91, 161.42, 164.50. LC/MS m/e$^+$=300.

Anal. Calcd. for $C_{15}H_{13}N_3O_2S$: C, 60.19; H, 4.38; N, 14.04; S, 10.71. Found: C, 59.60; H, 4.07; N, 13.69; S, 10.38.

Step 3: Preparation of (S)-3-((2-chloro-5-(ethoxymethyl)pyrimidin-4-yl)oxy)-10-methyl-9,10,11,12-tetrahydro-8H-[1,4]diazepino[5',6':4,5]thieno[3,2-f]quinolin-8-one

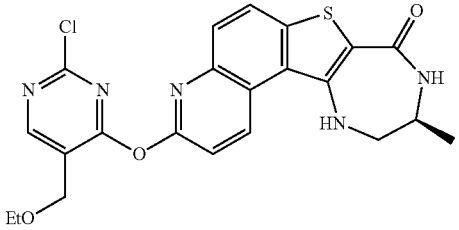 [SMILES: CCOCc1cnc(Cl)nc1Oc1ccc2c(ccc3sc4c(c32)NC[C@H](C)NC4=O)n1]

A yellow slurry mixture of (S)-3-hydroxy-10-methyl-9,10,11,12-tetrahydro-8H-[1,4]diazepino[5',6':4,5]thieno[3,2-f]quinolin-8-one (30 g, 100 mmol), 2,4-dichloro-5-(ethoxymethyl)pyrimidine (24.90 g, 120 mmol), and potassium carbonate (325 mesh) (16.96 g, 120 mmol) in DMSO (150 ml, 2114 mmol) and THF (150 ml, 1831 mmol) was stirred at ambient temperature for 5-10 minutes, followed by heating at 40-45° C. for at least 16 hours with sufficient agitation (350-400 rpm). The yellow/tan slurry mixture was then cooled to 20-25° C., and filtered over 9 g of Celite (prewetted with 15 mL of THF). The yellow filtrate (~400 ml) was transferred back to the visually clean jacketed flask along with 240 mL of THF, and was heated to 40-45° C. over 30 minutes. To the mixture was charged 150 mL of 10 wt % aqueous NaCl, stirred for 5 minutes and settled for phase split. After the bottom aqueous phase was removed, 150 mL of THF and 150 mL of 10 wt % aqueous NaCl were charged and stirred at 40-45° C. for 5 minutes. The aqueous phase was removed again. Then, 90 mL of THF and 50 mL of 10 wt % aqueous NaCl were charged, maintaining the batch temp at 40-45° C. (lower temp will make product crystallize out). The aqueous phase was removed and the remaining organic portion was distilled under atmospheric pressure at 65-70° C. to ~300 ml. The batch was seeded with 200 mg of the product and the resulting mixture was aged for one hour. Then the batch was distilled with addition of isopropanol (600 ml) at a rate sufficient to maintain a constant batch volume. The slurry was cooled from ~70° C. to 22° C. over 4 hours, hold at 22° C. for 16 hours and filtered, washed with 3×30 mL of IPA, and dried in a vacuum oven at 40-45° C. for 12-16 hours to afford a yellow solid (41.1 g, 87% yield); HPLC: Waters Ascentis Express C-18 HPLC column, 10 cm×4.6 m, 1 mL/min, 234 nm, gradient at 100% 0.1% $H_3PO_4$ to 100% $CH_3CN$ in 10 min, then hold at 100% $CH_3CN$ for 5 min): $t_R$=6.40 min (99.0%). $^1$H NMR (300 MHz, DMSO-$d_6$) δ ppm 1.13-1.27 (m, 6H) 3.42-3.54 (m, 2H) 3.57-3.70 (m, 3H) 4.66 (s, 2H) 7.18 (br t, J=5.18 Hz, 1H) 7.64 (d, J=9.08 Hz, 1H) 7.87 (d, J=8.89 Hz, 1H) 8.12-8.23 (m, 2H) 8.72 (s, 1H) 9.37 (d, J=9.17 Hz, 1H); $^{13}$C NMR (75 MHz, DMSO-$d_6$) δ ppm 15.47, 19.12, 48.46, 52.39, 64.02, 66.28, 114.87, 115.10, 119.60, 124.30, 126.49, 126.75, 127.7, 135.77, 139.30, 145.00, 145.84, 156.32, 158.02, 160.48, 164.52, 167.37. LC/MS m/e+=470. Anal. Calcd. for $C_{22}H_{20}N_5O_3SCl$: C, 56.23; H, 4.29; N, 14.90; S, 6.82; Cl, 7.54. Found: C, 55.87; H, 4.33; N, 14.61; S, 6.60.

Biological Examples

Described below are in vitro assays used to measure the biological activity of provided compounds as selective inhibitors of MK2.

Example 3

Mitogen-Activated Protein Kinase-Activated Protein Kinase 2 Omnia® Assay for Compound Potency Assessment:

The protocol below describes a continuous-read kinase assay optimized to measure potency of compounds against p38a activated, mitogen-activated protein kinase-activated protein kinase 2 (MAPKAP-K2 or MK2) enzyme. Further details of this assay are described by Life Technologies, Carlsbad, Calif. on their website at the following URL: http://tools.lifetechnologies.com/content/sfs/manuals/omnia_kinase_assayman.pdf.

[Reagent] used:
[MK-2]=0.4 nM,
[ATP]=10 M and
[ST3-Sox]=10 LM (ATP $a^{PP}$KM=10 μM)

Briefly, 10× stock solutions of MK2 (PV3317, from Life Technologies), 1.13×ATP (AS001A), and Sox conjugated peptide substrate, S/T3-Sox, (KZN1031) were prepared in 1× kinase reaction buffer consisting of 20 mM Tris, pH 7.5, 5 mM $MgCl_2$, 1 mM EGTA, 5 mM 3-glycerophosphate, 5% glycerol (10× stock, KB001A) and 0.2 mM DTT (DS001A). Enzyme solution (5 μL) was added to each of DMSO (5 μL) or serially diluted test compounds prepared in DMSO in a Corning (#3574) 384-well, white, non-binding surface microtiter plate (Corning, N.Y.). Kinase reactions were started with the addition of 45 μL of the ATP-peptide substrate S/T3-Sox mix and monitored every 71 seconds for 120 minutes at $\lambda_{ex}$360/$\lambda_{em}$485 in a Synergy H4 plate reader from BioTek (Winooski, Vt.) at room temperature.

Background signals from the no enzyme control wells were subtracted from all progress curves. The initial linear portions of the net progress curves were fit according to a linear equation to yield the slope and percentage of inhibition (% inhibition) at each compound concentration. The net progress curves obtained during the first two hours of reactions were also fit according to an ascending single-exponential equation (Eq. 1) to yield $k_{obs}$ values at each compound concentration. Plots of % Inhibition versus inhibitor concentrations were fit according to a dose-response equation (Eq. 2) to generate $IC_{50}$ and Hill slope values while plots of $k_{obs}$ versus inhibitor concentration were fit according to Equation 3 (Eq. 3) to generate apparent $k_{inact}/K_I$ values using the GraphPad PRISM software (Version 6.00; GraphPad San Diego, Calif.).

$$F = V_0 \frac{(1 - e^{-k_{obs}t})}{k_{obs}} \quad \text{(Eq. 1)}$$

where F is the fluorescence intensity from the plate reader, $V_0$ is a constant reflecting the relationship between the instrument readout and product concentration, t is time, e is Euler's number, and $k_{obs}$ is the observed inactivation rate constant.

$$\% \text{ Inhibition} = \frac{100}{1 + \left(\frac{IC_{50}}{[I]}\right)^n} \quad \text{(Eq. 2)}$$

where % inhibition is percentage of inhibition, $IC_{50}$ is half maximal inhibitory concentration, [I] is the inhibitor concentration, and n is the Hill slope.

$$k_{obs} = \frac{k_{inact}}{K_I} \frac{[I]}{2} \quad \text{(Eq. 3)}$$

where $k_{obs}$ is the observed inactivation rate constant, $k_{inact}$ is the apparent inactivation rate constant, $K_I$ is the apparent inhibition constant, and [I] is the inhibitor concentration. Results from this assay, showing $IC_{50}$ (i.e. the concentration at which a test compound inhibits substrate peptide phosphorylation 50%) are reported in nanomolar. Potency results for the compounds tested are shown in Table A in the column entitled "MK2 $IC_{50}$."

Example 4

Mass Spectrometry Assay for Detecting Level of Covalent Modification of MK2

Compound I-82 was assayed in a mass spectrometric assay to measure their ability to covalently modify MK2 protein. The procedure for this assay follows. Intact MK2 protein (Invitrogen, Cat. No. PR5320A) was incubated for 60 minutes at room temperature with a 10-fold excess of test compound to protein. Aliquots of the resulting mixture (6 µL each) were diluted with 0.2% trifluoroacetic acid (TFA, 10 µL) prior to micro C4 ZipTipping directly onto the MALDI target using sinapinic acid as the desorption matrix (10 mg/ml in 0.1% TFA:acetonitrile 50:50, v/v). The centroid mass of the target protein in the control sample was compared with the centroid mass of the target protein incubated with compound. A shift in the centroid mass of the treated protein compared to the untreated protein was divided by the molecular weight of the compound. This number corresponds to the percentage of modified protein (a measure of the proportion of total target protein covalently bound to the test compound) after one hour incubation. Results from this assay are reported in Table A under the column "Mass Modification".

Compound I-82 was assayed in a magnetic bead mass spectrometric assay to measure their ability to covalently modify MK2 protein. The procedure for this assay follows. MK2 protein (Invitrogen, Cat. No. PR5320A) was incubated for 60 minutes at room temperature with a 10-fold excess of test compound to protein. 3 µL of magnetic Ni-NTA beads were added to the 6 µL aliquots of sample, washed, eluted with 0.2% trifluoroacetic acid (TFA, 2 µL), and spotted directly onto the MALDI target using sinapinic acid as the desorption matrix (10 mg/ml in 0.1% TFA:acetonitrile 50:50, v/v). The centroid mass of the target protein in the control sample was compared with the centroid mass of the target protein incubated with compound. A shift in the centroid mass of the treated protein compared to the untreated protein was divided by the molecular weight of the compound. This number corresponds to the percentage of modified protein (a measure of the proportion of total target protein covalently bound to the test compound) after one hour incubation. Results from this assay are reported in Table A under the column "Mass Modification".

Example 5

MK2 Cellular Assay—Detection of Total and Phospho-Hsp27 (Serine 78) by MSD ELISA (Thp1)

Compounds of the invention can be assayed in Thp-1 human acute monocytic leukemia cells to measure inhibition of MK2 activity according to procedures detailed in the '463 application.

Specifically, Thp-1 cells were grown in culture medium containing RPMI/10% FBS (fetal bovine serum)/0.05 mM 2-mercaptoethanol. 72 hours prior to the assay, $8 \times 10^4$ cells per well were plated in a 96 well flat bottom plate along with 10 ng/mL phorbol 12-myristate 13-acetate (PMA). Cells were cultured in an incubator at 37° C. until needed for the assay. Cell plate media was replaced with culture media just prior to assay while compound dilutions were being made.

Stock solutions of test compound, 1 mM in DMSO, were prepared. 0.9 µl of test compound was added to 300 µl cell media for a starting concentration of 3000 nM. Three-fold serial dilutions (1:3) were made in cell assay media until the final concentration of 0.15 nM. Cell plate media was discarded, followed by addition of 100 µl of the compound containing media. The resulting preparation was incubated at 37° C. for 1 hour.

Test compound-containing cell assay media was removed and the cells were washed once with cell assay media. Cell assay media containing 50 ng/mL LPS (lipopolysaccharide) was added to the each well and incubated for 45 minutes. Following LPS incubation, the cells were washed once with PBS (phosphate-buffered saline) and lysed with 60 µl Cell Extraction Buffer (Invitrogen #FNN0011) plus protease and phosphatase inhibitors. The plate was then stored at −80° C. until further analysis.

The MULTI-SPOT Phospho(Ser78)/Total HSP27 ELISA Assay kit was purchased from Meso Scale Delivery (MSD; catalog #K15128D). MSD provides a plate that has been pre-coated with capture antibodies for phosphor-HSP27 (Ser78) and total HSP27. The pre-coated MSD plate was blocked with 150 µL/well of 3% BSA in MSD wash buffer. The preparation was placed on a shaker at room temperature for an hour. While the ELISA plate was blocked, the cell assay plate stored at −80° C. was placed on a shaker at 4° C. for 1 hour to thaw. The blocked MSD plate was washed on a plate washer, tapping out the last bit of wash solution, followed by addition of 30 µl of the lysate from the cell assay plate. The preparation was covered and incubated for 1 hour at room temperature. The lysate was removed, the plate was washed 3 times on a plate washer and the last bit of wash buffer was tapped out and replaced with 25 µl/well detection antibody (anti-total HSP27 conjugated with an electrochemiluminescent compound, MSD SULFO-TAG label, supplied in kit) made in 1% BSA/MSD wash buffer. The plate was incubated for 1 hour at room temperature on a shaker, followed by 3 washes. The last bit of wash buffer was tapped out. 150 µl/well 1×MSD read buffer was added (4× read buffer supplied with kit) and the plate was analyzed on the MSD SECTOR®Imager for analysis. The SECTOR®Imager measures intensity of emitted light to provide a quantitative measure of phosphorylated HSP27 (Ser78) and total HSP27 present in the sample. The relative percent phosphoprotein in a sample is calculated by dividing the Phospho-HSP27 signal intensity over the total HSP27 signal intensity measured in each well. A curve fitting analysis was performed using Graph Pad Prism software to generate an $EC_{50}$ based on the inhibitory responses of the LPS-induced p-HSP27/total HSP27 signal ratio's normalized to DMSO-treated controls (set at 100% signal intensity). Results from this assay, showing $EC_{50}$ (i.e. the concentration at which a test compound inhibits phosphorylation of Hsp27 by 50%) are reported in nanomolar. Results from this assay are reported in Table A under the column "pHSP27 signaling $EC_{50}$."

Table A shows data for selected compounds in various assays. Compounds having an activity designated as "A" provided an $EC_{50}/IC_{50} \leq 100$ nM; compounds having an activity designated as "B" provided an $EC_{50}/IC_{50}$ of 101-500 nM; compounds having an activity designated as "C" provided an $EC_{50}/IC_{50}$ of 501-999 nM; compounds having an activity designated as "D" provided an $EC_{50}/IC_{50}$ of $\geq 1000$ nM. Compounds having an activity designated as "E" provided a mass modification of $\geq 70\%$; compounds having an activity designated as "F" provided a mass modification of 31-69%; compounds having an activity designated as "G" provided a mass modification $\leq 30\%$.

TABLE A

| Number | MK2 $IC_{50}$ | Mass Modification | pHSP27 signaling $EC_{50}$ |
| --- | --- | --- | --- |
| I-82 | D | F | B |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

Enumerated Embodiments

1. A compound of formula I:

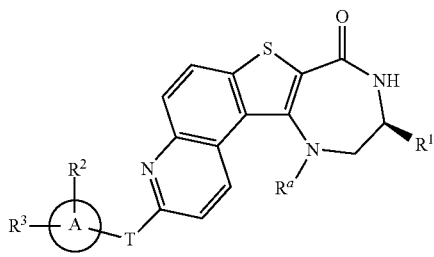

I or a pharmaceutically acceptable salt thereof, wherein:
Ring A is phenyl or a 5-6 membered monocyclic heteroaryl ring having 1-3 nitrogens, or a 8-14 membered bridged or fused bicyclic heteroaromatic ring having 1-4 heteroatoms independently selected from nitrogen, oxygen, and sulfur;
T is a bivalent moiety selected from by —N(R)—, —O—, —S—, —S(O)—, —SO$_2$—, —C(S)—, —Si(R$^4$)$_2$—, —P(R$^5$)—, —P(O)$_2$—, or a bivalent saturated straight or branched 1-3 membered hydrocarbon chain, wherein the hydrocarbon chain is optionally substituted with oxo or —OR;
each R is independently hydrogen or an optionally substituted C$_{1-6}$ aliphatic, or:
two R groups on the same nitrogen are taken together with the nitrogen to form a 3-7 membered saturated or partially unsaturated heterocyclic ring having 1-3 heteroatoms selected from nitrogen, oxygen, or sulfur;
R$^a$ is hydrogen or an optionally substituted C$_{1-6}$ aliphatic;
R$^1$ is R or —(CH$_2$)$_p$R$^x$;
p is 0, 1, 2, or 3;
R$^x$ is —CN, —NO$_2$, halogen, —OR, —SR, —N(R)$_2$, —C(O)N(R)$_2$, —C(O)OR, —C(O)R, —N(R)C(O)R, —SO$_2$N(R)$_2$, or —N(R)SO$_2$;
R$^2$ is halogen, —CN, —SR$^y$, —S(O)R$^y$, —SO$_2$R$^y$, —OSO$_2$R$^y$, —OC(O)R$^y$, or —OP(O)$_2$OR$^y$;
each R$^y$ is independently selected from optionally substituted C$_{1-6}$ aliphatic or optionally substituted phenyl;
R$^3$ is hydrogen, optionally substituted C$_{1-6}$ aliphatic, —CN, —NO$_2$, halogen, —OR, —N(R)$_2$, —C(O)N(R)$_2$, —C(O)OR, -Cy, —C(O)N(R)-Cy, —C(O)—Cy, —O-Cy, —O—(CH$_2$)$_n$-Cy, —(CH$_2$)$_n$—O-Cy, —(CH$_2$)$_m$N(R)$_2$, —(CH$_2$)$_m$OR, —N(R)—Cy, —N(R)—(CH$_2$)$_n$-Cy, —(CH$_2$)$_n$—N(R)-Cy, or —(CH$_2$)$_m$-Cy;
each R$^4$ is independently hydrogen, —OR, C$_{1-6}$ aliphatic, phenyl, a or 5-6 membered heteroaryl ring having 1-3 heteroatoms independently selected from nitrogen, oxygen, and sulfur;
each R$^5$ is independently —OR, C$_{1-6}$ aliphatic, phenyl, or a 5-6 membered heteroaryl ring having 1-3 heteroatoms independently selected from nitrogen, oxygen, and sulfur;
each of m and n is independently 0-4; and
each Cy is independently an optionally substituted ring selected from a 3-9 membered saturated or partially unsaturated monocyclic carbocyclic ring, a 3-9 membered saturated or partially unsaturated monocyclic heterocyclic ring having 1-3 heteroatoms independently selected from nitrogen, oxygen, and sulfur, phenyl, a 5-6 membered heteroaryl ring having 1-3 heteroatoms independently selected from nitrogen, oxygen, and sulfur, a 7-12 membered saturated or partially unsaturated fused or bridged bicyclic carbocyclic ring, or a 6-12 membered saturated or partially unsaturated fused or bridged bicyclic heterocyclic ring having 1-3 heteroatoms independently selected from nitrogen, oxygen, and sulfur.

2. The compound according to embodiment 1, wherein T is —N(R)—, —O—, or —S—.

3. The compound according to embodiment 2, wherein T is —NH— or —O—.

4. The compound according to embodiment 3, wherein T is —NH—.

5. The compound according to embodiment 1, wherein R$^1$ is R, —CH$_2$OR, or —CH$_2$N(R)$_2$.

6. The compound according to embodiment 1, wherein R$^1$ is methyl, —CH$_2$OCH$_3$, or —CH$_2$NH$_2$.

7. The compound according to embodiment 6, wherein R$^1$ is methyl.

8. The compound according to embodiment 1, wherein Ring A is phenyl and R$^3$ is selected from —CN, —NO$_2$, halogen, —C(O)N(R)$_2$, —C(O)OR, -Cy, —C(O)N(R)-Cy, or —C(O)—Cy.

9. The compound according to embodiment 8, wherein Ring A is phenyl and R$^3$ is selected from —CN, —NO$_2$, or halogen.

10. The compound according to embodiment 9, wherein Ring A is phenyl and R$^3$ is selected from —CN or halogen.

11. The compound according to embodiment 1, wherein Ring A is a 6-membered heteroaryl ring having 1-3 nitrogens.

12. The compound according to embodiment 11, wherein Ring A is pyridyl, pyrimidinyl, pyridazinyl, or triazinyl.

13. The compound according to embodiment 12, wherein said compound is any one of formula II, III, IV, V, or VI:

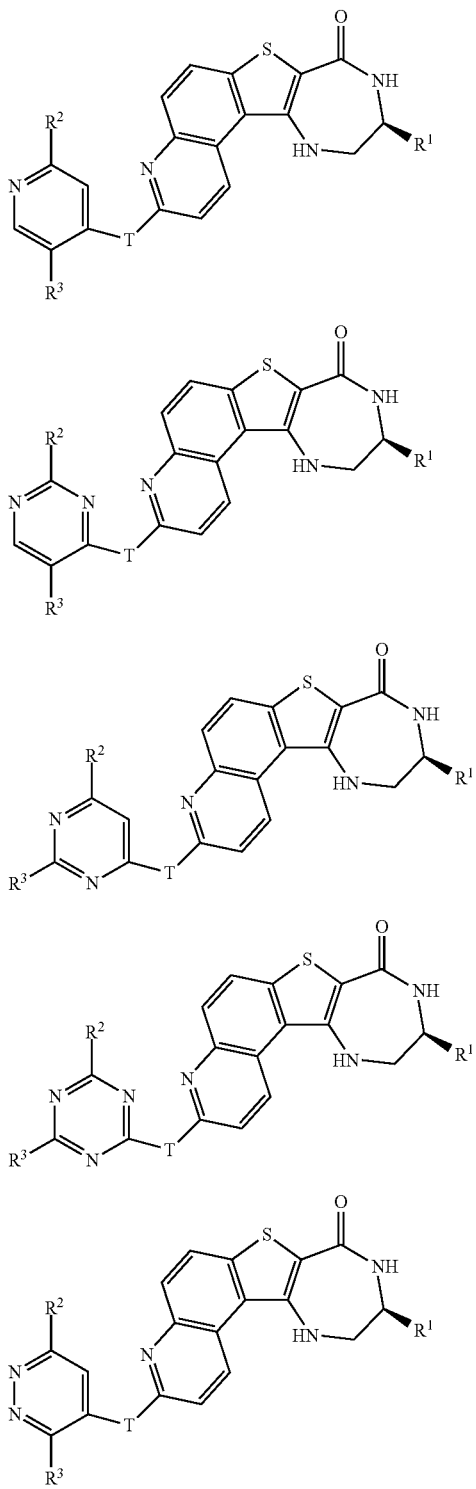

or a pharmaceutically acceptable salt thereof.

14. The compound according to embodiment 1, wherein $R^2$ is halogen.

15. The compound according to embodiment 14, wherein $R^2$ is fluoro or chloro.

16. The compound according to embodiment 1, wherein $R^2$ is —SR or —SO$_2$R.

17. The compound according to embodiment 14, wherein $R^2$ is —SCH$_3$ or —SO$_2$CH$_3$.

18. The compound according to embodiment 11, wherein $R^3$ is R, wherein R is hydrogen.

19. The compound according to embodiment 11, wherein $R^3$ is R, wherein R is optionally substituted C$_{1-6}$ aliphatic.

20. The compound according to embodiment 19, wherein $R^3$ is selected from —CH$_2$OH, —CH$_2$OCH$_3$ and —CH$_3$.

21. The compound according to embodiment 11, wherein $R^3$ is —OR, —(CH$_2$)$_m$N(R)$_2$, or —(CH$_2$)$_m$OR.

22. The compound according to embodiment 21, wherein $R^3$ is selected from —OCH$_2$OCH$_2$CH$_3$, —O(CH$_2$)$_2$OCH$_3$, —O(CH$_2$)$_2$N(CH$_3$)$_2$, and —OCH$_3$.

23. The compound according to embodiment 1, wherein $R^3$ is halogen, —CN, NO$_2$, —C(O)N(R)$_2$, or —C(O)OR.

24. The compound according to embodiment 23, wherein $R^3$ is halogen, —CN, or NO$_2$.

25. The compound according to embodiment 23, wherein, $R^3$ is —C(O)N(R)$_2$, or —C(O)OR.

26. The compound according to embodiment 25, wherein $R^3$ is selected from —C(O)NH$_2$, —C(O)OCH$_2$CH$_3$, and —OC(O)CH$_3$.

27. The compound according to embodiment 11, wherein $R^3$ is -Cy, —(CH$_2$)$_m$-Cy, —C(O)N(R)-Cy, —C(O)—Cy, —OR, —O-Cy, —N(R)—Cy, —N(R)—(CH$_2$)$_n$-Cy, —(CH$_2$)$_n$—N(R)-Cy, or —O—(CH$_2$)$_n$-Cy.

28. The compound according to embodiment 27, wherein each -Cy is independently an optionally substituted ring selected from a 3-7 membered saturated or partially unsaturated carbocyclic ring.

29. The compound according to embodiment 27, wherein each -Cy is independently an optionally substituted ring selected from a 4-7 membered saturated or partially unsaturated heterocyclic ring having 1-3 heteroatoms independently selected from nitrogen, oxygen, and sulfur.

30. The compound according to embodiment 29, wherein each -Cy is independently an optionally substituted ring selected from oxetanyl, piperidinyl, pyrrolidinyl, tetrahydrofuranyl, piperazinyl, and morpholinyl.

31. A pharmaceutically acceptable composition comprising the compound according to embodiment 1 and a pharmaceutically acceptable carrier, adjuvant, or vehicle.

32. A method for inhibiting MK2 kinase, or a mutant thereof, activity in a biological sample comprising the step of contacting said biological sample with a compound according to embodiment 1.

33. A method for inhibiting MK2 kinase, or a mutant thereof, activity in a patient comprising the step of administering to said patient the composition according to embodiment 31.

34. The method according to embodiment 33, wherein the MK2 kinase, or a mutant thereof, activity is inhibited irreversibly.

35. The method according to embodiment 34, wherein the MK2 kinase, or a mutant thereof, activity is inhibited irreversibly by covalently modifying Cys140 of MK2.

36. A method for treating an MK2-mediated disease or disorder in a patient in need thereof, comprising the step of administering to said patient the composition according to embodiment 31.

37. The method according to embodiment 36, wherein the MK2-mediated disease or disorder is an autoimmune disorder, chronic or acute inflammatory disorder, an auto-inflammatory disorder, a fibrotic disorder, a metabolic disorder, a neoplasia, or a cardiovascular or cerebrovascular disorder.

38. The method according to embodiment 37, wherein the MK2-mediated disease or disorder is an autoimmune disorder, chronic or acute inflammatory disorder, or an auto-inflammatory disorder.

39. The method according to embodiment 38, wherein the autoimmune disorder, chronic or acute inflammatory disorder, and/or auto-inflammatory disorder is selected from the group consisting of inflammatory bowel diseases, ulcerative colitis, Crohn's disease, multiple sclerosis, psoriasis, arthritis, rheumatoid arthritis, osteoarthritis, juvenile arthritis, psoriatic arthritis, reactive arthritis, ankylosing spondylitis, cryopyrin associated periodic syndromes, Muckle-Wells syndrome, familial cold auto-inflammatory syndrome, neonatal-onset multisystem inflammatory disease, TNF receptor associated periodic synderome, acute and chronic pancreatitis, atherosclerosis, gout, ankylosing spondylitis, fibrotic disorders, hepatic fibrosis, idiopathic pulmonary fibrosis, nephropathy, sarcoidosis, scleroderma, anaphylaxis, diabetes, diabetes mellitus type 1, diabetes mellitus type 2, diabetic retinopathy, Still's disease, vasculitis, sarcoidosis, pulmonary inflammation, acute respiratory distress syndrome, wet and dry age-related macular degeneration, autoimmune hemolytic syndromes, autoimmune and inflammatory hepatitis, autoimmune neuropathy, autoimmune ovarian failure, autoimmune orchitis, autoimmune thrombocytopenia, silicone implant associated autoimmune disease, Sjogren's syndrome, familial Mediterranean fever, systemic lupus erythematosus, vasculitis syndromes, temporal, Takayasu's and giant cell arteritis, Behcet's disease, Wegener's granulomatosis, vitiligo, secondary hematologic manifestation of autoimmune diseases, anemias, drug-induced autoimmunity, Hashimoto's thyroiditis, hypophysitis, idiopathic thrombocytic pupura, metal-induced autoimmunity, myasthenia gravis, pemphigus, autoimmune deafness, Meniere's disease, Goodpasture's syndrome, Graves' disease, HW-related autoimmune syndromes, Gullain-Barre disease, Addison's disease, anti-phospholipid syndrome, asthma, atopic dermatitis, Celiac disease, Cushing's syndrome, dermatomyositis, idiopathic adrenal adrenal atrophy, idiopathic thrombocytopenia, Kawasaki syndrome, Lambert-Eaton Syndrome, pernicious anemia, pollinosis, polyarteritis *nodosa*, primary biliary cirrhosis, primary sclerosing cholangitis, Raynaud's, Reiter's Syndrome, relapsing polychondritis, Schmidt's syndrome, thyrotoxidosis, sepsis, septic shock, endotoxic shock, exotoxin-induced toxic shock, gram negative sepsis, toxic shock syndrome, glomerulonephritis, peritonitis, interstitial cystitis, hyperoxia-induced inflammations, chronic obstructive pulmonary disease (COPD), vasculitis, graft vs. host reaction, graft vs. host disease, allograft rejections, acute allograft rejection, chronic allograft rejection, early transplantation rejection, acute allograft rejection, reperfusion injury, pain, acute pain, chronic pain, neuropathic pain, fibromyalgia, chronic infections, meningitis, encephalitis, myocarditis, gingivitis, post surgical trauma, tissue injury, traumatic brain injury, enterocolitis, sinusitis, uveitis, ocular inflammation, optic neuritis, gastric ulcers, esophagitis, peritonitis, periodontitis, dermatomyositis, gastritis, myositis, polymyalgia, pneumonia and bronchitis.

40. The method according to embodiment 37, wherein the MK2-mediated disease or disorder is a fibrotic disorder.

41. The method according to embodiment 40, wherein the fibrotic disorder is selected from the group consisting of systemic sclerosis/scleroderma, lupus nephritis, connective tissue disease, wound healing, surgical scarring, spinal cord injury, CNS scarring, acute lung injury, pulmonary fibrosis, idiopathic pulmonary fibrosis, cystic fibrosis, chronic obstructive pulmonary disease, adult respiratory distress syndrome, acute lung injury, drug-induced lung injury, glomerulonephritis, chronic kidney disease, diabetic nephropathy, hypertension-induced nephropathy, alimentary track or gastrointestinal fibrosis, renal fibrosis, hepatic or biliary fibrosis, liver fibrosis, nonalcoholic steatohepatitis, hepatitis C, hepatocellular carcinoma, cirrhosis, primary biliary cirrhosis, cirrhosis due to fatty liver disease cirrhosis due to alcoholic fatty liver disease, cirrhosis due to nonalcoholic steatosis/non-alcoholic fatty liver disease, radiation-induced fibrosis head and neck fibrosis, gastrointestinal fibrosis, pulmonary fibrosis, primary sclerosing cholangitis, restenosis, cardiac fibrosis, endomyocardial fibrosis, atrial fibrosis, opthalmic scarring, fibrosclerosis, fibrotic cancers, fibroids, fibroma, fibroadenomas, fibrosarcomas, transplant arteriopathy, keloid, mediastinal fibrosis, myelofibrosis, retroperitoneal fibrosis, progressive massive fibrosis, and nephrogenic systemic fibrosis.

42. The method according to embodiment 37, wherein the MK2-mediated disease or disorder is a metabolic disorder.

43. The method according to embodiment 42, wherein the metabolic disorder is selected from the group consisting of obesity, steroid-resistance, glucose intolerance, and metabolic syndrome.

44. The method according to embodiment 37, wherein the MK2-mediated disease or disorder is a neoplasia.

45. The method according to embodiment 44, wherein the neoplasia is selected from the group consisting of angiogenesis disorders, multiple myeloma, leukemias, acute lymphocytic leukemia, acute and chronic myelogenous leukemia, chronic lymphocytic leukemia, acute lymphoblastic leukemia, promyelocytic leukemia, lymphomas, B-cell lymphoma, T-cell lymphoma, mantle cell lymphoma, hairy cell lymphoma, Burkitt's lymphoma, mast cell tumors, Hodgkin's disease, non-Hodgkin's disease, myelodysplastic syndrome, fibrosarcoma, rhabdomyosarcoma; astrocytoma, neuroblastoma, glioma, schwannomas, melanoma, seminoma, teratocarcinoma, osteosarcoma, xenoderma pigmentosum, keratoctanthoma, thyroid follicular cancer, Kaposi's sarcoma, melanoma, teratoma, rhabdomyosarcoma, metastatic and bone disorders, cancer of the bone, mouth/pharynx, esophagus, larynx, stomach, intestine, colon, rectum, lung, liver, pancreas, nerve, brain, head and neck, throat, ovary, uterus, prostate, testis, bladder, kidney, breast, gall bladder, cervix, thyroid, prostate, and skin, non-small cell lung cancer, small cell lung cancer, glioma, and glioblastoma multiforme.

46. The method according to embodiment 37, wherein the MK2-mediated disease or disorder is a cardiovascular or cerebrovascular disorder.

47. The method according to embodiment 46, wherein the cardiovascular or cerebrovascular disorder is selected from the group consisting of atherosclerosis, restenosis of an atherosclerotic coronary artery, acute coronary syndrome, myocardial infarction, cardiac-allograft vasculopathy, stroke, central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

We claim:

1. A compound of formula XX:

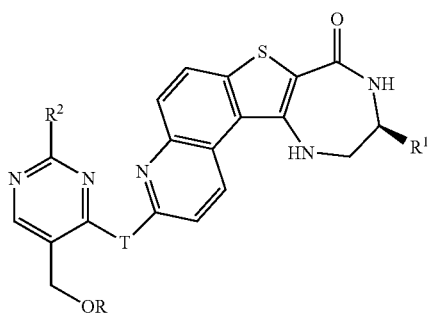

XX or a pharmaceutically acceptable salt thereof, wherein:
T is —NH— or —O—;
R is hydrogen or an optionally substituted $C_{1-6}$ aliphatic;
$R^1$ is methyl;
$R^2$ is halogen, —CN, —$SR^y$, —$S(O)_2R^y$, —$SO_2R^y$, —$OSO_2R^y$, —$OC(O)R^y$, or —$OP(O)_2OR^y$; and
each $R^y$ is independently selected from optionally substituted $C_{1-6}$ aliphatic or optionally substituted phenyl.

2. The compound according to claim 1, wherein T is —O—.

3. The compound according to claim 1, wherein T is —NH—.

4. The compound according to claim 1, wherein $R^2$ is halogen.

5. The compound according to claim 1, wherein $R^2$ is —$SR^y$ or —$SO_2R^y$.

6. A pharmaceutically acceptable composition comprising the compound according to claim 1 and a pharmaceutically acceptable carrier, adjuvant, or vehicle.

7. The compound according to claim 4, wherein $R^2$ is fluoro or chloro.

8. The compound according to claim 4, wherein $R^2$ is chloro.

9. The compound according to claim 2, wherein $R^2$ is chloro.

10. The compound according to claim 1, wherein R is $C_{1-6}$ aliphatic substituted with oxo, halogen, —CN, $(CH_2)_{0-4}R°$, —$(CH_2)_{0-4}OR°$, or —$(CH_2)_{0-4}S(O)_2R°$, wherein R° is $C_{1-6}$ aliphatic.

11. The compound according to claim 9, wherein R is $C_{1-6}$ aliphatic substituted with oxo, halogen, —CN, —$(CH_2)_{0-4}R°$, —$(CH_2)_{0-4}OR°$, or —$(CH_2)_{0-4}S(O)_2R°$, wherein R° is $C_{1-6}$ aliphatic.

12. The compound according to claim 1, wherein the compound is selected from:

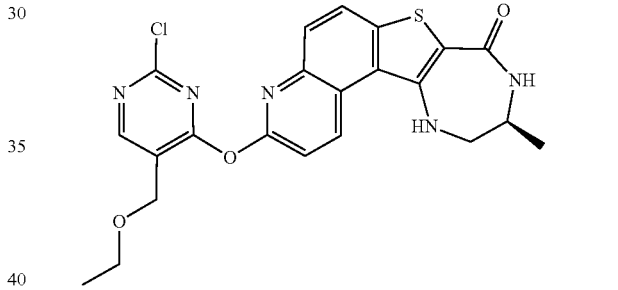

I-82

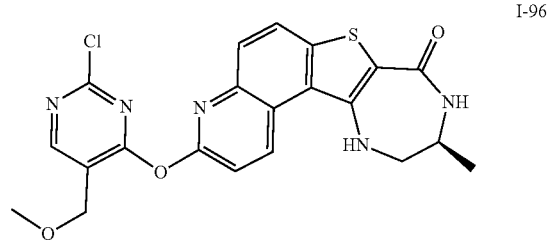

I-96

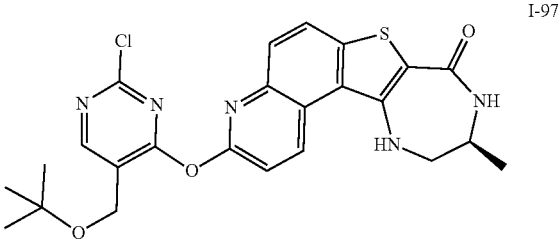

I-97

-continued

I-100
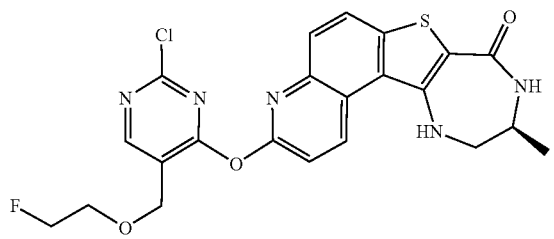

I-121
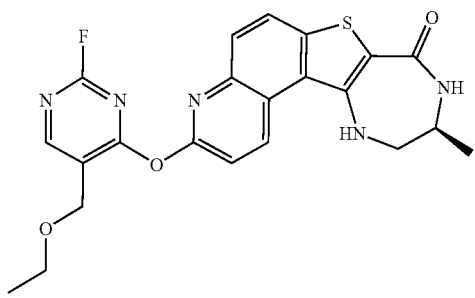

-continued

I-135
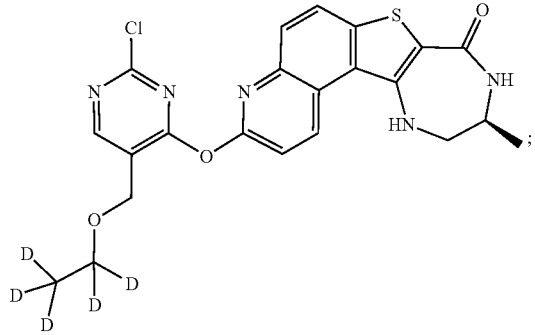

or a pharmaceutically acceptable salt thereof.

13. The compound according to claim 1, wherein the compound is:

I-82
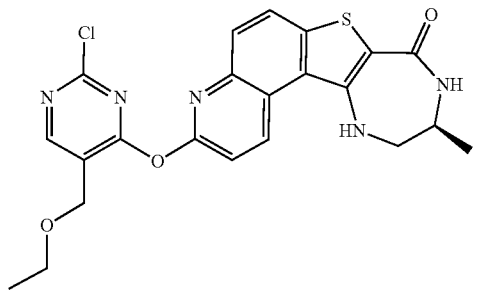

or a pharmaceutically acceptable salt thereof.

14. A pharmaceutically acceptable composition comprising the compound according to claim 11 and a pharmaceutically acceptable carrier, adjuvant, or vehicle.

15. A pharmaceutically acceptable composition comprising the compound according to claim 12 and a pharmaceutically acceptable carrier, adjuvant, or vehicle.

* * * * *

I-127
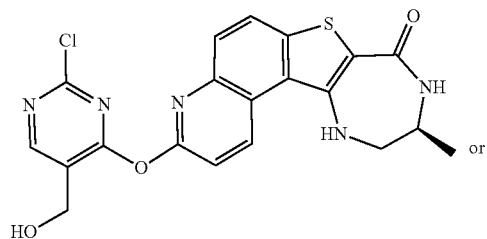 or

SEQUENCE LISTING

<160> NUMBER OF SEQ ID NOS: 2

<210> SEQ ID NO 1
<211> LENGTH: 400
<212> TYPE: PRT
<213> ORGANISM: Homo sapiens

<400> SEQUENCE: 1

```
Met Leu Ser Asn Ser Gln Gly Gln Ser Pro Val Pro Phe Pro Ala
1               5                   10                  15

Pro Ala Pro Pro Gln Pro Thr Pro Ala Leu Pro His Pro Pro
            20                  25                  30

Ala Gln Pro Pro Pro Pro Gln Gln Phe Pro Gln Phe His Val
            35                  40                  45

Lys Ser Gly Leu Gln Ile Lys Lys Asn Ala Ile Ile Asp Asp Tyr Lys
    50                  55                  60

Val Thr Ser Gln Val Leu Gly Leu Gly Ile Asn Gly Lys Val Leu Gln
65                  70                  75                  80

Ile Phe Asn Lys Arg Thr Gln Glu Lys Phe Ala Leu Lys Met Leu Gln
                85                  90                  95

Asp Cys Pro Lys Ala Arg Arg Glu Val Glu Leu His Trp Arg Ala Ser
                100                 105                 110

Gln Cys Pro His Ile Val Arg Ile Val Asp Val Tyr Glu Asn Leu Tyr
                115                 120                 125

Ala Gly Arg Lys Cys Leu Leu Ile Val Met Glu Cys Leu Asp Gly Gly
                130                 135                 140

Glu Leu Phe Ser Arg Ile Gln Asp Arg Gly Asp Gln Ala Phe Thr Glu
145                 150                 155                 160

Arg Glu Ala Ser Glu Ile Met Lys Ser Ile Gly Glu Ala Ile Gln Tyr
                165                 170                 175

Leu His Ser Ile Asn Ile Ala His Arg Asp Val Lys Pro Glu Asn Leu
                180                 185                 190

Leu Tyr Thr Ser Lys Arg Pro Asn Ala Ile Leu Lys Leu Thr Asp Phe
                195                 200                 205

Gly Phe Ala Lys Glu Thr Thr Ser His Asn Ser Leu Thr Thr Pro Cys
    210                 215                 220

Tyr Thr Pro Tyr Tyr Val Ala Pro Glu Val Leu Gly Pro Glu Lys Tyr
225                 230                 235                 240

Asp Lys Ser Cys Asp Met Trp Ser Leu Gly Val Ile Met Tyr Ile Leu
                245                 250                 255

Leu Cys Gly Tyr Pro Pro Phe Tyr Ser Asn His Gly Leu Ala Ile Ser
                260                 265                 270

Pro Gly Met Lys Thr Arg Ile Arg Met Gly Gln Tyr Glu Phe Pro Asn
                275                 280                 285

Pro Glu Trp Ser Glu Val Ser Glu Glu Val Lys Met Leu Ile Arg Asn
                290                 295                 300

Leu Leu Lys Thr Glu Pro Thr Gln Arg Met Thr Ile Thr Glu Phe Met
305                 310                 315                 320

Asn His Pro Trp Ile Met Gln Ser Thr Lys Val Pro Gln Thr Pro Leu
                325                 330                 335

His Thr Ser Arg Val Leu Lys Glu Asp Lys Glu Arg Trp Glu Asp Val
                340                 345                 350

Lys Glu Glu Met Thr Ser Ala Leu Ala Thr Met Arg Val Asp Tyr Glu
                355                 360                 365
```

```
Gln Ile Lys Ile Lys Lys Ile Glu Asp Ala Ser Asn Pro Leu Leu Leu
370                 375                 380

Lys Arg Arg Lys Lys Ala Arg Ala Leu Glu Ala Ala Leu Ala His
385                 390                 395                 400

<210> SEQ ID NO 2
<211> LENGTH: 28
<212> TYPE: PRT
<213> ORGANISM: Homo sapiens

<400> SEQUENCE: 2

Asn Leu Tyr Ala Gly Arg Lys Cys Leu Leu Ile Val Met Glu Cys Leu
1               5                   10                  15

Asp Gly Gly Glu Leu Phe Ser Arg Ile Gln Asp Arg
                20                  25
```